United States Patent [19]

Connell et al.

[11] Patent Number: 5,686,424
[45] Date of Patent: Nov. 11, 1997

[54] 2-OXOETHYL DERIVATIVES AS IMMUNOSUPPRESSANTS

[75] Inventors: Richard D. Connell, New Haven; David G. Osterman, Glastonbury; Michael E. Katz, Wallingford, all of Conn.

[73] Assignee: Miles Inc., West Haven, Conn.

[21] Appl. No.: 431,390

[22] Filed: Apr. 28, 1995

Related U.S. Application Data

[63] Continuation of Ser. No. 981,565, Nov. 25, 1992, abandoned, which is a continuation-in-part of Ser. No. 864,998, Apr. 8, 1992, abandoned.

[51] Int. Cl.$^6$ .................. C07K 5/078; A61K 38/05
[52] U.S. Cl. .................. 514/19; 548/537; 546/245
[58] Field of Search .................. 514/19; 548/537; 546/245

[56] References Cited

U.S. PATENT DOCUMENTS

| | | | |
|---|---|---|---|
| 4,764,503 | 8/1988 | Wenger | 514/11 |
| 4,894,366 | 1/1990 | Okuhara et al. | 514/63 |
| 4,981,792 | 1/1991 | Inamine et al. | 435/119 |
| 5,011,943 | 4/1991 | Wang | 549/214 |
| 5,057,608 | 10/1991 | Wyvratt et al. | 540/456 |

FOREIGN PATENT DOCUMENTS

| | | |
|---|---|---|
| 0323042 | 7/1989 | European Pat. Off. |
| 0358508 | 3/1990 | European Pat. Off. |
| 0396400 | 11/1990 | European Pat. Off. |
| 0427680 | 5/1991 | European Pat. Off. |
| 0428365 | 5/1991 | European Pat. Off. |
| 0455427 | 11/1991 | European Pat. Off. |
| 0463690 | 1/1992 | European Pat. Off. |
| 0465426 | 1/1992 | European Pat. Off. |
| 0466365 | 1/1992 | European Pat. Off. |
| 2244991 | 12/1991 | United Kingdom |
| 2245891 | 1/1992 | United Kingdom |
| 2246350 | 1/1992 | United Kingdom |
| 9102736 | 3/1991 | WIPO |
| 9113889 | 9/1991 | WIPO |
| 91/19495 | 12/1991 | WIPO |
| 92/00314 | 1/1992 | WIPO |
| 92/00980 | 1/1992 | WIPO |

OTHER PUBLICATIONS

Ciabatti, Farmaco 43 (12)989 (1988).
Hauske et al., Design and Synthesis of Novel FKPB Inhibitors J. Med. Chem., 35:4284–4296 (1992).

Primary Examiner—Robert Gerstl

[57] ABSTRACT

A class of compounds that suppress human T-lymphocyte proliferation is disclosed. The active compounds essentially contain at least the following structure:

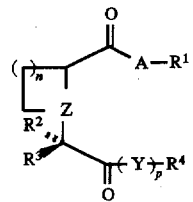

10 Claims, No Drawings

2-OXOETHYL DERIVATIVES AS IMMUNOSUPPRESSANTS

This is a continuation of application Ser. No. 07/981,565 filed on Nov. 25, 1992, now abandoned which is a continuation-in-part of U.S. application Ser. No. 07/864,998 filed Apr. 8, 1992, now abandoned.

BACKGROUND

The invention relates to methods and compounds for controlling inflammatory processes in humans through mediation of inflammatory cell proliferation. More particularly, the present invention is a method for suppressing T-lymphocytes using a class of novel compounds which bind to the FKBP-type family of immunophilins.

Compounds which retard the production of cytokines such as interleukin-2 (IL-2) are known. For instance, U.S. Pat. No. 4,764,503 assigned to Sandoz Ltd., Basel, Switzerland, describes a compound generically referred to as Cyclosporin A (hereinafter referred to as "CsA"), and U.S. Pat. No. 4,894,366 assigned to Fujisawa Pharmaceuticals, Osaka, Japan, describes a compound they designate as "FK506." Both CsA and FK 506 are claimed to inhibit IL-2 production and bind to cellular receptor proteins that possess Peptidyl Prolyl Isomerase (PPIase) activity (Johansson et al., 1990, Transplantation 50:10017).

It was initially postulated by those skilled in the art that the specific binding by such compounds to PPIase type proteins led to inhibition of the protein's isomerase activity which, in turn, led to inhibition of T-cell proliferation. Thus, these PPIase type proteins were referred to as "immunophilins", with the cellular receptor proteins that bound to CsA and FK506 being referred to as "cyclophilin" and "FK506 binding protein", respectively. FK506 binding protein is also simply referred to as "FKBP" (Harding et al., 1989, Nature 341:758).

Recent publications report that the inhibition of PPIase activity, in and of itself, is not sufficient for immunosuppressant activity. However, there is support in the literature that inhibitory binding to PPIase-type enzymes probably contributes to ultimate T-cell suppression (Sigal et al. 1991, J. Exp. Med. 173:619).

This disclosure presents a new class of synthetic compounds that both suppress the proliferation of T-cells and inhibit the isomerase activity of the FKBP-type of PPIases.

CsA, a cyclic undecapeptide, has received FDA approval for use as an adjunct to organ transplant procedures. However, CsA is administered with caution due to its known toxicity. Currently, CsA is prescribed in situations where the risks of non treatment outweigh the risks of its therapeutic complications.

As a result, efforts to expand the application of CsA into non life threatening indications such as chronic maintenance of autoimmune disorders have been limited by the well-known side effects of this drug. The use of CsA leads to a variety of disorders including: nephrotoxicity, such as impairment of glomerular filtration and irreversible interstitial fibrosis (Kopp et al., 1991, J. Am. Soc. Nephrol. 1:162); neurological deficits, such as involuntary tremors, or non-specific cerebral angina such as non-localized headaches (De Groen et al, 1987, N. Engl. J. Med. 317:861); and vascular hypertension with complications resulting therefrom (Kahan et al., 1989, N. Engl. J. Med. 321:1725).

Recent efforts to investigate the cause of the adverse effects of CsA administration have centered on the role of CsA breakdown into toxic metabolites (Bowers et al., 1990, Clin. Chem. 36:1875; Burke et al., 1990, Transplantation 50:901). The prevailing thought is that CsA toxicity is due to such metabolites and not due to the nature of the CsA binding to the PPIase, cyclophilin (Akagi et al., 1991, J. Int. Med. Res. 19:1; Ryffel et al., 1988, Transplantation 46:905).

Thus, inhibitor compounds that do not resemble CsA structurally, yet bind to PPIases, should be more amenable to therapeutic applications. Such non-toxic immunosuppressors would benefit the art, especially for chronic administration such as required in the treatment of autoimmune disorders.

The compound FK506 is structurally different from CsA and does not produce the same type of toxic metabolites. FK506 has been shown to be effective in some transplant patients who do not respond to CsA (Tucci et al., 1989, J. Immunol. 143:718).

However, testing of FK506 in humans was delayed due to severe vasculitis observed in treatment regimens in dogs and baboons (Collier et al., 1988, Transplant Proc. 20:226). Furthermore, other clinical side effects and complications of FK506 administration are being reported (Frayha et al., 1991, Lancet 337:296; Kitahara et al., 1991, Lancet 337:1234). It has also been reported that "overall, the absolute rate of clinical rejection in FK506 [post-organ transplantation] patients is only slightly lower than with current standard therapies" (Holechek, 1991, Anna. J. 18:199).

In an attempt to alleviate the FK506 side effects, many minor modifications to the base structure have been reported. For example, U.S. Pat. No. 5,057,608 assigned to Merck & Co. and WIPO Publication No. WO89/05304 assigned to FISONS PLC Inc. both disclose chemical variations of the FK506 compound.

To date only a few studies on the metabolism of FK506 have been published, and little information has been reported on the toxicity of its metabolites (Johansson et al., 1990, Transplantation 50:1001; Christians et al., 1991, Clinical Biochemistry 24:271; Lhoest et al., 1991, Pharmaceutica Acta Helveticae 66:302). Since it is likely that the pattern of metabolism of the FK506 analogs and derivatives are similar to the parent compound, it is also likely that many of the side effects of FK506 will be shared by the derivatives.

As is true for CsA, the toxicity of FK506 is postulated to be based on its structure and not due to its binding activity with the immunophilin FKBP. It is further postulated that the toxicity of compounds such as CsA and FK506 are due to various chemical groups found in these structures which do not participate in the immunosuppressive activity, such as those groups which result in the toxic metabolites of CsA bioprocessing. Thus, relatively compact molecules which do not resemble either CsA or FK506, and which have both immunosuppressive and PPIase binding activity should be free of side effects associated with CsA and FK506.

Furthermore, the compound FK506 and its derivatives (for example such as disclosed in WIPO Publication No. WO92/00278 assigned to VERTEX Pharmaceuticals Inc.) all share the following homo-proline (6-membered, proline-like) dicarbonyl backbone structure:

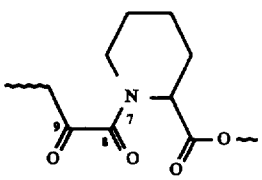

(I)

FK506 and its derivatives all preferably rely on the two carbonyl groups at positions 8 and 9, with the presence of the carbonyl at the number 8 carbon being essential. The presence of the double bond oxygen in proximity to number 7 nitrogen creates an amide type linkage between the nitrogen at position 7 and carbon at position 8.

Recent reports have suggested that the nitrogen at position 7, along with the number 8 and 9 carbonyl groups of FK506 represent "a twist-bond amide" (Michnick et al., 1991, Science 252:836). Based on the data presented in the Michnick et al. article, it was assumed and accepted by those skilled in this art that the carbonyl at position 8 was the functional species. Jorgensen, 1991, Science 254:954, teaches that this keto-amide moiety is critical to activity because the moiety allegedly serves as a transition state analog.

The present description proposes that the carbonyl group at the number 8 position is non-essential for T-cell suppression, and the compounds of the present invention do not rely on this carbonyl group.

The present invention presents a novel class of synthetic inhibitor compounds. The novel class includes synthetic 2-oxoethylene derivatives that bind to human FKBP-type PPIases and demonstrate human peripheral T-lymphocyte inhibitory activity. Moreover, the absence of a carbonyl attached directly to the nitrogen in the proline ring (see formula II, below) provides compounds that possess stability to hydrolysis by proteases at the N-terminus of proline.

It is therefore an object of the present invention to provide for compounds and compositions containing such 2-oxoethylene derivatives for suppression of pathological and abnormal human peripheral T-lymphocyte proliferation.

It is also an object of the present invention to provide a novel class of compounds suitable for therapeutic compositions designed to suppress pathological immune responses, such as the hyperimmune response in organ transplantation rejection, the self-destructive autoimmune diseases, and the overproduction and excessive proliferation of immune cells such as in infectious disease states.

More specific objects include provisions for compounds, compositions and methods for treatment and prevention of rejection of transplanted organs or tissues such as kidney, heart, lung, liver, bone marrow, skin grafts, and corneal replacement.

It is a further object to provide compounds, compositions and methods for use in the treatment of autoimmune, degenerative, inflammatory, proliferative and hyperproliferative diseases, such as rheumatoid arthritis, osteoarthritis, other degenerative joint diseases, joint inflammation such as associated with infectious diseases such as suppurative arthritis, and secondary arthritis such as those associated with gout, hemochromatosis, rheumatic fever, Sjörgens syndrome and tuberculosis.

Another object is to provide compounds, compositions and methods for use in the treatment of lupus erythematosus, systemic lupus erythematosus, Hashimoto's thyroiditis, multiple sclerosis, myasthenia gravis, type 1 diabetes, uveitis, nephrotic syndrome, and of cutaneous manifestations of immunologically-mediated diseases such as psoriasis, atopic dermatitis, contact dermatitis, eczematous dermatitides, seborrheic dermatitis, lichen planus, pemphigus, bollous pemphigoid, epidermolysis bullosa, urticaria, angioedemas, vasculitides, erythemas, cutaneous eosinophilias, and alopecia areata.

Yet another object is to provide compounds, compositions and methods for use in the treatment of abnormal T-cell proliferation such as lymphocytic leukemia; Hodgkin's disease, especially those subtypes involving abnormal T-cell subpopulations; non-Hodgkin's lymphomas, such as mycosis fungoides, convulated lymphocytic lymphoma, and immunoblastic sarcoma; and chronic lymphadenitis.

The above lists are non-limiting, and one skilled in the art could easily adapt the compounds, compositions and methods of the present invention to other indications, such adaptations being within the spirit and scope of the invention which will be described hereinbelow.

SUMMARY OF THE INVENTION

The presently claimed invention relates to an active compound essentially containing at least one of the following structures:

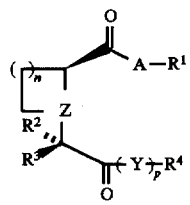

(II)

where:

$R^1$ can be hydrogen, an alkyl, alkylcycloalkyl, alkylaryl, a cycloalkyl, a multicycloalkyl, an aryl, a heterocycle, or an amino acid derivative.

$R^1$ can be optionally substituted with heteroatoms such as oxygen, nitrogen and sulfur as well as heteroatom derivatives containing oxygen, nitrogen and sulfur.

A can be oxygen, sulfur, a nitrogen derivative such as N—$R^5$, or an alkyl derivative such as C($R^6$)—$R^7$, where $R^5$, $R^6$ and $R^7$ can independently be a hydrogen, an alkyl, alkylcycloalkyl, alkylaryl, a cycloalkyl, an aryl, or a heterocycle which can be optionally substituted with heteroatoms such as oxygen, nitrogen and sulfur as well as heteroatom derivatives containing oxygen, nitrogen and sulfur, ($R^1$ and $R^5$), ($R^1$ and $R^6$), ($R^1$ and $R^7$), ($R^1$ and $R^6$ and $R^7$), or ($R^6$ and $R^7$) can be part of a cyclic or multi cyclic structure which is aliphatic or aromatic, and ($R^1$ and $R^5$), ($R^1$ and $R^6$), ($R^1$ and $R^7$), ($R^1$ and $R^6$ and $R^7$), or ($R^6$ and $R^7$) can be optionally substituted with heteroatoms such as oxygen, nitrogen and sulfur as well as heteroatom derivatives containing oxygen, nitrogen and sulfur.

n is an integer from 0 to 5 such that the subsequent ring which is formed is saturated, unsaturated, or partially unsaturated, and such ring structure can be optionally substituted with heteroatoms such as oxygen, nitrogen and sulfur as well as heteroatom derivatives containing oxygen, nitrogen and sulfur.

Z is carbon or nitrogen.

$R^2$ and $R^3$ can independently be hydrogen, an alkyl, alkylcycloalkyl, alkylaryl, a cycloalkyl, an aryl, or a heterocycle.

$R^2$ and $R^3$ can optionally and independently be substituted with heteroatoms such as oxygen, nitrogen and sulfur as well as heteroatom derivatives containing oxygen, nitrogen and sulfur.

$R^2$ and $R^3$ can also be part of a cyclic structure which is aliphatic or alkylaromatic, such a cyclic structure could be optionally substituted with heteroatoms such as oxygen, nitrogen and sulfur as well as heteroatom derivatives containing oxygen, nitrogen and sulfur.

Y can be oxygen, sulfur, a nitrogen derivative such as N—$R^8$, or an alkyl derivative such as $C(R^9)$—$R^{10}$, where $R^8$, $R^9$ and $R^{10}$ can independently be a hydrogen, an alkyl, alkylcycloalkyl, alkylaryl, a cycloalkyl, an aryl, or a heterocycle which can be optionally substituted with heteroatoms such as oxygen, nitrogen and sulfur as well as heteroatom derivatives containing oxygen, nitrogen and sulfur, ($R^9$ and $R^{10}$) can be part of a cyclic or multi cyclic structure which is aliphatic or aromatic, or a heterocycle, ($R^9$ and $R^{10}$) can be optionally substituted with heteroatoms such as oxygen, nitrogen and sulfur as well as heteroatom derivatives containing oxygen, nitrogen and sulfur.

p is an integer from 0 to 1.

$R^4$ is a hydrogen, an alkyl, alkylcycloalkyl, alkylaryl, a cycloalkyl, multicycloalkyl, an aryl, or a heterocycle which can optionally be substituted with heteroatoms such as oxygen, nitrogen and sulfur as well as heteroatom derivatives containing oxygen, nitrogen, sulfur, fluorine, chlorine, and bromine, ($R^4$ and $R^8$), ($R^4$ and $R^9$), ($R^4$ and $R^{10}$), ($R^4$ and $R^9$ and $R^{10}$) can be part of a cyclic or multi cyclic structure which is aliphatic or aromatic, or a heterocycle, and ($R^4$ and $R^8$), ($R^4$ and $R^9$), ($R^4$ and $R^{10}$), ($R^4$ and $R^9$ and $R^{10}$) can be optionally substituted with heteroatoms such as oxygen, nitrogen and sulfur as well as heteroatom derivatives containing oxygen, nitrogen and sulfur.

The term "multi cyclic structure", as used herein, can comprise bicyclic, tricyclic, tetracyclic, or pentacyclic rings, in which the method of attachment could be of a single, double, or spiro-fused nature. Alternatively, these multicyclic arrangements of rings could represent bridged ring systems, both endo and exo.

More specifically, the presently claimed invention relates to active compounds which essentially contain at least one of the following structures:

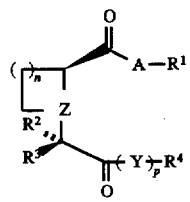
(III)

where:

n, Z, $R^2$, $R^3$, Y, p and $R^4$ have the same meaning as in formula II, above. Likewise, "multi cyclic structure" as used below is defined hereinabove with formula II.

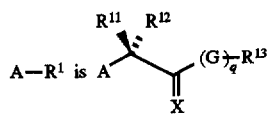

and where A is oxygen, sulfur, or a nitrogen derivatives such as N—$R^{14}$, where $R^{14}$ is hydrogen, alkyl, alkylcycloalkyl, alkylaryl, a cycloalkyl, an aryl, or a heterocycle. $R^{14}$ can be optionally substituted with heteroatoms such as oxygen, nitrogen and sulfur as well as heteroatom derivatives containing oxygen, nitrogen and sulfur.

$R^{11}$ and $R^{12}$ can independently be hydrogen, an alkyl, alkenyl, alkylcycloalkyl, alkylaryl, a cycloalkyl, an aryl, or a heterocycle. $R^{11}$ and $R^{12}$ can be optionally and independently substituted with heteroatoms such as oxygen, nitrogen and sulfur as well as heteroatom derivatives containing oxygen, nitrogen and sulfur.

($R^{11}$ and $R^{12}$) can be part of a cyclic structure which is aliphatic or alkylaromatic. Such cyclic structures could be optionally substituted with heteroatoms such as oxygen, nitrogen and sulfur as well as heteroatom derivatives containing oxygen, nitrogen and sulfur.

X can be an oxygen (forming a carbonyl group with a double bond), or X could represent both a hydroxyl and a proton (each with a single bond attached to the carbon) or two protons (each with a single bond attached to the carbon).

G can be oxygen, sulfur, a nitrogen derivative such as N—$R^{15}$, or an alkyl derivative such as $C(R^{16})$—$R^{17}$, where $R^{15}$, $R^{16}$ and $R^{17}$ can independently be a hydrogen, an alkyl, alkylcycloalkyl, alkylaryl, a cycloalkyl, an aryl, or a heterocycle which can be optionally substituted with heteroatoms such as oxygen, nitrogen and sulfur as well as heteroatom derivatives containing oxygen, nitrogen and sulfur, and $R^{14}$ and G can be part of a cyclic structure which is aliphatic and may be substituted with heteroatoms such as oxygen, nitrogen and sulfur as well as heteroatom derivatives containing oxygen, nitrogen and sulfur.

q is an integer from 0 to 1.

$R^{13}$ can be hydrogen, an alkyl, alkylcycloalkyl, alkylaryl, a cycloalkyl, a multicycloalkyl, an aryl, a heterocycle, or an amino acid derivative, and $R^{13}$ can optionally be substituted with heteroatoms such as oxygen, nitrogen and sulfur as well as heteroatom derivatives containing oxygen, nitrogen and sulfur, where ($R^{13}$ and $R^{15}$), ($R^{13}$ and $R^{16}$), ($R^{13}$ and $R^{17}$), ($R^{13}$ and $R^{16}$ and $R^{17}$), or ($R^{16}$ and $R^{17}$) can be part of a cyclic or multi cyclic structure which is aliphatic or aromatic, and ($R^{13}$ and $R^{15}$), ($R^{13}$ and $R^{16}$), ($R^{13}$ and $R^{17}$), ($R^{13}$ and $R^{16}$ and $R^{17}$), or ($R^{16}$ and $R^{17}$) can be optionally substituted with heteroatoms such as oxygen, nitrogen and sulfur as well as heteroatom derivatives containing oxygen, nitrogen and sulfur.

The compounds of the present invention can be defined further with the following structure,

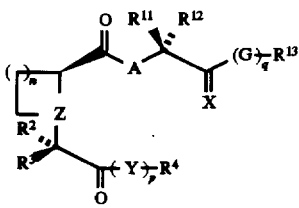

(IV)

where:

n is an integer from 0 to 4, and Z is nitrogen. $R^2$, $R^3$, $R^4$, Y, p, and "multi cyclic structure" have the same meanings as formulas II and III above.

$R^{13}$ can be hydrogen, an alkyl, alkylcycloalkyl, alkylaryl, a cycloalkyl, a multicycloalkyl, an aryl, a heterocycle, or an amino acid derivative.

$R^{13}$ can optionally be substituted with heteroatoms such as oxygen, nitrogen and sulfur as well as heteroatom derivatives containing oxygen, nitrogen and sulfur.

G can be oxygen, a nitrogen derivative such as N—$R^{19}$, or an alkyl derivative such as C($R^{20}$)—$R^{21}$, where $R^{19}$, $R^{20}$ and $R^{21}$ can independently be a hydrogen, an alkyl, alkylcycloalkyl, alkylaryl, a cycloalkyl, an aryl, or a heterocycle which can be optionally substituted with heteroatoms such as oxygen, nitrogen and sulfur as well as heteroatom derivatives containing oxygen, nitrogen and sulfur, ($R^{13}$ and $R^{19}$), ($R^{13}$ and $R^{20}$), ($R^{13}$ and $R^{21}$), ($R^{13}$ and $R^{20}$ and $R^{21}$), or ($R^{20}$ and $R^{21}$) can be part of a cyclic or multi cyclic structure which is aliphatic or aromatic, and ($R^{13}$ and $R^{19}$), ($R^{13}$ and $R^{20}$), ($R^{13}$ and $R^{21}$), ($R^{13}$ and $R^{20}$ and $R^{21}$), or ($R^{20}$ and $R^{21}$) can be optionally substituted with heteroatoms such as oxygen, nitrogen and sulfur as well as heteroatom derivatives containing oxygen, nitrogen and sulfur.

q is an integer from 0 to 1;

X can be an oxygen (forming a carbonyl group with a double bond), or X could represent two protons (each with a single bond attached to the carbon).

$R^{11}$ and $R^{12}$ can independently be hydrogen, an alkyl, alkenyl, alkylcycloalkyl, alkylaryl, a cycloalkyl, an aryl, or a heterocycle; $R^{11}$ and $R^{12}$ can optionally and independently be substituted with heteroatoms such as oxygen, nitrogen and sulfur as well as heteroatom derivatives containing oxygen, nitrogen and sulfur.

($R^{11}$ and $R^{12}$) can be part of a cyclic structure which is aliphatic or alkylaromatic, said cyclic structure could be optionally substituted with heteroatoms such as oxygen, nitrogen and sulfur as well as heteroatom derivatives containing oxygen, nitrogen and sulfur.

A is oxygen or a nitrogen derivative such as N—$R^{18}$, where $R^{18}$ is hydrogen, alkyl, alkylcycloalkyl, alkylaryl, a cycloalkyl, an aryl, or a heterocycle, $R^{18}$ can be optionally substituted with heteroatoms such as oxygen, nitrogen and sulfur as well as heteroatom derivatives containing oxygen, nitrogen and sulfur, and $R^{18}$ and G can be part of a cyclic structure which is aliphatic and may be substituted with heteroatoms such as oxygen, nitrogen and sulfur as well as heteroatom derivatives containing oxygen, nitrogen and sulfur.

A convenient route to prepare the present compounds was to alkylate a selected cyclic amino acid with a selected alpha-halo carbonyl compound. There are a number of possible conditions and variations that could be used for this type of synthesis route, such possibilities being well known to those skilled in the art. (For example, see Miyazawa, 1980, T. Bull. Chem. Soc. Japan 53:2555). The Detailed Description which follows describes steps involving THF and triethylamine, although inorganic bases such as sodium or cesium carbonate also proved quite adequate.

In one embodiment, the present compounds were obtained by alkylating an appropriate alpha-halo carbonyl compound with cyclic alpha amino acids whose C-termini were protected. In certain cases, the protecting group was removed to provide the corresponding acid for coupling. Dehydrative coupling was employed with an appropriately substituted amino acid to provide the corresponding derivative.

In another embodiment, carboalkoxymethyl derivative intermediates were used. Such intermediates were deprotected and coupled with a wide variety of H—Y—$R^4$ (see formula II) derivatives for an alternate route to the desired compounds.

The alpha-halo ketones and esters used are either commercially available or can be prepared from steps available in current literature. For example, the alpha-halo esters can be prepared from the corresponding alcohols by treatment with alpha-halo acetylhalides such as alpha-chloro acetylchloride, and the alpha-halo ketones can be prepared from the corresponding carboxylic acids. Thus, the carboxy groups are transformed into either an acid chloride or an anhydride and treated with diazomethane to provide the corresponding alpha-diazo ketone. The diazo ketones are converted to alpha-halo ketones upon treatment with hydrogen halides such as HCl.

The presently claimed compounds were found to be effective at low micromolar doses in both in vitro PPIase enzyme inhibition assays and in vivo assays for inhibition of mitogen-induced human T-cell proliferation. Moreover, the results from the graft vs. host assay (described in detail further below) indicate that the present class of compounds exhibit desirable biological properties (prophylactic prevention of lymph node swelling), with no obvious toxicity at 100 mg/kg concentrations.

The present invention encompasses pharmaceutical formulations which, in addition to non-toxic, inert pharmaceutically suitable excipients, contain the compounds of the invention.

The present invention also includes pharmaceutical formulations in dosage units. This means that the formulations are present in the form of individual part, for example, tablets, dragees, capsules, caplets, pills, suppositories and ampules, the active compound content of which corresponds to a fraction or a multiple of an individual dose. The dosage units can contain, for example, 1, 2, 3 or 4 individual doses; or ½, ⅓ or ¼ of an individual dose. An individual dose preferably contains the amount of active compound which is given in one administration and which usually corresponds to a whole, one half, one third or one quarter of a daily dose.

By non-toxic inert pharmaceutically suitable excipients there are to be understood solid, semi-solid or liquid diluents, fillers and formulation auxiliaries of all types.

Preferred pharmaceutical formulations which may be mentioned are tablets, dragees, capsules, caplets, pills, granules, suppositories, solutions, suspensions and emulsions, paste, ointments, glues, creams, lotions, dusting powders and sprays. Tablets, dragees, capsules, caplets, pills and granules can contain the active compounds in addition to the customary excipients, such as (a) fillers and extenders, for example, starches, lactose, sucrose, glucose, mannitol and silicic acid, (b) binders, for example, carboxymethylcellulose, alginates, gelatin and polyvinylpyrrolidone, (c) humectants, for example, glycerol, (d) disintegrating agents, for example, agar-agar, calcium carbonate and sodium carbonate, (e) solution retarders, for example, paraffin and (f) absorption accelerators, for example, quaternary ammonium compounds, (g) wetting agents, for example, cetyl alcohol and glycerol monostearate, (h) absorbents, for example, kaolin and bentonite and (i) lubricants, for example, talc, calcium stearate, magnesium stearate and solid polyethylene glycols, or mixtures of the substances listed under (a) to (i) directly hereinabove.

The tablets, dragees, capsules, caplets, pills and granules can be provided with the customary coatings and shells, optionally containing opacifying agents and can also be of such composition that they release the active compounds only or preferentially in a certain part of the intestinal tract, optionally in a delayed manner. Examples of embedding compositions which can be used are polymeric substances and waxes.

The active compounds can also be present in microencapsulated form, if appropriate with one or more of the abovementioned excipients.

Suppositories can contain, in addition to the active compounds, the customary water-soluble or water-insoluble excipients, for example, polyethylene glycols, fats, for example, cacao fat and higher esters (for example, $C_{14}$-alcohol with $C_{16}$-fatty acid), or mixtures of these substances.

Ointments, pastes, creams and gels can contain, in addition to the active compounds, the customary excipients, for example, animal and vegetable fats, waxes, paraffins, starch tragacanth, cellulose derivatives, polyethylene glycols, silicones, bentonites, silicic acid, talc and zinc oxide, or mixtures of these substances.

Dusting powders and sprays can contain, in addition to the active compounds, the customary excipients, for example, lactose, talc, silicic acid, aluminum hydroxide, calcium silicate and polyamide powder, or mixtures of these substances. Sprays can additionally contain customary propellants, for example, chlorofluorohydrocarbons.

Solutions and emulsions can contain, in addition to the active compounds, customary excipients, such as solvents, solubilizing agents and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compounds, customary excipients, such as liquid diluents, for example, water, ethyl alcohol or propylene glycol and suspending agents, for example, ethoxylated isostearyl alcohols, polyoxyethylene sorbitol and sorbitan esters, microcrystalline cellulose, aluminum methydroxide, bentonite, agar-agar, and tragacanth, or mixtures of these substances.

The abovementioned pharmaceutical formulations can also contain other pharmaceutical active compounds in addition to the claimed compounds of the present invention.

The aforementioned pharmaceutical formulations are prepared in the customary manner by known methods, for example, by mixing the active compound or compounds with the excipient or excipients.

The formulations mentioned can be used either with humans and animals, orally, rectally, bucally, parenterally (intravenously, intramuscularly or subcutaneously), intracisternally, intravaginally, intraperitoneally or locally (dusting powder, ointment or drops) and for the therapy of infection in hollow spaces or body cavities. Suitable formulations are injection solutions, solutions and suspensions for oral therapy, gels, pour-on formulations, emulsions, ointments or drops. Ophthalmological and dermatological formulations, silver salts and other salts, ear drops, eye ointments, powders or solutions can be used for local therapy.

It is furthermore possible to use gels, powders, dusting powders, tablets, sustained release tablets, premixes, concentrates, granules, pellets, capsules, caplets, aerosols, sprays and inhalates on humans and animals. The compounds according to the invention can furthermore be incorporated into other carrier materials, such as, for example, plastics (e.g., chains of plastic for local therapy), collagen or bone cement.

DETAILED DESCRIPTION

The following describes a preferred way to prepare the compounds of the present invention.

REAGENTS AND INSTRUMENTS

Anhydrous tetrahydrofuran (THF), ethyl ether ($Et_2O$), and acetonitrile were distilled from calcium hydride prior to use. Unless otherwise stated, all reagents discussed in the following examples were commercially available from Aldrich Chemical Co, Milwakee, Wis., or Janssen Chimica through the U.S. vender Spectrum Chemicals Mfg. Corp., New Brunswick, N.J. The general procedure for converting methyl-ketones to $\alpha$-bromoketones (unless otherwise specified) was according to steps described in Jaques et al., 1988, Org. Synth. Coll. 6:175–178.

All reactions were carried out in oven-dried glassware (140° C.) which were cooled under argon prior to use. Crude products were purified by flash column chromatography using 230–400 mesh silica gel (35–70 um) or medium/high pressure liquid chromatography using Shimadzu LC-8A Preparative liquid chromatography system equipped with columns packed with either 20 um or 10 um silica. Thin layer chromatography (TLC) was performed on aluminum-backed silica gel plates, and visualization was accomplished with a UV light or an iodine vapor chamber.

Proton ($^1H$) nuclear magnetic resonance (NMR) spectra were obtained on GE-OMEGA-300 spectrometers at 300 MHz. Carbon ($^{13}C$) NMR were obtained on these same spectrometers at 75 MHz. Mass spectral data were obtained on a Kratos-MS 80RFA spectrometer using electron impact ionization (EI), chemical ionization (CI), or fast atom bombardment (FAB). Mass Spectral (MS) data were obtained on a Kratos CONCEPT I-H spectrometer, using liquid-cesium secondary ion (LSI) technique, a more modern version of fast atom bombardment (FAB).

Melting points were obtained on a Thomas Hoover capillary melting point apparatus in open-ended capillaries and are not corrected.

EXAMPLE 1

General Process for Preparing alpha-halo Ketones from Carboxylic Acids

2-Chloro-4'-(n-Pentyl) Acetophenone

A solution of 4-pentyl-benzoic acid (1.178 g, 6.13 mmol) and oxalyl chloride (630 uL, 855 mg, 6.74 mmol, 1.1 eq) in dichloromethane (15 mL) was stirred at 22° C. for 10 min, then treated with one drop of N,N-dimethylformamide at 22° C. {Caution, gas evolution may become brisk}. After gas evolution was no longer observed, the flask was fitted with a condenser and warmed to reflux for 30 min. The solution was cooled to −5° C., and cannulated into a cold (−5° C.), ethereal solution of diazomethane (40 mL). After the solution was stirred at −5° C. for 30 min, the flask was removed from the cold bath and the yellow solution was allowed to stir at 22° C. for 2 hrs (preferably in the dark). The solution was concentrated in vacuo, and purified by flash chromatography (5% ethyl acetate in hexane) to provide 33 mg (1.3%) of 2-chloro-4'-(n-pentyl) acetophenone and 586 mg (44%) of 4'-(n-pentyl) diazoacetophenone as a bright yellow oil.

$R_f$ (10% ethyl acetate in hexane) =0.37

$^1$H NMR (300 MHz, CDCl$_3$) δ7.65 (d, J=8.1 Hz, 2H), 7.20 (d, J=7.9 Hz, 2H), 5.93 (s, 1 H, CHN$_2$), 2.60 (m, 2H), 1.58 (m, 2H), 1.27 (m, 4H), 0.86 (t, J=6.9 Hz, 3H). $^{13}$C NMR (75 MHz, CDCl$_3$) δ186.78 (C=O), 149.05, 134.92, 129.31, 127.43, 54.47 (C=N$_2$), 36.53, 32.06, 31.46, 23.14, 14.64.

The diazo compound was quickly taken up in ethyl acetate (120 mL), and the solution was cooled to −5° C. To this was added a 1.0M solution of HCl in ether (Aldrich, 6.0 mL). Gas evolution was observed, and the yellow solution became colorless. The flask was removed from the cold bath and the solution was allowed to stir at 22° C. for 2 hrs. The solution was poured into a separatory funnel, washed with satd aq NaHCO$_3$, dried (MgSO$_4$) and concentrated in vacuo to provide 0.595 g (98% based on starting diazo compd.) of 2-chloro-4'-(n-pentyl) acetophenone as a colorless oil.

$^1$H NMR (300 MHz, CDCl$_3$) δ7.82 (d, J=6.5 Hz, 2H), 7.23 (d, J=6.5 Hz, 2H), 4.64 (s, 2H, CH$_2$Cl), 2.60 (m, 2H), 1.58 (m, 2H), 1.28 (m, 4H), 0.86 (t, J=7.1 Hz, 3H). $^{13}$C NMR (75 MHz, CDCl$_3$) δ191.25 (C=O), 150.55, 132.55, 129.55, 129.27, 46.85 (CH$_2$Cl), 36.63, 32.06, 31.34, 23.14, 14.65.

EXAMPLE 2

General Procedure for Preparing N-Substituted Amides of Amino Acids

N-(tert-Butoxycarbonyl)-L-Isoleucine Benzylamide

Into a 500 mL round bottomed flask equipped with a magnetic stirrer was added N-(tert-butoxycarbonyl)-L-isoleucine (22.53 g, 97.39 mmol, 1.0 eq) and THF (300 mL). The solution was stirred until homogeneous, cooled to −5° C., and treated with N-ethylmorpholine (14.23 mL, 12.88 g, 112.0 mmol, 1.15 eq). The solution was stirred at −5° C. for 20 min, and isobutyl chloroformate (13.24 mL, 13.90 g, 102 mmol, 1.05 eq) was added dropwise over 10 min. After stirring at −5° C. for 30 min, benzylamine (12.24 mL, 12.0 g, 112.0 mmol, 1.15 eq) was added dropwise over 10 min. After the addition was complete, the flask was removed from the cold bath and the solution was stirred at 22° C. for 2.5 hrs. The solution was concentrated to a residue, and partitioned between ethyl acetate (200 mL) and water (100 mL). The aqueous layer was extracted with ethyl ether (2×100 mL) and discarded. The organic extracts were combined, washed with 1N HCl (5×50 mL), 1N NaOH (3×50 mL), satd. aq NaCl (50 mL), and dried (MgSO$_4$). The solution was concentrated in vacuo to provide 29.93 g (96%) of N-(tert-butoxycarbonyl)-L-Isoleucine benzylamide as a white solid.

mp=125°–126° C.

$R_f$ (100% ethyl acetate)=0.74

$R_f$ (50% ethyl acetate in hexane) =0.60

EXAMPLE 3

General Process for Preparing C-Substituted Cyclic Amino Acid Analogs

N-Carbobenzyloxy-L-Proline-L-Isoleucine Benzylamide

Into a 500 mL round bottomed flask equipped with a magnetic stirrer was added N-(tert-butoxycarbonyl)-L-isoleucine benzylamide (29.93 g, 93.53 mmol, 1.0 eq) and dichloromethane (300 mL). The solution was stirred at 22° C. for 10 min until homogeneous, and trifluoroacetic acid (43.22 mL, 63.97 g, 0.57 mol, 6.0 eq) was added (Caution: gas evolution may be brisk!). After TLC analysis indicated that the reaction was complete, the solution was concentrated to an oil, and used directly in the next experiment.

Into a 1-L round bottomed flask equipped with a magnetic stirrer was added N-carbobenzyloxy-L-proline (25.618 g, 102 mmol, 1.0 eq), and dichloromethane (300 mL). The solution was cooled to 0° C., and oxalyl chloride (10.15 mL, 15.02 g, 118.31 mmol, 1.15 eq) was added. After stirring at 0° C. for 5 min, five drops of N,N-dimethylformamide were added (Caution: gas evolution may be brisk!). The solution was stirred at 0° C. for 5 min, the flask was removed from the cold bath, and the solution was stirred at 22° C. for 9 hrs. The solution was concentrated in vacuo to remove all volatiles, dissolved in fresh dichloromethane (300 mL), and cooled to −5° C. This solution was cannulated into a cooled (0° C.) solution containing L-isoleucine N-benzylamide and triethylamine (75.71 g, 748 mmol) dissolved in dichloromethane (100 mL). After the addition was complete, the flask was removed from the cold bath, and the solution was stirred at 22° C. for 3 hrs. The solution was poured into a seperatory funnel and washed with water (3×75 mL), 1N HCl (7×100 mL), 1N NaOH (4×100 mL), satd. aq NaCl (100 mL), and dried (MgSO$_4$). The solution was concentrated in vacuo to provide a crude residue. The residue was recrystallized (ethyl acetate/hexane) to provide 28.72 g (68%) of the product as a white solid. The mother liquor was concentrated to an oil and purified by flash chromatography (20% ethyl acetate) to provide 7.88 g (18.6%) of additional product, or 36.60 g (86%) of N-carbobenzyloxy-L-proline-L-isoleucine benzylamide as a white solid.

mp=151°–153° C.

$R_f$ (50% ethyl acetate in hexane)=0.18

Mass Spectrum (+EI) m/e (rel intensity) 451 (20, M+), 395 (18), 345 (8), 317 (100) 232 (42), 204 (63).

EXAMPLE 4

General Procedure for Hydrogenolysis of Benzyloxy Groups

L-Proline-L-Isoleucine Benzylamide

A solution of N-carbobenzyloxy-L-proline-L-isoleucine benzylamide (36.60 g, 80.95 mmol), 10% palladium on carbon (0.957 g), and methanol (700 mL) was degassed and purged repeatedly (15 times) with hydrogen, and stirred under an atmosphere of hydrogen at 22° C. When TLC analysis indicated the reaction was complete, the solution was purged with argon, filtered through a plug of celite, and concentrated in vacuo to provide 23.71 g, (92%) of L-proline-L-isoleucine benzylamide as a white solid.

mp=135°–136° C.

$R_f$ (100% ethyl acetate)=0.08

EXAMPLE 5

General Procedure for Alkylation of Cyclic Amino Acid Derivatives

L-Isoleucine, N-[1-(2-Benzyloxy-2-Oxoethyl)-L-Prolyl] Benzylamide

A solution of L-proline-L-isoleucine benzylamide (10.22 g, 32.20 mmol), and sodium carbonate (6.824 g, 64.39 mmol, 2.0 eq), in acetonitrile (150 mL) was warmed to reflux until homogeneous, cooled to 22° C., and treated with benzyl 2-bromoacetate (14.75 g, 64.39 mmol, 2.0 eq). The flask was returned to the oil bath and warmed to reflux until TLC indicated the reaction was complete. The heterogeneous solution was filtered, concentrated to a residue, taken up in ethyl acetate (400 mL), and washed with satd aq NaHCO$_3$ (2×50 mL). The solution was dried (MgSO$_4$), concentrated to a residue, and purified by flash chromatography (20% ethyl acetate in hexane) to provide 14.80 g (99%) of L-isoleucine, N-[1-(2-benzyloxy-2-oxoethyl)-L-prolyl] benzylamide as a colorless oil.

$R_f$ (100% ethyl acetate)=0.63

EXAMPLE 6

L-Isoleucine, N-[1-(2-Methoxy-2-Oxoethyl)-L-Prolyl] Benzylamide

Using the procedure described in example 5, treatment of L-proline-L-isoleucine benzylamide (47 mg, 0.15 mmol), with sodium carbonate (31 mg, 0.29 mmol, 2.0 eq), and methyl alpha-bromoacetate (113 mg, 0.74 mmol, 5.0 eq) in acetonitrile (5 mL), provided 50 mg (87%) of L-isoleucine, N-[1-(2-methoxy-2-oxoethyl)-L-prolyl] benzylamide as a white foam.

$R_f$ (50% dichloromethane in ethyl acetate)=0.50

EXAMPLE 7

L-Isoleucine, N-[1-(2-Phenyl-2-Oxoethyl)-L-Prolyl] Benzylamide

Using the procedure described in example 5, treatment of L-proline-L-isoleucine benzylamide (361 mg, 1.14 mmol), with cesium carbonate (0.74 g, 2.28 mmol), and 2-bromoacetophenone (1.134 g, 5.69 mmol, 5.0 eq) in acetonitrile (12 mL), provided 466 mg (94%) of L-isoleucine, N-[1-(2-phenyl-2-oxoethyl)-L-prolyl] benzylamide as a pale yellow oil.

$R_f$ (50% ethyl acetate in hexane)=0.14

$R_f$ (100% ethyl acetate)=0.54

EXAMPLE 8

L-Isoleucine, N-[1-(2-Naphth-2-yl-2-Oxoethyl)-L-Prolyl] Benzylamide

Using the procedure described in example 5, treatment of L-proline-L-isoleucine benzylamide (296 mg, 0.93 mmol), with cesium carbonate (0.61 g, 1.87 mmol), and 2-bromo-2'-acetonaphthone (697 mg, 2.80 mmol, 3.0 eq) in acetonitrile (12 mL), provided 364 mg (80%) of L-isoleucine, N-[1-(2-naphth-2-yl- 2-oxoethyl)-L-prolyl] benzylamide as a pale yellow oil.

$R_f$ (50% ethyl acetate in hexane)=0.25

$R_f$ (100% ethyl acetate)=0.65

EXAMPLE 9

L-Isoleucine, N-[1-(2-(Biphenyl-4-yl)-2-Oxoethyl)-L-Prolyl] Benzylamide

Using the procedure described in example 5, treatment of L-proline-L-isoleucine benzylamide (300 mg, 0.95 mmol), with sodium carbonate (200 mg, 1.89 mmol), and 2-bromo-4'-phenylacetophenone (520 mg, 1.89 mmol, 2.0 eq) in acetonitrile (10 mL), provided 484 mg (87%) of L-isoleucine, N-[1-(2-(biphenyl-4-yl)-2-oxoethyl)-L-prolyl] benzylamide as a colorless oil.

$R_f$ (100% ethyl acetate)=0.62

EXAMPLE 10

L-Isoleucine, N-[1-(2-(2-Methoxyphenyl)-2-Oxoethyl)-L-Prolyl] Benzylamide

Using the procedure described in example 5, treatment of L-proline-L-isoleucine benzylamide (317 mg, 0.99 mmol), with sodium carbonate (211 mg, 1.99 mmol), and 2-bromo-2'-methoxyacetophenone (457 mg, 1.99 mmol, 2.0 eq) in acetonitrile (10 mL), provided 410 mg (88%) of L-isoleucine, N-[1-(2-(2-methoxyphenyl)-2-oxoethyl)-L-prolyl] benzylamide as a pale yellow oil.

$R_f$ (100% ethyl acetate)=0.46

Mass Spectrum (+EI) m/e (rel intensity) 346 (100), 328 (38).

EXAMPLE 11

L-Isoleucine, N-[1-(2-(5-Chloro-3-Methyl-benzo[B] thiophene-2-yl)-2-Oxoethyl)-L-Prolyl] Benzylamide Using the procedure described in example 5, treatment of L-proline-L-isoleucine benzylamide (200 mg, 0.63 mmol), with sodium carbonate (100 mg, 0.94 mmol), and 2-chloroacetyl-5-chloro-3-methylbenzo[B]thiophene (Ryan Scientific; Columbia, S.C.: 244 mg, 0.941 mmol, 1.5 eq) in acetonitrile (10 mL), provided 170 mg (50%) of L-isoleucine, N-[1-(2-(5-chloro-3-methyl-benzo[B] thiophene-2-yl)-2-oxoethyl)-L-prolyl] benzylamide as a pale yellow oil that formed a waxy solid on standing.

$R_f$ (50% ethyl acetate in hexane)=0.17

$R_f$ (100% ethyl acetate)=0.66

Mass Spectrum (+EI) m/e (rel intensity) 540 (5, M+), 539 (10), 330 (100).

EXAMPLE 12

L-Isoleucine, N-[1-(2-(trans,trans-Hexa-2,4-dienyl-1-oxy)-2-Oxoethyl)-L-Prolyl] Benzylamide Using the procedure described in example 5, treatment of L-proline-L-isoleucine benzylamide (201 mg, 0.63 mmol), with cesium carbonate (412 mg, 1.26 mmol), and 1-(2-chloroacetoxy)-2E,4E-hexadiene (prepared from 2E,4E-hexadien-1-ol and 2-chloro acetylchloride: 221 mg, 1.26 mmol, 2.0 eq) in acetonitrile (8 mL), provided 132 mg (46%) of L-isoleucine, N-[1-(2-(1-oxy-2E,4E-hexadienyl)-2-oxoethyl)-L-prolyl] benzylamide as a colorless oil that formed a waxy solid on standing.

$R_f$ (50% ethyl acetate in hexane)=0.29

$R_f$ (70% ethyl acetate in hexane)=0.43

Mass Spectrum (+EI) m/e (rel intensity) 456 (5, M+), 374 (100), 330 (58).

EXAMPLE 13

L-Isoleucine, N-[1-(2-(4-Chlorophenyl)-2-Oxoethyl)-L-Prolyl] Benzylamlde

Using the procedure described in example 5, treatment of L-proline-L-isoleucine benzylamide (182 mg, 0.57 mmol), with sodium carbonate (60 mg, 0.57 mmol), and 2-bromo-4'-chloroacetophenone (147 mg, 0.63 mmol, 1.0 eq), in methanol (10 mL), provided 237 mg (88%) of L-isoleucine, N-[1-(2-(4-chlorophenyl)-2-oxoethyl)-L-prolyl] benzylamide as a pale yellow oil.

$R_f$ (100% ethyl acetate)=0.46

EXAMPLE 14

L-Isoleucine, N-[1-(2-(4-Methylphenyl)-2-Oxoethyl)-L-Prolyl] Benzylamide

Using the procedure described in example 5, treatment of L-proline-L-isoleucine benzylamide (191 mg, 0.60 mmol), with sodium carbonate (70 mg, 0.66 mmol), and 2-bromo- 4'-methylacetophenone (141 mg, 0.66 mmol, 1.1 eq), in methanol (5 mL), provided 210 mg (78%) of L-isoleucine, N-[1-(2-(4-methylphenyl)-2-oxoethyl)-L-prolyl] benzylamide as a pale yellow oil.

$R_f$ (70% ethyl acetate in hexane)=0.30

$R_f$ (100% ethyl acetate)=0.52

EXAMPLE 15

L-Isoleucine, N-[1-(2-(4-Methoxylphenyl)-2-Oxoethyl)-L-Prolyl] Benzylamide

Using the procedure described in example 5, treatment of L-proline-L-isoleucine benzylamide (208 mg, 0.65 mmol), with sodium carbonate (104 mg, 0.98 mmol), and 2-bromo-4'-methoxyacetophenone (195 mg, 0.85 mmol, 1.3 eq) in MeOH (10 mL), provided 248 mg (81%) of L-isoleucine, N-[1-(2-(4-methoxyphenyl)-2-oxoethyl)-L-prolyl] benzylamide as a pale yellow oil.

$R_f$ (100% ethyl acetate)=0.40

EXAMPLE 16

L-Isoleucine, N-Methyl-N-[1-(2-Phenyl-2-Oxoethyl)-L-Prolyl] Benzylamide

Using the procedure described in example 5, 56 mg (0.17 mmol) of L-proline-L-(N-methyl)-isoleucine benzylamide (prepared from N-alpha-t-Boc-N-methyl-L-isoleucine (Schweizerhall, Piscataway, N.J.) using the procedure described in examples 2, 3, and 4) was treated with sodium carbonate (41 mg, 0.40 mmol), and 2-bromoacetophenone (52 mg, 0.26 mmol, 1.5 eq) in methanol (5 mL). A sample of the crude mixture was purified by preparative TLC to provide 2.2 mg of L-Isoleucine, N-Methyl-N-[1-(2-phenyl-2-oxoethyl)-L-prolyl] benzylamide.

$R_f$ (20% ethyl acetate in dichloromethane)=0.24

HRMS calcd for $(M+H)^+$ $[(C_{27}H_{36}N_3O_3+H)^+]$ ion 450.6057; found 450.2760

EXAMPLE 17

L-Isoleucine, N-[1-(2-Phenyl-2-Oxoethyl)-L-Homoproline] Benzylamide

Using the procedure described in example 5, 55 mg (0.17 mmol) of L-homoproline-L-isoleucine benzylamide (prepared from L-homoproline (Bachem Bioscience, Philadelphia, Pa.) using the procedure described in examples 3, and 4), was treated with sodium carbonate (39 mg, 0.37 mmol), and 2-bromoacetophenone (59 mg, 0.29 mmol, 1.7 eq) in methanol (5 mL). A sample of the crude mixture was purified by preparative TLC to provide 34 mg (45%) of L-isoleucine, N-[1-(2-phenyl-2-oxoethyl)-L-homoproline] benzylamide.

$R_f$ (20% ethyl acetate in dichloromethane)=0.31

HRMS calcd for $(M+H)^+$ $[(C_{27}H_{36}N_3O_3+H)^+]$ ion 450.6057; found 450.2760

EXAMPLE 18

L-Phenylglycine, N-[1-(2-Phenyl-2-Oxoethyl)-L-Proline Benzylamide

Using the procedure described in example 5, 285 mg (0.84 mmol) of L-proline-L-phenylglycine benzylamide (prepared from L-phenylglycine (Bachem Bioscience, Philadelphia, Pa.) using the procedure described in Examples 2, 3, and 4), was treated with triethylamine (0.59 mL 4.23 mmol, 5 eq), and 2-bromoacetophenone (185 mg, 0.93 mmol, 1.1 eq) in THF (20 mL). A sample of the crude mixture was purified by preparative TLC to provide 50 mg of L-phenylglycine, N-[1-(2-phenyl-2-oxoethyl)-L-proline benzylamide.

$R_f$ (50% ethyl acetate in hexane)=0.09

HRMS calcd for $(M+H)^+$ $[(C_{28}H_{30}N_3O_3+H)^+]$ ion 456.5688; found 456.2289

EXAMPLE 19

L-Isoleucine, N-[1-(1-Methyl-2-Phenyl-2-Oxoethyl)-L-Prolyl] Benzylamide

Using the procedure described in example 5, treatment of L-proline-L-isoleucine benzylamide (196 mg, 0.62 mmol), with sodium carbonate (85 mg, 0.80 mmol), and 2-bromopropiophenone (210 mg, 0.98 mmol, 1.6 eq) in MeOH (12 mL), provided 72 mg (26%) of L-isoleucine, N-[1-(1-methyl-2-phenyl-2-oxoethyl)-L-prolyl] benzylamide.

$R_f$ (100% ethyl acetate)=0.54

EXAMPLE 20

L-Isoleucine, N-[1-(2-(3-Methoxyphenyl)-2-Oxoethyl)-L-Prolyl] Benzylamide

Using the procedure described in Example 5, treatment of L-proline-L-isoleucine benzylamide (125 mg, 0.39 mmol), with triethylamine (275 uL, 1,97 mmol, 5 eq), and 2-bromo-3'-methoxyacetophenone (107 mg, 0.47 mmol, 1.2 eq) in THF (20 mL), provided 149.2 mg (81%) of L-isoleucine, N-[1-(2-(3-methoxyphenyl)-2-oxoethyl)-L-prolyl] benzylamide as a pale yellow oil.

$R_f$ (50% ethyl acetate in dichloromethane)=0.32

EXAMPLE 21

L-Isoleucine, N-[1-(2-(3,4-Dihydroxyphenyl)-2-Oxoethyl)-L-Prolyl] Benzylamide

Using the procedure described in example 5, treatment of L-proline-L-isoleucine benzylamide (100 mg, 0.31 mmol), with triethylamine (220 uL, 1.58 mmol, 5 eq), and 2-chloro-3'-4'-dihydroxyacetophenone (73 mg, 0.39 mmol, 1.2 eq) in THF (10 mL), provided 54 mg (81%) of L-isoleucine, N-[1-(2-(3,4-dihydroxyphenyl)-2-oxoethyl)-L-prolyl] benzylamide.

$R_f$ (10% MeOH in dichloromethane)=0.51

EXAMPLE 22

L-Isoleucine, N-Methyl-N-[1-(2-Benzyloxy-2-Oxoethyl)-L-Prolyl] Benzylamide

Using the procedure described in example 5 and example 16, treatment of L-proline-L-(N-methyl)-isoleucine benzylamide (43 mg, 0.13 mmol), with triethylamine (90 uL, 0.65 mmol, 1.5 eq), and benzyl 2-bromoacetate (52 mg, 0.26 mmol, 2.0 eq) in THF (2.5 mL), provided 90 mg (64%) of L-isoleucine, N-methyl-N-[1-(2-benzyloxy-2-oxoethyl)-L-Prolyl] benzylamide.

$R_f$ (50% ethyl acetate in dichloromethane)=0.43

HRMS calcd for $(M+H)^+$ $[(C_{28}H_{38}N_3O_4+H)^+]$ ion 480.6328; found 480.2864.

EXAMPLE 23

L-Isoleucine, N-[1-(2-(Benzyloxy)-2-Oxoethyl)-L-Homoproline Benzylamide

Using the procedure described in Example 5 and Example 17, L-homoproline-L-isoleucine benzylamide (43 mg, 0.13 mmol), was treated with triethylamine (91 uL, 0.65 mmol, 1.5 eq), and benzyl 2-bromoacetate (41 uL, 0.26 mmol, 2.0 eq) in THF (2.5 mL). Purification by HPLC provided 54.3 mg of L-isoleucine, N-[1-(2-(carbobenzyloxymethylene)-2-oxoethyl)-L-homoprolyl] benzylamide.

$R_f$ (50% ethyl acetate in dichloromethane)=0.52

HRMS calcd for $(M+H)^+$ $[(C_{28}H_{38}N_3O_4+H)^+]$ ion 480.6328; found 480.2864.

EXAMPLE 24

L-Isoleucine, N-[1-(2-Adamantan-1-yl-2-Oxoethyl)-L-Prolyl] Benzylamide

Using the procedure described in Example 5, treatment of a solution of L-proline-L-isoleucine benzylamide (160.7 mg, 0.50 mmol), with triethylamine (3.53 mL, 2.53 mmol, 5.0 eq), and 1-adamantyl bromomethyl ketone (156 mg, 0.61 mmol, 1.2 eq) in THF (20 mL), provided 180 mg (99%) of L-isoleucine, N-[1-(2-adamantan-1-yl-2-oxoethyl)-L-Prolyl] benzylamide as a white foam.

$R_f$ (50% dichloromethane in ethyl acetate)=0.45

HRMS calcd for $(M+H)^+$ $[(C_{30}H_{44}N_3O_3+H)^+]$ ion 494.7030; found 494.3385.

EXAMPLE 25

L-Isoleucine, N-[1-(2-(Carbo-tert-Butoxy)-2-Oxoethyl)-L-Proline] Benzylamide

Using the procedure described in Example 5, treatment of a solution of L-proline-L-isoleucine benzylamide (66 mg, 0.21 mmol), with triethylamine (147 uL, 1.05 mmol, 5.0 eq), and alpha-bromo-tert-butylacetate (68 uL, 0.42 mmol, 2 eq) in THF (5 mL), provided 70 mg (77%) of L-isoleucine, N-[1-(2-(carbo-tert-butoxymethylene)-2-oxoethyl)-L-proline] benzylamide.

$R_f$ (50% dichloromethane in ethyl acetate)=0.51

HRMS calcd for $(M+H)^+$ $[(C_{24}H_{38}N_3O_4+H)^+]$ ion 432.5884; found 432.2864

EXAMPLE 26

L-Isoleucine, N-[1-(2-tert-Butyl-2-Oxoethyl)-L-Proline] Benzylamide

Using the procedure described in Example 5, treatment of a solution of L-proline-L-isoleucine benzylamide (69 mg, 0.21 mmol), with triethylamine (151 uL, 1.08 mmol, 5.0 eq), and 1-bromopinacolone (58 uL, 0.43 mmol, 2 eq) in THF (5 mL), provided 35 mg (39%) of L-isoleucine, N-[1-(2-tert-butyl-2-oxoethyl)-L-proline] benzylamide as a colorless oil.

$R_f$ (50% dichloromethane in ethyl acetate)=0.42

HRMS calcd for $(M+H)^+$ $[(C_{24}H_{38}N_3O_4+H)^+]$ ion 416.5863; found 416.2915

EXAMPLE 27

L-Isoleucine, N-[1-(2-(2,5-Dimethoxyphenyl)-2-Oxoethyl)-L-Prolyl] Benzylamide

Using the procedure described in Example 5, treatment of a solution of L-proline-L-isoleucine benzylamide (51 mg, 0.16 mmol), with triethylamine (113 uL, 0.81 mmol, 5.0 eq), and 2-bromo-2'-5'-dimethoxyacetophenone (50 mg, 0.19 mmol, 1.2 eq) in THF (5 mL), provided 60 mg (75%) of L-isoleucine, N-[1-(2-( 2,5-dimethoxyphenyl)-2-oxoethyl)-L-prolyl] benzylamide as a colorless oil.

$R_f$ (50% dichloromethane in ethyl acetate)=0.36

HRMS calcd for $(M+H)^+$ $[(C_{28}H_{38}N_3O_5+H)^+]$ ion 496.6307; found 496.2813

EXAMPLE 28

L-Isoleucine, N-[1-(2-(2,4-Dimethoxyphenyl)-2-Oxoethyl)-L-Prolyl] Benzylamide

Using the procedure described in Example 5, treatment of a solution of L-proline-L-isoleucine benzylamide (51 mg, 0.16 mmol), with triethylamine (112 uL, 0.80 mmol, 5.0 eq), and 2-bromo-2'-4'-dimethoxyacetophenone (50 mg, 0.19 mmol, 1.2 eq) in THF (5 mL), provided 55 mg (70%) of L-isoleucine, N-[1-(2-(2,4-dimethoxyphenyl)-2-oxoethyl)-L-prolyl] benzylamide as a colorless oil.

$R_f$ (50% dichloromethane in ethyl acetate)=0.34

EXAMPLE 29

L-Isoleucine, N-[1-(2-(2-Nitrophenyl)-2-Oxoethyl)-L-Prolyl] Benzylamide

Using the procedure described in Example 5, treatment of a solution of L-proline-L-isoleucine benzylamide (54 mg, 0.17 mmol), with triethylamine (118 uL, 0.84 mmol, 5.0 eq), and 2-bromo-2'-nitroacetophenone (50 mg, 0.20 mmol, 1.2 eq) in THF (5 mL), provided 46 mg (57%) of L-isoleucine, N-[1-(2-(2-nitrophenyl)-2-oxoethyl)-L-prolyl] benzylamide.

$R_f$ (50% dichloromethane in ethyl acetate)=0.29

EXAMPLE 30

L-Isoleucine, N-[1-(2-(4-Nitrophenyl)-2-Oxoethyl)-L-Prolyl] Benzylamide

Using the procedure described in Example 5, treatment of a solution of L-proline-L-isoleucine benzylamide (50 mg, 0.16 mmol), with triethylamine (110 uL, 0.79 mmol, 5.0 eq), and 2-bromo-4'-nitroacetophenone (48 mg, 0.20 mmol, 1.2 eq) in THF (5 mL), provided crude material that was additionally purified by preparative TLC to provide 8.8 mg (12%) of L-isoleucine, N-[1-(2-(4-nitrophenyl)-2-oxoethyl)-L-prolyl] benzylamide.

$R_f$ (50% dichloromethane in ethyl acetate)=0.30

HRMS calcd for $(M+H)^+$ $[(C_{26}H_{33}N_4O_5+H)^+]$ ion 481.5754; found 481.2453

EXAMPLE 31

L-Isoleucine, N-[1-(2-(3-Benzyloxyphenyl)-2-Oxoethyl)-L-Prolyl] Benzylamide

Using the procedure described in Example 5, treatment of a solution of L-proline-L-isoleucine benzylamide (111 mg, 0.35 mmol), with triethylamine (245 uL, 1.75 mmol, 5.0 eq), and 2-bromo-3'-benzloxyacetophenone (129 mg, 0.42 mmol, 1.2 eq) in THF (10 mL), provided 147 mg (76%) of L-isoleucine, N-[1-(2-(3-benzyloxyphenyl)-2-oxoethyl)-L-prolyl] benzylamide.

$R_f$ (50% dichloromethane in ethyl acetate)=0.38

HRMS calcd for $(M+H)^+$ $[(C_{33}H_{40}N_3O_4+H)^+]$ ion 542.7028; found 542.3021

EXAMPLE 32

L-Isoleucine, N-[1-(2-(2,4-Dimethylphenyl)-2-Oxoethyl)-L-Prolyl] Benzylamide

Using the procedure described in Example 5, treatment of a solution of L-proline-L-isoleucine benzylamide (60 mg, 0.19 mmol), with triethylamine (130 uL, 0.94 mmol, 5.0 eq), and 2-bromo-2',4'-dimethylacetophenone (52 mg, 0.23 mmol, 1.2 eq) in THF (7 mL), provided a crude product. A portion of the product was purified by preparative TLC to provide 19 mg (21%) of L-isoleucine, N-[1-(2-(2,4-dimethylphenyl)-2-oxoethyl)-L-prolyl] benzylamide.

$R_f$ (50% dichloromethane in ethyl acetate)=0.38

HRMS calcd for $(M+H)^+$ $[(C_{28}H_{38}N_3O_3+H)^+]$ ion 464.6319; found 464.2915

EXAMPLE 33

L-Isoleucine, N-[1-(2-(4-Fluorophenyl)-2-Oxoethyl)-L-Prolyl] Benzylamide

Using the procedure described in Example 5, treatment of a solution of L-proline-L-isoleucine benzylamide (56 mg, 0.18 mmol), with triethylamine (123 uL, 0.88 mmol, 5.0 eq), and 2-bromo-4'-fluoroacetophenone (37 mg, 0.21 mmol, 1.2 eq) in THF (7 mL), provided a crude product. A portion of the product was purified by preparative TLC to provide 28 mg (35%) of L-isoleucine, N-[1-(2-(4-fluorophenyl)-2-oxoethyl)-L-prolyl] benzylamide.

$R_f$ (50% dichloromethane in ethyl acetate)=0.35

EXAMPLE 34

L-Isoleucine, N-[1-(2-(4-Bromophenyl)-2-Oxoethyl)-L-Prolyl] Benzylamide

Using the procedure described in Example 5, treatment of a solution of L-proline-L-isoleucine benzylamide (57 mg, 0.18 mmol), with triethylamine (130 uL, 0.93 mmol, 5.0 eq), and 2,-4'-dibromoacetophenone (63 mg, 0.22 mmol, 1.2 eq) in THF (7 mL), provided a crude product. A portion of the product was purified by preparative TLC to provide 62 mg (67%) of L-isoleucine, N-[1-(2-(4-bromophenyl)-2-oxoethyl)-L-prolyl] benzylamide.

$R_f$ (10% MeOH in dichloromethane)=0.70

EXAMPLE 35

L-Isoleucine, N-[1-(2,4-Dichlorophenylcarbamoylmethyl)-L-Proline] Benzylamide

Using the procedure described in Example 5, treatment of a solution of L-proline-L-isoleucine benzylamide (58 mg, 0.18 mmol), with triethylamine (130 uL, 0.93 mmol, 5.0 eq), and N-chloroacetyl-2,4-dichloroaniline (53 mg, 0.22 mmol, 1.2 eq) in THF (7 mL), provided a crude product. A portion of the product was purified by preparative TLC to provide 30 mg (32%) of L-isoleucine, N-[1-(2,4-dichlorophenylcarbamoylmethyl)-L-proline] benzylamide.

$R_f$ (10% MeOH in dichloromethane)=0.70

EXAMPLE 36

L-Isoleucine, N-[1-(2-Adamantan-1-yl-2-Oxoethyl)-L-Homoproline] Benzylamide

Using the procedure described in Example 5 and Example 17, L-homoproline-L-isoleucine benzylamide (75 mg, 0.22 mmol), was treated with triethylamine (0.15 mL, 1.12 mmol, 5 eq), 1-adamantyl bromomethyl ketone (92 mg, 0.36 mmol, 1.6 eq), and THF (10 mL), to provide 64 mg (56%) of L-isoleucine, N-[1-(2-adamantan-1-yl-2-oxoethyl)-L-homoproline] benzylamide.

$R_f$ (50% ethyl acetate in dichloromethane)=0.56

HRMS calcd for $(M+H)^+$ $[(C_{31}H_{46}N_3O_3+H)^+]$ ion 508.7290; found 508.3532

EXAMPLE 37

L-Isoleucine, N-[1-(2-Furan-2-yl-2-Oxoethyl)-L-Prolyl] Benzylamide

Using the procedure described in Example 5, a solution of L-proline-L-isoleucine benzylamide (114 mg, 0.36 mmol), and triethylamine (0.10 mL, 0.78 mmol, 2.0 eq), in THF (10 mL), was treated with 255 mg (1.76 mmol, 5.0 eq) of 2-(alpha-chloroacyl)furan (prepared from 2-furoic acid, using the procedure described in example 1) to provide 130 mg, (85%) of L-isoleucine, N-[1-(2-furan-2-yl-2-oxoethyl)-L-prolyl] benzylamide.

$R_f$ (100% ethyl acetate)=0.25

EXAMPLE 38

L-Isoleucine, N-[1-(2-Pyrid-2-yl-2-Oxoethyl)-L-Prolyl] Benzylamide

Using the procedure described in Example 5, a solution of L-proline-L-isoleucine benzylamide (148 mg, 0.47 mmol), and triethylamine (0.13 mL, 0.93 mmol, 2.0 eq) in THF (10 mL), was treated with 234 mg (1.50 mmol) of 2-(alpha-chloroacyl)pyridine (prepared from picolinic acid, using the procedure described in example 1) to provide 20 mg, (10%) of L-isoleucine, N-[1-(2-pyrid-2-yl-2-oxoethyl)-L-prolyl] benzylamide.

Rf (50% ethyl acetate in hexane) 0.47

EXAMPLE 39

L-Isoleucine, N-[1-(2-Aminoadamant-1-yl-2-oxoethyl)-L-Prolyl] Benzylamide

Using the procedure described in Example 5, a solution of L-proline-L-isoleucine benzylamide (115 mg, 0.36 mmol), and triethylamine (253 uL, 1.8 mmol, 5.0 eq) in THF (5 mL) was treated with 93 mg (0.43 mmol) of N-(alpha-chloroacyl) 1-aminoadamantane (prepared from 1-adamantanamine and 2-chloroacetyl chloride) to provide 135 mg, (73%) of L-isoleucine, N-[1-(adamant-1-ylcarbamoylmethyl)-L-prolyl] benzylamide.

Rf (100% ethyl acetate)=0.12

HRMS calcd for $(M+H)^+$ $[(C_{30}H_{45}N_4O_3+H)^+]$ ion 509.7166; found 509.3494

EXAMPLE 40

L-Isoleucine, N-[1-(2-(cis-Octahydro-pentalen-1-yl)-2-Oxoethyl)-L-Prolyl]Benzylamide

Using the procedure described in Example 5, a solution of L-proline-L-isoleucine benzylamide (115 mg, 0.36 mmol), and triethylamine (346 uL, 2.5 mmol, 5.0 eq), in THF (2 mL), was treated with 181 mg ( 0.97 mmol ) of 1-chloro-2-(octahydro-pentalen-1-yl)-2-oxoethane (prepared from cis-bicyclo[3.3.0]octane-2 -carboxylic acid using the procedure described in example 1) to provide 52 mg, (23%) of L-isoleucine, N-[1-(2-(cis-octahydro-pentalen-1-yl)-2-oxoethyl)-L-prolyl] benzylamide.

Rf (50% ethyl acetate in dichloromethane)=0.36

EXAMPLE 41

L-Isoleucine, N-[1-[2-(2,6,6-Trimethyl-Bicyclo[3.1.1]hept-3-yl)-2-Oxoethyl]-L-Prolyl] Benzylamide

Using the procedure described in Example 5, a solution of L-proline-L-isoleucine benzylamide (153 mg, 0.48 mmol) and triethylamine (337 uL, 5.0 eq), in THF (2 mL), was treated with 205 mg (0.95 mmol) of 1-chloro-2-(2,6,6-trimethyl-bicyclo[3.1.1]hept-3-yl)-2-oxoethane (prepared from (−)-3-pinanecarboxylic acid using the procedure described in example 1) to provide 164 mg, (68%) of L-isoleucine, N-[1-[(2-(2,6,6-trimethyl-bicyclo[3.1.1]hept-3-yl)-2-oxoethyl]-L-prolyl] benzylamide.

Rf (50% ethyl acetate in dichloromethane)=0.42

EXAMPLE 42

L-Isoleucine, N-[1-(2-(4-Pentylcyclohexyl)-2-Oxoethyl)-L-Prolyl] Benzylamide

Using the procedure described in Example 5, a solution of L-proline-L-isoleucine benzylamide (160 mg, 0.50 mmol), and triethylamine (352 uL, 2.53 mmol, 5.0 eq), in THF (2 mL), was treated with 232 mg (1.0 mmol) of 1-chloro-2-(4-pentylcyclohexyl)-2-oxoethane (prepared from trans-4-pentylcyclohexanecarboxylic acid using the procedure described in example 1) to provide 154 mg, (25%) of L-isoleucine, N-[1-(2-(4-pentylcyclohexyl)-2-oxoethyl)-L-prolyl] benzylamide.

Rf (50% ethyl acetate in dichloromethane)=0.45

EXAMPLE 43

L-Isoleucine, N-[1-(2-(1,2,3,4-tetrahydro-Napththalen-2-yl)-2-Oxoethyl)-L-Prolyl] Benzylamide Using the procedure described in Example 5, a solution of L-proline-L-isoleucine benzylamide (162 mg, 0.51 mmol), and triethylamine (355 uL, 5.0 eq), THF (2 mL), was treated with 212 mg (2.0 eq) of 1-chloro-2-(1,2,3,4-tetrahydro-napththalen-2-yl)-2-oxoethane (prepared from 1,2,3,4-tetrahydro-2-napththoic acid using the procedure described in Example 1) to provide 191 mg (77%) of L-isoleucine, N-[1-(2-(1,2,3,4-tetrahydro-napththalen-2-yl)-2-oxoethyl)-L-prolyl] benzylamide.

Rf (50% ethyl acetate in dichloromethane)=0.42

EXAMPLE 44

L-Isoleucine, N-[1-(2-(1-Methyl-Cyclohexyl)-2-Oxoethyl)-L-Prolyl] Benzylamide

Using the procedure described in Example 5, a solution of L-proline-L-isoleucine benzylamide (164 mg, 0.51 mmol), and triethylamine (355 uL, 5.0 eq) in THF (2 mL), was treated with 180 mg (2.0 eq) of 1-chloro-2-(1-methyl-cyclohexyl)-2-oxoethane (prepared from 1-methyl-1-cyclohexanecarboxylic acid using the procedure described in example 1) to provide 183 mg (93%) of L-isoleucine, N-[1-(2-(1-methyl-cyclohexyl)-2-oxoethyl)-L-prolyl] benzylamide as a colorless residue.

Rf (66% ethyl acetate in hexane)=0.32

EXAMPLE 45

L-Isoleucine, N-[1-(2-Oxo-2-Tricyclo[3.3.1.0 $^{3,7}$]Non-3-yl-Ethyl)-L-Prolyl] Benzylamide Using the procedure described in Example 5, a solution of L-proline-L-isoleucine benzylamide (167 mg, 0.52 mmol), and triethylamine (367 uL, 5.0 eq) in THF (2 mL), was treated with 209 mg (1.2 eq) of 1-chloro-2-oxo-2-tricyclo[3.3.1.0 $^{3,7}$]non-3-yl-ethane (prepared from 3-noradamantanecarboxylic acid using the procedure described in example 1) to provide 181 mg of L-isoleucine, N-[1-(2-oxo-2-tricyclo[3.3.1.0 $^{3,7}$]non-3-yl-ethyl)-L-prolyl] benzylamide as a colorless residue.

Rf (9% methanol in dichloromethane)=0.70

EXAMPLE 46

L-Isoleucine, N-[1-(2-Oxo-3-(3-Methyl-Adamantan-1-yl)-Propyl)-L-Prolyl] Benzylamide
Using the procedure described in Example 5, a solution of L-proline-L-isoleucine benzylamide (162 mg, 0.51 mmol), and triethylamine (358 uL, 5.0 eq), in THF (2 mL), was treated with 246 mg ( 1.0 eq) of 1-chloro-2-oxo-3-(3-methyl-adamantan-1-yl) -propane (prepared from 3-methyl-1-adamantaneacetic acid using the procedure described in example 1) to provide 210 mg (78%) of L-isoleucine, N-[1-(2-oxo-3-(3-methyl-adamantan-1-yl)-propyl)-L-prolyl] benzylamide as a colorless residue.

Rf (50% ethyl acetate in hexane)=0.43

EXAMPLE 47

General Procedure for Attachment of A—$R^1$ Groups.
L-Proline, 1-(2-Adamantan-1-yl-2-Oxoethyl)Benzyl Ester Using the procedure described in Example 5, a solution containing the hydrochloride salt of L-proline benzyl ester (25.46 g, 105.3 mmol), triethylamine (58.0 mL, 414 mmol, 4.0 eq), 1-adamantyl bromomethyl ketone (26.6 g, 103.4 mmol, 1.0 eq) and THF (500 mL), was warmed to reflux, cooled, and purified by flash chromatography to provide 30.0 g (76%) of L-proline, 1-(2-adamantan-1-yl-2-oxoethyl) benzyl ester as a white foam.

$R_f$ (50% dichloromethane in ethyl acetate)=0.42

EXAMPLE 48

1-(2-Adamantan-1-yl-2-Oxoethyl) L-Proline

Using the procedure described in Example 4, a solution of L-proline, 1-(2-adamantan-1-yl-2-oxoethyl) benzyl ester (30.0 g, 76.63 mmol), 10% palladium on carbon (4.2 g), and methanol (100 mL) was purged with hydrogen, and stirred under an atmosphere of hydrogen until no more benzyl ester was observed by TLC. The solution was purged with argon, filtered through a plug of celite, and concentrated in vacuo, and recrystallized from ethyl ether to provide 19.45 g, (85%) of 1-(2-adamantan-1-yl-2-oxoethyl) L-proline as a white solid.

mp 130–142 (sweat), 143–145 (melt)

$R_f$ (20% MeOH in dichloromethane)=0.32

EXAMPLE 49

N-[2-(Biphenyl-4-yl)-2-Oxoethyl] L-Proline

Using the procedure described in Example 47 and Example 48, a solution of the hydrochloride salt of L-proline benzyl ester (20.75 g, 98.0 mmol), was treated with cesium carbonate (87.1 g, 267 mmol, 3.0 eq), 2-bromo-4'-phenylacetophenone (24.5 g, 89.0 mmol, 1.0 eq) in acetonitrile (500 mL), to provide 10.07 g (28%) of L-proline, N-[2-(biphenyl-4-yl)-2-oxoethyl] benzyl ester. This intermediate was taken up in methanol (300 mL) and treated with 10% palladium on carbon (908 mg). Hydrogenation as described in example 4, followed by recrystallization from ethyl ether provided 1.72 g (6.2% overall) of N-[2-(biphenyl-4-yl)-2-oxoethyl] L-proline as a white solid.

mp=182°–184° C.

$R_f$ (17% MeOH in dichloromethane)=0.38

EXAMPLE 50

L-Isoleucine, N-[1-(2-(Biphenyl-4-yl)-2-Oxoethyl)-L-Prolyl] 1,2,3,4-Tetrahydroisoquinolinamide A solution of N-[2-(biphenyl-4-yl)-2-oxoethyl] L-proline (50 mg, 0.16 mmol, 1.0 eq), N-ethylmorpholine (125 uL, 0.97 mmol, 6 eq) in acetonitrile (0.5 mL) was cooled to 0° C. and treated with a 50% solution of 1-n-propylphosphonic acid cyclic anhydride in dichloromethane ( 170 uL, 0.26 mmol, 1.6 eq) followed by the L-isoleucine 1,2,3,4-tetrahydroisoquinolinamide (47.9 mg, 0.19 mmol, 1.2 eq). Purification by HPLC provided 5.53 mg (6.3%) of L-Isoleucine, N-[1-(2-(Biphenyl-4-yl)-2-oxoethyl)-L-prolyl]1,2,3,4-tetrahydroisoquinolinamide.

Rf (50% ethyl acetate in hexane)=0.51

HRMS calcd for $(M+H)^+$ $[(C_{34}H_{40}N_3O_3+H)^+]$ ion 538.7154; found 538.3072

EXAMPLE 51

L-Isoleucine, N-[1-(2-(Biphenyl-4-yl)-2-Oxoethyl)-L-Prolyl] Benzyl Ester

A solution of N-[2-(biphenyl-4-yl)-2-oxoethyl]_0 L-proline (102 mg, 0.33 mmol, 1.0 eq), N-ethylmorpholine (270 uL, 2.12 mmol, 6.4 eq) in acetonitrile (1.0 mL) was cooled to 0° C. and treated with a 50% solution of 1-n-propylphosphonic acid cyclic anhydride in dichloromethane (340 uL, 0.53 mmol, 1.6 eq) followed by the tosylate salt of L-isoleucine benzyl ester (143 mg, 0.36 mmol, 1.1 eq). Purification by HPLC provided 45 mg (26%) of L-isoleucine, N-[1-(2-(biphenyl-4-yl)-2-oxoethyl)-L-prolyl] benzyl ester.

Rf 50% ethyl acetate in hexane)=0.29

EXAMPLE 52

L-Isoleucine, N-[1-(2-(Biphenyl-4-yl)-2-Oxoethyl)-L-Prolyl] tert-Butylamide

A solution of N-[2-(biphenyl-4-yl)-2-oxoethyl] L-proline (50 mg, 0.16 mmol, 1.0 eq), N-ethylmorpholine (125 uL, 0.98 mmol, 6 eq) in acetonitrile (0.5 mL) was cooled to 0° C. and treated with a 50% solution of 1-n-propylphosphonic acid cyclic anhydride in dichloromethane (170 uL, 0.27 mmol, 1.6 eq) followed by L-isoleucine tert-butylamide (49 mg, 0.19 mmol, 1.1 eq). Purification by HPLC provided 12 mg (16%) of L-isoleucine, N-[1-(2-(biphenyl-4-yl)-2-oxoethyl)-L-prolyl] tert-butylamide.

Rf 50% ethyl acetate in hexane)=0.38

HRMS calcd for $(M+H)^+$ $[(C_{29}H_{40}N_3O_3+H)^+]$ ion 478.6604; found 478.3072

EXAMPLE 53

L-Phenylalanine, N-[1-(2-(Biphenyl-4-yl)-2-Oxoethyl)-L-Prolyl] Benzylamide

A solution of N-[2-(biphenyl-4-yl)-2-oxoethyl] L-proline (51 mg, 0.16 mmol, 1.0 eq), N-ethylmorpholine (125 uL, 0.98 mmol, 6 eq) in acetonitrile (0.5 mL) was cooled to 0° C. and treated with a 50% solution of 1-n-propylphosphonic acid cyclic anhydride in dichloromethane (170 uL, 0.27 mmol, 1.6 eq) followed by phenylalanine benzylamide (49 mg, 0.19 mmol, 3.1 eq). Purification by HPLC provided 12 mg (14%) of L-phenylalanine, N-[1-(2-(biphenyl-4-yl)-2-oxoethyl)-L-prolyl] benzylamide.

Rf 50% ethyl acetate in hexane)=0.38

EXAMPLE 54

L-Methionine, N-[1-(2-(Biphenyl-4-yl)-2-Oxoethyl)-L-Prolyl] Benzylamide

A solution of N-[2-(biphenyl-4-yl)-2-oxoethyl] L-proline (54 mg, 0.17 mmol, 1.0 eq), N-ethylmorpholine (133 uL, 1.04 mmol, 6 eq) in acetonitrile (0.5 mL) was cooled to 0° C. and treated with a 50% solution of 1-n-propylphosphonic acid cyclic anhydride in dichloromethane (180 uL, 0.27 mmol, 1.6 eq) followed by the L-methionine benzylamide (71.36 mg, 0.30 mmol, 1.7 eq). Purification by HPLC provided 35 mg (38%) of L-methionine, N-[1-(2-(biphenyl-4-yl)-2-oxoethyl)-L-prolyl] benzylamide.

Rf 50% ethyl acetate in hexane)=0.40

HRMS calcd for $(M+H)^+$ $[(C_{31}H_{35}N_3O_3S+H)^+]$ ion 530.711; found 530.2480

EXAMPLE 55

Glycine, N-[1-(2-Adamantan-1-yl-2-Oxoethyl)-L-Prolyl] Benzylamide

Using the procedure described in example 3, a solution of 1-(2-adamantan-1-yl-2-oxoethyl) L-proline (104.6 mg, 0.36 mmol, 1.0 eq), triethylamine (150 uL, 1.07 mmol, 3.0 eq), and THF (1.5 mL), was treated with isobutyl chloroformate (51 uL, 0.39 mL, 1.1 eq), then with glycine N-benzylamide (88.2 mg, 537 umol, 1.5 eq). Workup as before provided 53.9 mg (34%) of glycine, N-[1-(2-adamantan-1-yl-2-oxoethyl)-L-prolyl] benzylamide. as a white foam.

$R_f$ (50% ethyl acetate in dichloromethane)=0.22

EXAMPLE 56

L-Valine, N-[1-(2-Adamantan-1-yl-2-Oxoethyl)-L-Prolyl] Benzylamide

Using the procedure described in Example 3, a solution of 1-(2-adamantan-1-yl-2-oxoethyl) L-proline (109.1 mg, 0.37 mmol, 1.0 eq), triethylamine (156 uL, 1.12 mmol, 3.0 eq), and THF (1.5 mL), was treated with isobutyl chloroformate (53 uL, 0.41 mL, 1.1 eq), then with L-valine benzylamide (117.5 mg, 570 umol, 1.5 eq). Workup as before provided 127 mg (71%) of L-valine, N-[1-(2-adamantan-1-yl-2-oxoethyl)-L-prolyl] benzylamide as a white foam.

$R_f$ (50% ethyl acetate in dichloromethane)=0.40

EXAMPLE 57

L-Leucine, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (108 mg, 0.37 mmol, 1.0 eq), triethylamine (156 uL, 1.11 mmol, 3.0 eq), and THF (1.5 mL), was treated with isobutyl chloroformate (53 uL, 0.41 mL, 1.1 eq), then with L-leucine N-benzylamide (123 mg, 570 umol, 1.5 eq). Workup as before provided 124 mg (68%) of L-leucine, N-[1-(2-adamantan-1-yl-2-oxoethyl)-L-prolyl] benzylamide.

$R_f$ (50% ethyl acetate in dichloromethane)=0.48

EXAMPLE 58

L-Phenylalanine, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (100 mg, 0.34 mmol, 1.0 eq), L-phenylalanine N-benzylamide (175 mg, 686 umol, 2.0 eq) and dichloromethane (1.0 mL), was cooled to 0° C., and treated with triethylamine (286 uL, 2.0 mmol, 6.0 eq). To this chilled solution was added a 50% solution of 1-n-propylphosphonic acid cyclic anhydride in dichloromethane (436 uL, 0.68 mL, 2.0 eq). When TLC indicated the reaction was complete, the solution was allowed to warm to 22° C., washed with satd aq NaHCO$_3$, concentrated in vacuo, and purified by flash chromatography to provide 144 mg (80%) of L-phenylalanine, N-[1-(2-adamantan-1-yl-2-oxoethyl)-L-prolyl] benzylamide.

$R_f$ (50% ethyl acetate in dichloromethane)=0.36

EXAMPLE 59

L-Norvaline, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (155 mg, 0.53 mmol, 1.0 eq), L-norvaline N-benzylamide (220 mg, 1.07 mmol, 2.0 eq) and dichloromethane (1.0 mL), was treated with triethylamine (446 uL, 3.2 mmol, 6.0 eq), and a 50% solution of 1-n-propylphosphonic acid cyclic anhydride in dichloromethane (680 uL, 1.07 mL, 2.0 eq), to provide 372 mg (70%) of L-norvaline, N-[1-(2-adamantan-1-yl-2-oxoethyl)-L-prolyl] benzylamide.

EXAMPLE 60

L-Norleucine, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (154 mg, 0.53 mmol, 1.0 eq), L-norleucine N-benzylamide (234 mg, 1.07 mmol, 2.0 eq) and dichloromethane (1.0 mL), was treated with triethylamine (446 uL, 3.2 mmol, 6.0 eq), and a 50% solution of 1-n-propylphosphonic acid cyclic anhydride in dichloromethane (680 uL, 1.07 mL, 2.0 eq), to provide 210 mg (80%) of L-norleucine, N-[1-(2-adamantan-1-yl-2-oxoethyl)-L-Prolyl] benzylamide as a white foam.

$R_f$ (50% ethyl acetate in dichloromethane)=0.44

EXAMPLE 61

L-Asparagine, N-[1-(2-Adamantan-1-yl-2-Oxoethyl)-L-Prolyl] Benzylamide

Using the procedure described previously, a heterogeneous solution of 1-(2-adamantan-1-yl-2-oxoethyl) L-proline (152 mg, 0.52 mmol, 1.0 eq), L-asparagine N-benzylamide (231 mg, 1.04 mmol, 2.0 eq) and dichloromethane (1.5 mL), was treated with triethylamine (436 uL, 3.1 mmol, 6.0 eq), and a 50% solution of 1-n-propylphosphonic acid cyclic anhydride in dichloromethane (663 uL, 1.04 mL, 2.0 eq), to provide 130.7 mg (51%) of L-asparagine, N-[1-(2-adamantan-1-yl-2-oxoethyl)-L-prolyl] benzylamide as a white foam.

$R_f$ (10% MeOH in dichloromethane)=0.41

EXAMPLE 62

L-Serine-(O-Benzyl Ether), N-[1-(2-Adamantan-1-yl-2-Oxoethyl)-L-Prolyl] Benzylamide Using the procedure described previously, a solution of 1-(2-adamantan-1-yl-2-oxoethyl)L-proline (151 mg, 0.52 mmol, 1.0 eq), L-serine-(O-benzyl ether)-N-benzylamide (294 mg, 1.03 mmol, 2.0 eq) and dichloromethane (1.5 mL), was treated with triethylamine (432 uL, 3.1 mmol, 6.0 eq), and a 50% solution of 1-n-propylphosphonic acid cyclic anhydride in dichloromethane (658 uL, 2.0 eq), to provide 220 mg (76%) of L-serine-(O-benzyl ether), N-[1-(2-adamantan-1-yl-2-oxoethyl)-L-prolyl] benzylamide.

$R_f$ (50% ethyl acetate in dichloromethane)=0.30

EXAMPLE 63

L-β-Phenylalanine, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (154 mg, 0.53 mmol, 1.0 eq), L-β-phenylalanine N-benzylamide (286 mg, 1.06 mmol, 2.0 eq) and dichloromethane (1.5 mL), was treated with triethylamine (442 uL, 3.2 mmol, 6.0 eq), and a 50% solution of 1-n-propylphosphonic acid cyclic anhydride in dichloromethane (673 uL, 2.0 eq), to provide 229 mg (81%) of L-β-phenylalanine, N-[1-(2-adamantan-1-yl-2-oxoethyl)-L-prolyl] benzylamide.

$R_f$ (50% ethyl acetate in dichloromethane)=0.40

EXAMPLE 64

L-Cyclohexylalanine, N-[1-(2-Adamantan-1-yl-2-Oxoethyl)-L-Prolyl] Benzylamide

Using the procedure described previously, a solution of 1-(2-adamantan-1-yl-2-oxoethyl) L-proline (155 mg, 0.53 mmol, 1.0 eq), L-cyclohexylalanine N-benzylamide (248 mg) and dichloromethane (1.5 mL), was treated with triethylamine (444 uL, 3.2 mmol, 6.0 eq), and a 50% solution of 1-n-propylphosphonic acid cyclic anhydride in dichloromethane (676 uL, 2.0 eq), to provide 148 mg (52%) of L-cyclohexylalanine, N-[1-(2-adamantan-1-yl-2-oxoethyl)-L-prolyl] benzylamide.

$R_f$ (50% ethyl acetate in dichloromethane)=0.42

EXAMPLE 65

L-Isoleucine, N-[1-(2-Adamantan-1-yl-2-Oxoethyl)-L-Prolyl] alpha-(S)-methylbenzylamide Using the procedure described previously, a solution of 1-(2-adamantan-1-yl-2-oxoethyl) L-proline (154 mg, 0.53 mmol, 1.0 eq), L-isoleucine alpha-(S)-methylbenzylamide (247 mg, 1.05 mmol) and dichloromethane (1.5 mL), was treated with triethylamine (441 uL, 3.2 mmol, 6.0 eq), and a 50% solution of 1-n-propylphosphonic acid cyclic anhydride in dichloromethane (671 uL, 2.0 eq), to provide 192 mg (72%) of L-isoleucine, N-[1-(2-adamantan-1-yl-2-oxoethyl)-L-prolyl] alpha-(S)-methyl-benzylamide.

$R_f$ (50% ethyl acetate in dichloromethane)=0.44

EXAMPLE 66

L-Isoleucine, N-[1-(2-Adamantan-1-yl-2-Oxoethyl)-L-Prolyl] alpha-(R)-methylbenzylamide Using the procedure described previously, a solution of 1-(2-adamantan-1-yl-2-oxoethyl) L-proline (146 mg, 0.53 mmol, 1.0 eq), L-isoleucine alpha-(R)-methylbenzylamide (234 mg, 1.05 mmol) and dichloromethane (1.5 mL), was treated with triethylamine (420 uL, 6.0 eq), and a 50% solution of 1-n-propylphosphonic acid cyclic anhydride in dichloromethane (638 uL, 2.0 eq), to provide 108 mg (43%) of L-isoleucine, N-[1-(2-adamantan-1-yl-2-oxoethyl)-L-prolyl] alpha-(R)-methylbenzylamide.

$R_f$ (15% methanol in dichloromethane)=0.47

EXAMPLE 67

L-Isoleucine, N-[1-(2-Adamantan-1-yl-2-Oxoethyl)-L-Prolyl] Pyridin-4-ylmethylamide Using the procedure described previously, a solution of 1-(2-adamantan-1-yl-2-oxoethyl) L-proline (230 mg, 0.78 mmol, 1.0 eq), L-isoleucine pyridin-4-ylmethylamide (266 mg, 1.5 mmol) and dichloromethane (2 mL), was treated with triethylamine (660 uL, 6.0 eq), and a 50% solution of 1-n-propylphosphonic acid cyclic anhydride in dichloromethane (1.0 mL, 2.0 eq), to provide 180 mg (46%) of L-isoleucine, N-[1-(2-adamantan-1-yl-2-oxoethyl)-L-prolyl] pyridin-4-ylmethylamide.

$R_f$ (4% methanol in dichloromethane)=0.23

EXAMPLE 68

L-Isoleucine, N-[1-(2-Adamantan-1-yl-2-Oxoethyl)-L-Prolyl] Pyridin-2-ylmethylamide Using the procedure described previously, a solution of 1-(2-adamantan-1-yl-2-oxoethyl) L-proline (165 mg, 0.56 mmol, 1.0 eq), L-isoleucine pyridin-2-ylmethylamide (246 mg, 1.11 mmol) and dichloromethane (2 mL), was treated with triethylamine (475 uL, 6.0 eq), and a 50% solution of 1-n-propylphosphonic acid cyclic anhydride in dichloromethane (721 uL, 2.0 eq), to provide 214 mg (77%) of L-isoleucine, N-[1-(2-adamantan-1-yl-2-oxoethyl)-L-prolyl] pyridin-2-ylmethylamide.

$R_f$ (5% methanol in dichloromethane)=0.21

EXAMPLE 69

L-Isoleucine, N-[1-(2-Adamantan-1-yl-2-Oxoethyl)-L-Prolyl] 4-methoxybenzylamide

Using the procedure described previously, a solution of 1-(2-adamantan-1-yl-2-oxoethyl) L-proline (140 mg, 0.48 mmol, 1.0 eq), L-isoleucine 4-methoxybenzylamide (238 mg, 0.95 mmol) and dichloromethane (2 mL), was treated with triethylamine (400 uL, 6.0 eq), and a 50% solution of 1-n-propylphosphonic acid cyclic anhydride in dichloromethane (610 uL, 2.0 eq), to provide 207 mg (82%) of L-isoleucine, N-[1-(2-adamantan-1-yl-2-oxoethyl)-L-prolyl] 4-methoxybenzylamide.

$R_f$ (50% ethyl acetate in dichloromethane)=0.31

EXAMPLE 70

L-Isoleucine, N-[1-(2-Adamantan-1-yl-2-Oxoethyl)-L-Prolyl] 2-methoxybenzylamide

Using the procedure described previously, a solution of 1-(2-adamantan-1-yl-2-oxoethyl) L-proline (179 mg, 0.61 mmol, 1.0 eq), L-isoleucine 2-methoxybenzylamide (308 mg, 1.23 mmol) and dichloromethane (2 mL), was treated with triethylamine (515 uL, 6.0 eq), and a 50% solution of 1-n-propylphosphonic acid cyclic anhydride in dichloromethane (783 uL, 2.0 eq), to provide 254 mg (79%) of L-isoleucine, N-[1-(2-adamantan-1-yl-2-oxoethyl)-L-prolyl] 2-methoxybenzylamide.

$R_f$ (50% ethyl acetate in dichloromethane)=0.31

EXAMPLE 71

L-Isoleucine, N-[1-(Carboxymethyl)-L-Prolyl] Benzylamide

Using the hydrogenation conditions described in example 4, a solution of L-isoleucine, N-[1-(2-benzyloxy-2-oxoethyl)-L-prolyl] benzylamide (14.80 g, 31.76 mmol), 10% palladium on carbon (0.80 g), and methanol (350 mL), was purged with hydrogen, and stirred under an atmosphere of hydrogen at 22° C. After 8 hrs, the solution was purged with argon, filtered through a plug of celite, and concentrated in vacuo to provide 11.47 g, (96%) of L-isoleucine, N-[1-(carboxymethyl)-L-prolyl] benzylamide as a white solid.

mp=76°–80° C.

$R_f$ (100% ethyl acetate)=0.04

Mass Spectrum (EI) m/e (rel intensity) 376 (20, M+H), 307 (38), 154 (100), 136 (82).

EXAMPLE 72

General Procedure for Attachment of Y-R4 Groups.
L-Isoleucine, N-[1-[2-[N-(Piperidine-3-Carboxylic Acid Ethyl Ester)]-2-Oxoethyl]-L-Prolyl] Benzylamide A –5° C. solution of L-isoleucine, N-[1-(carboxymethyl)-L-prolyl] benzylamide (266 mg, 0.71 mmol, 1.0 eq), N-ethylmorpholine (135 uL, 1.06 mmol, 1.5 eq) in acetonitrile (5.0 mL) was treated with isobutyl chloroformate (101 uL, 0.78 mmol, 1.1 eq) followed by ethyl nipecotate (220 uL, 1.40 mmol, 2.0 eq). Purification by flash chromatography provided 150 mg (41%) of L-isoleucine, N-[1-[2-[N-(piperidine-3-carboxylic acid ethyl ester)]-2-oxoethyl]-L-prolyl] benzylamide as a colorless oil.

$R_f$ (100% ethyl acetate)=0.22

EXAMPLE 73

L-Isoleucine, N-[1-(2-(1,4-Dioxa-8-aza-spiro[4.5]dec-8-yl)-2-Oxoethyl)-L-Prolyl] Benzylamide A –5° C. solution of L-isoleucine, N-[1-(carboxymethyl)-L-prolyl] benzylamide (254 mg, 0.67 mmol, 1.0 eq), N-methylmorpholine (96 uL, 0.88 mmol, 1.30 eq) in acetonitrile (7 mL) was treated with isobutyl chloroformate (96 uL, 0.74 mmol, 1.1 eq) followed by 1,4-dioxa-8-aza-spiro [4.5] decane (0.193 g, 1.35 mmol, 2.0 eq). Purification by flash chromatography provided 280 mg (83%) of L-isoleucine, N-[1-(2-(1,4-dioxa-8-aza-spiro[4.5]dec-8-yl)-2-oxoethyl)-L-Prolyl] benzylamide as a colorless oil $R_f$ (100% ethyl acetate)=0.13

$R_f$ (20% MeOH in ethyl acetate)=0.68

Mass Spectrum (+EI) m/e (rel intensity) 500 (10, M+), 330 (12), 253 (100), 142 (18).

EXAMPLE 74

L-Isoleucine, N-[1-[2-(N-(4-Benzylpiperidyl))-2-Oxoethyl]-L-Prolyl] Benzylamide

A –5° C. solution of L-isoleucine, N-[1-(carboxymethyl)-L-prolyl] benzylamide (321 mg, 0.85 mmol, 1.0 eq), N-methylmorpholine (122 uL, 1.11 mmol, 1.30 eq) in acetonitrile (8 mL) was treated with isobutyl chloroformate (127 uL, 0.98 mmol, 1.15 eq) followed by 4-benzylpiperidine (0.299 g, 1.71 mmol, 2.0 eq). Purification by flash chromatography provided 401 mg (88%) of L-isoleucine, N-[1-[2-(N-(4-benzylpiperidyl))-2-oxoethyl]-L-prolyl] benzylamide as a colorless oil.

$R_f$ (100% ethyl acetate)=0.29

$R_f$ (20% MeOH in ethyl acetate)=0.69

Mass Spectrum (+CI) m/e (rel intensity) 532 (70, M+), 425 (30), 357 (22), 330 (100).

EXAMPLE 75

L-Isoleucine, N-[1-[2-(2-Methylpiperidine)-2-Oxoethyl]-L-Prolyl] Benzylamide

A –5° C. solution of L-isoleucine, N-[1-(carboxymethyl)-L-prolyl] benzylamide (202 mg, 0.53 mmol, 1.0 eq), N-ethylmorpholine (82 uL, 0.64 mmol, 1.20 eq) in acetonitrile (8 mL) was treated with isobutyl chloroformate (80 uL, 0.62 mmol, 1.15 eq) followed by 2-methylpiperidine (0.106 g, 1.07 mmol, 2.0 eq). The solution was warmed to 22° C., concentrated to a residue, and purified by flash chromatography to provide 80 mg (32%) of L-isoleucine, N-[1-[2-(N-(2-methylpiperidine))-2-oxoethyl]-L-prolyl] benzylamide as a colorless oil.

$R_f$ (100% ethyl acetate)=0.26

$R_f$ (20% MeOH in ethyl acetate)=0.61

Mass Spectrum (+EI) m/e (rel intensity) 456 (10, M+), 330 (14), 209 (100), 82 (82)

EXAMPLE 76

L-Isoleucine, N-[1-(2-(2-Hydroxyethylamine)-2-Oxoethyl)-L-Prolyl] Benzylamide

A –5° C. solution of L-isoleucine, N-[1-(carboxymethyl)-L-prolyl] benzylamide (0.215 g, 0.58 mmol, 1.0 eq), and triethylamine (96 uL, 70 mg, 0.64 mmol, 1.20 eq), in acetonitrile (10 mL) was treated with isobutyl chloroformate (83 uL, 86 mg, 0.63 mmol, 1.1 eq) followed by 2-aminoethanol (69 uL, 70 mg, 1.15 mmol, 2.0 eq). Workup as above provided 127 mg (53%) of L-isoleucine, N-[1-(2-(2-hydroxyethylamine)-2-oxoethyl)-L-prolyl] benzylamide.

$R_f$ (100% ethyl acetate)=0.05

Mass Spectrum (+EI) m/e (rel intensity) 418 (10, M+), 330 (10), 171 (100), 153 (30).

EXAMPLE 77

L-Isoleucine, N-[1-[2-(4-Phenylpiperazine)-2-Oxoethyl]-L-Prolyl] Benzylamide

A −5° C. solution of L-isoleucine, N-[1-(carboxymethyl)-L-prolyl] benzylamide (0.214 g, 0.58 mmol, 1.0 eq), and triethylamine (96 uL, 70 mg, 0.64 mol, 1.20 eq), in acetonitrile (6 mL) was treated with isobutyl chloroformate (83 uL, 86 mg, 0.63 mmol, 1.1 eq) followed by 4-phenylpiperazine (170 uL, 186 mg, 1.15 mmol, 2.0 eq). Workup as above provided 170 mg (57%) of L-isoleucine, N-[1-[2-(4-phenylpiperazine)-2-oxoethyl]-L-prolyl] benzylamide.

$R_f$ (100% ethyl acetate)=0.18

Mass Spectrum (+EI) m/e (rel intensity) 519 (30, M+), 330 (22), 272 (100), 161 (20), 136 (25).

EXAMPLE 78

L-Isoleucine, N-[1-[2-(1-Pyrrolidine)-2-Oxoethyl]-L-Prolyl] Benzylamide

A −5° C. solution of L-isoleucine, N-[1-(carboxymethyl)-L-prolyl] benzylamide (0.212 g, 0.56 mmol, 1.0 eq), and triethylamine (96 uL, 65 mg, 0.65 mmol, 1.15 eq), in acetonitrile (10 mL) was treated with isobutyl chloroformate (77 uL, 80 mg, 0.59 mmol, 1.05 eq) followed by pyrrolidine (94 uL, 80 mg, 1.13 mmol, 2.0 eq). Workup as above provided 205 mg (85%) of L-isoleucine, N-[1-[2-(1-pyrrolidine)-2-oxoethyl]-L-prolyl] benzylamide.

$R_f$ (100% ethyl acetate)=0.14

Mass Spectrum (+EI) m/e (rel intensity) 428 (13, M+), 330 (10), 208 (10), 181 (100), 82 (85).

EXAMPLE 79

L-Isoleucine, N-[1-[2-(N-Cyclopentylamino)-2-Oxoethyl]-L-Prolyl] Benzylamide

A −5° C. solution of L-isoleucine, N-[1-(carboxymethyl)-L-prolyl] benzylamide (0.212 g, 0.56 mmol, 1.0 eq), and triethylamine (96 uL, 65 mg, 0.65 mol, 1.15 eq), in acetonitrile (10 mL) was treated with isobutyl chloroformate (77 uL, 86 mg, 0.59 mmol, 1.05 eq) followed by cyclopentylamine (111 uL, 96 mg, 1.13 mmol, 2.0 eq). Workup as above provided 198 mg (79%) of L-isoleucine, N-[1-[2-(N-cyclopentylamino)-2-oxoethyl]-L-prolyl] benzylamide.

$R_f$ (100% ethyl acetate)=0.22

$R_f$ (20% MeOH in ethyl acetate)=0.55

Mass Spectrum (+EI) m/e (rel intensity) 442 (28, M+), 375 (11), 330 (35), 297 (28), 212 (100).

EXAMPLE 80

L-Isoleucine, N-[1-[2-(N-(Phenylmethylamino))-2-Oxoethyl]-L-Prolyl] Benzylamide

A −5° C. solution of L-isoleucine, N-[1-(carboxymethyl)-L-prolyl] benzylamide (0.218 g, 0.58 mmol, 1.0 eq), and triethylamine (89 uL, 64 mg, 0.64 mmol, 1.10 eq), in acetonitrile (10 mL) was treated with isobutyl chloroformate (79 uL, 83 mg, 0.61 mmol, 1.05 eq) followed by benzylamine (82 uL, 80 mg, 0.75 mmol, 1.3 eq). After the addition was complete, the flask was removed from the cold bath and the solution was stirred at 22° C. for 3 hrs. Workup as above provide 227 mg (84%) of L-isoleucine, N-[1-[2-(N-(phenylmethylamino))-2-oxoethyl]-L-prolyl] benzylamide as a white solid.

mp=76°–80° C.

$R_f$ (100% ethyl acetate)=0.25

EXAMPLE 81

L-Isoleucine, N-[1-[2-(N-(Cyclohexylmethylamino))-2-Oxoethyl]-L-Prolyl] Benzylamide Using the procedure described previously, a solution of L-isoleucine, N-[1-(carboxymethyl)-L-prolyl] benzylamide (0.220 g, 0.58 mmol, 1.0 eq), and triethylamine (89 uL, 64 mg, 0.64 mmol, 1.10 eq), in acetonitrile (10 mL) was treated with isobutyl chloroformate (79 uL, 83 mg, 0.61 mmol, 1.05 eq) followed by cyclohexylmethylamine (99 uL, 86 mg, 0.75 mmol, 1.30 eq). Workup as above provided 201 mg (73%) of L-isoleucine, N-[1-[2-(N-(cyclohexylmethylamino))-2-oxoethyl]-L-prolyl] benzylamide.

$R_f$ (100% ethyl acetate)=0.23

$R_f$ (20% MeOH in ethyl acetate)=0.64

EXAMPLE 82

L-Isoleucine, N-[1-(2-(4-Phenylpiperidyl)-2-Oxoethyl)-L-Prolyl] Benzylamide

Using the procedure described above, a solution of L-isoleucine, N-[1-(carboxymethyl)-L-prolyl] benzylamide (0.124 g, 0.33 mmol, 1.0 eq), and N-methylmorpholine (43 uL, 40 mg, 0.40 mmol, 1.20 eq), in acetonitrile (3 mL) was treated with isobutyl chloroformate (45 uL, 47 mg, 0.35 mmol, 1.05 eq) followed by 4-phenylpiperidine (69 mg, 0.43 mmol, 1.3 eq). Workup as above provided 101 mg (59%) of L-isoleucine, N-[1-(2-(4-phenylpiperidyl)-2-oxoethyl)-L-prolyl] benzylamide.

$R_f$ (100% ethyl acetate)=0.18

EXAMPLE 83

L-Isoleucine, N-[1-(2-[1-(3,7,11-Trimethyldodeca-2,6,10-trien-1-ol)]-2-Oxoethyl)-L-Proline] Benzylamide A solution of L-isoleucine, N-[1-(carboxymethyl)-L-prolyl] benzylamide (67 mg, 0.18 mmol), 4-N,N-dimethylaminopyridine (6.1 mg, 0.05 mmol, 0.3 eq), 1,3-dicyclohexylcarbodiimide (64 mg, 0.31 mmol, 1.8 eq) in dichloromethane (2.0 mL) was treated with trans,trans farnesol (55 uL, 0.22 mmol, 1.2 eq). After TLC indicated the reaction was complete, the mixture was purified by HPLC to provide 27 mg (26%) of L-isoleucine, N-[1-(2-[1-(3,7,11-trimethyldodeca-2,6,10-trien-1-ol)]-2-oxoethyl)-L-proline] benzylamide.

$R_f$ (50% ethyl acetate in dichloromethane)=0.50

HRMS calcd for $(M+H)^+$ $[(C_{35}H_{53}N_3O_4+H)^+]$ ion 580.8365; found 580.4117

EXAMPLE 84

L-Isoleucine, N-[1-(2-(3-Phenyl-2-Propen-1-Oxy)-2-Oxoethyl)-L-Prolyl] Benzylamide Using the procedure described previously, a solution of L-isoleucine, N-[1-(carboxymethyl)-L-prolyl] benzylamide (65 mg, 0.17 mmol), 4-N,N-dimethylaminopyridine (12.5 mg, 0.10 mmol, 0.6 eq), 1,3-dicyclohexylcarbodiimide (64 mg, 0.31 mmol, 1.8 eq) in dichloromethane (5.0 mL) was treated with trans cinnamyl alcohol (29 uL, 0.22 mmol, 1.3 eq). After TLC indicated the reaction was complete, the mixture was purified by HPLC to provide 32 mg (38%) of L-isoleucine, N-[1-(2-(3-phenyl-2-propen-1-oxy)-2-oxoethyl)-L-prolyl] benzylamide.

$R_f$ (50% ethyl acetate in dichloromethane)=0.47

HRMS calcd for $(M+H)^+$ $[(C_{29}H_{38}N_3O_4+H)^+]$ ion 492.6424; found 492.2864

EXAMPLE 85

L-Isoleucine, N-[1-(2-(3-Phenyl-3-Methyl-2-Propen-1-Oxy)-2-Oxoethyl)-L-Prolyl] Benzylamide Using the procedure described previously, a solution of L-isoleucine, N-[1-(carboxymethyl)-L-prolyl] benzylamide (56 mg, 0.15 mmol), 4-N,N-dimethylaminopyridine (3.6 mg, 0.03 mmol, 0.2 eq), 1,3-dicyclohexylcarbodiimide (54 mg, 0.26 mmol, 1.7 eq) in dichloromethane (5.0 mL) was treated with trans 2-methyl-3-phenyl-2-propen-1-ol (28 uL, 0.19 mmol, 1.3 eq). After TLC indicated the reaction was complete, the mixture was purified by HPLC to provide 32 mg (42%) of L-isoleucine, N-[1-(2-(3-phenyl-3-methyl-2-Propen-1-oxy)-2-oxoethyl)-L-prolyl] benzylamide.

$R_f$ (50% ethyl acetate in dichloromethane)=0.52

HRMS calcd for $(M+H)^+$ $[(C_{30}H_{40}N_3O_4+H)^+]$ ion 506.6695; found 506.3021

EXAMPLE 86

L-Isoleucine, N-[1-(2-(1-Phenylpropoxy)-2-Oxoethyl)-L-Prolyl] Benzylamide

A solution of L-isoleucine, N-[1-(carboxymethyl)-L-prolyl] benzylamide (59 mg, 0.16 mmol), 4-N,N-dimethylaminopyridine (7.9 mg, 0.06 mmol, 0.4 eq), 1,3-dicyclohexylcarbodiimide (49 mg, 0.23 mmol, 1.5 eq) in dichloromethane (5.0 mL) was treated with (±) 1-phenyl-1-propanol (28 uL, 0.20 mmol, 1.3 eq). After TLC indicated the reaction was complete, the mixture was purified by HPLC to provide 32 mg (41%) of L-isoleucine, N-[1-(2-(1-phenylpropoxy)-2-oxoethyl)-L-prolyl] benzylamide.

$R_f$ (50% ethyl acetate in dichloromethane)=0.51

HRMS calcd for $(M+H)^+$ $[(C_{29}H_{40}N_3O_4+H)^+]$ ion 494.6584; found 494.3021

EXAMPLE 87

L-Isoleucine, N-[1-(2-(1-Phenyl-1-Cyclohexylmethoxy)-2-Oxoethyl)-L-Prolyl] Benzylamide Using the procedure described previously, a solution of L-isoleucine, N-[1-(carboxymethyl)-L-prolyl] benzylamide (71 mg, 0.19 mmol), 4-N,N-dimethylaminopyridine (7.5 mg, 0.06 mmol, 0.3 eq), 1,3-dicyclohexylcarbodiimide (64 mg, 0.31 mmol, 1.6 eq) in dichloromethane (5.0 mL) was treated with (±) cyclohexylphenylcarbinol (45 mg, 0.24 mmol, 1.3 eq). After TLC indicated the reaction was complete, the mixture was purified by HPLC to provide 27 mg (26%) of L-isoleucine, N-[1-(2-(1-phenyl-1-cyclohexylmethoxy)-2-oxoethyl)-L-prolyl] benzylamide (RD-08-71, Z6338).

$R_f$ (50% ethyl acetate in dichloromethane)=0.51

HRMS calcd for $(M+H)^+$ $[(C_{33}H_{46}N_3O_3+H)^+]$ ion 548.7506; found 548.3491

EXAMPLE 88

L-Isoleucine, N-[1-(2-(1-Phenyl-2-(4-Morpholino)Ethoxy)-2-Oxoethyl)-L-Prolyl] Benzylamide Using the procedure described previously, a solution of L-isoleucine, N-[1-(carboxymethyl)-L-prolyl] benzylamide (58 mg, 0.15 mmol), 4-N,N-dimethylaminopyridine (13.2 mg, 0.10 mmol, 0.7 eq), 1,3-dicyclohexylcarbodiimide (57 mg, 0.27 mmol, 1.8 eq) in dichloromethane (5.0 mL) was treated with (±) alpha-phenyl-4-morpholinoethanol (60 mg, 0.29 mmol, 1.9 eq). After TLC indicated the reaction was complete, the mixture was purified by HPLC to provide 20 mg (22%) of L-isoleucine, N-[1-(2-(1-phenyl-2-(4-morpholino)ethoxy)-2-oxoethyl)-L-prolyl] benzylamide.

$R_f$ (50% ethyl acetate in dichloromethane)=0.32

EXAMPLE 89

L-Isoleucine, N-[1-(2-(2-Oxy-2-Methyladamant-2-yl)-2-Oxoethyl)-L-Prolyl] Benzylamide Using the procedure described previously, a solution of L-isoleucine, N-[1-(carboxymethyl)-L-prolyl] benzylamide (61 mg, 0.16 mmol), 4-N,N-dimethylaminopyridine (26 mg, 0.21 mmol, 1.3 eq), 1,3-dicyclohexylcarbodiimide (51 mg, 0.25 mmol, 1.5 eq) in dichloromethane (3.0 mL) was treated with 2-methyl-2-adamantanol (33 mg, 0.21 mmol, 1.3 eq). After TLC indicated the reaction was complete, the mixture was purified by HPLC to provide 20 mg (23%) of L-isoleucine, N-[1-(2-(2-oxy-2-methyladamant-2-yl)-2-oxoethyl)-L-prolyl] benzylamide (RD-08-73, Z6340).

$R_f$ (50% ethyl acetate in dichloromethane)=0.45

HRMS calcd for $(M+H)^+$ $[(C_{31}H_{46}N_3O_3+H)^+]$ ion 524.7284; found 524.3491

EXAMPLE 90

L-Isoleucine, N-[1-(Adamantan-2-ylcarbamoylmethyl)-L-Prolyl] Benzylamide

Using the procedure described previously, a solution of L-isoleucine, N-[1-(carboxymethyl)-L-prolyl] benzylamide (113 mg, 0.30 mmol), triethylamine (168 uL, 1.20 mmol, 4 eq) in acetonitrile (1.5 mL, was cooled to 0° C. and treated with isobutyl chloroformate (43 uL, 0.33 mmol, 1.1 eq) followed by the hydrochloride salt of 2-adamantylamine (113.2 mg, 0.60 mmol, 2 eq). After TLC indicated the reaction was complete, the mixture was purified by HPLC to provide 10 mg (6.5%) of L-isoleucine, N-[1-(adamantan-2-ylcarbamoylmethyl)-L-prolyl] benzylamide.

$R_f$ (100% ethyl acetate)=0.26

EXAMPLE 91

L-Isoleucine, N-[1-(Adamant-1-ylmethylcarbamoylmethyl)-L-Prolyl] Benzylamide

Using the procedure described previously, a solution of L-isoleucine, N-[1-(carboxymethyl)-L-prolyl] benzylamide (106 mg, 0.28 mmol), triethylamine (158 uL, 1.13 mmol, 4 eq) in acetonitrile (1.5 mL, was cooled to 0° C. and treated with isobutyl chloroformate (40.5 uL, 0.31 mmol, 1.1 eq) followed by 1-adamantanemethylamine (100 uL, 0.57 mmol, 2 eq). After TLC indicated the reaction was complete, the mixture was purified by HPLC to provide 15 mg (10%) of L-isoleucine, N-[1-(adamant-1-ylmethylcarbamoylmethyl)-L-prolyl] benzylamide.

$R_f$ (100% ethyl acetate)=0.25

HRMS calcd for $(M+H)^+$ $[(C_{31}H_{47}N_4O_3+H)^+]$ ion 523.7436; found 523.3651

EXAMPLE 92

L-Isoleucine, N-[1-(2-(2-Methyl-1-(S)-Phenyl-1-Propoxy)-2-Oxoethyl)-L-Prolyl] Benzylamide Using the procedure described previously, a solution of L-isoleucine, N-[1-(carboxymethyl)-L-prolyl] benzylamide (298 mg, 0.73 mmol), 4-N,N-dimethylaminopyridine (95 mg, 0.77 mmol, 1.2 eq), 1,3-dicyclohexylcarbodiimide (243 mg, 1.18 mmol, 1.8 eq) in dichloromethane (10 mL) was treated with (S)-2-methyl-1-phenyl-1-propanol (100 mg, 0.64 mmol, 1.3 eq). After TLC indicated the reaction was complete, the mixture was purified by HPLC to provide 104 mg (32%) of L-isoleucine, N-[1-(2-(2-methyl-1-(S)-phenyl-1-propoxy)-2-oxoethyl)-L-prolyl] benzylamide.

$R_f$ (50% ethyl acetate in dichloromethane)=0.57

EXAMPLE 93

L-Isoleucine, N-[1-(2-(2-Methyl-1-(R)-Phenyl-1-Propoxy)-2-Oxoethyl)-L-Prolyl] Benzylamide Using the procedure described previously, a solution of L-isoleucine, N-[1-(carboxymethyl)-L-prolyl] benzylamide (298 mg, 0.73 mmol), 4-N,N-dimethylaminopyridine (100 mg, 0.82 mmol, 1.3 eq), 1,3-dicyclohexylcarbodiimide (242 mg, 1.17 mmol, 1.8 eq) in dichloromethane (10 mL) was treated with (R)-2-methyl-1-phenyl-1-propanol (100 mg, 0.64 mmol, 1.3 eq). After TLC indicated the reaction was complete, the mixture was purified by HPLC to provide 96.2 mg (30%) of L-isoleucine, N-[1-(2-(2-methyl-1-(R)-phenyl-1-propoxy)-2-oxoethyl)-L-prolyl] benzylamide.

$R_f$ (50% ethyl acetate in dichloromethane)=0.57

EXAMPLE 94

Preparation of 3-(4-(N-Carboallyloxy)aminophenyl) propanol

To a round bottomed flask equipped with a magnetic stirrer was added 4-nitrocinnamyl alcohol (2.0 g, 11.16 mmol), 10% Pd on carbon (200 mg) and absolute ethanol (150 mL). The solution was purged with hydrogen and stirred at 22° C. under a hydrogen atmosphere. When TLC indicated the reaction was complete (4 hr), the solution was purged with argon and filtered through Celite. The filtrate was concentrated in vacuo to provide 3-(4-aminophenyl) propanol, 1.72 g (>100%), as a viscous oil which solidified on standing.

$R_f$=0.17 (50% EtOAc in hexane).

To a round bottomed flask was added the 3-(4-aminophenyl)propanol (1.3 g, 8.6 mmol), pyridine (1.0 mL, 12 mmol) and dichloromethane (25 mL). The solution was cooled to 0° C. and treated with allyl chloroformate (1.0 mL, 9.4 mmol). After allowing to warm to 22° C. over 1 hour, the reaction mixture was diluted with dichloromethane and washed twice with 1N HCl, followed by sat. NaHCO$_3$, water and sat. aq. NaCl. The organic extract was dried (MgSO$_4$) and concentrated in vacuo. Purification by flash chromatography (50% EtOAc in hexane), provided 1.77 g (88%) of 3-(4-(N-carboallyloxy)aminophenyl)propanol as a clear oil which solidified on standing.

$R_f$=0.37 (60% EtOAc in hexane).

EXAMPLE 95

Preparation of trans 1-Phenyl-3-(S)-Amino-4-(S)-Methylhexa-1-ene

Into a 1-L round bottomed flask equipped with a magnetic stirrer was added diethyl benzylphosphonate (14.3 mL, 15.8 g, 69.37 mmol, 1.2 eq.) and THF (500 mL). The flask was purged with argon and cooled to −78° C. A 1M solution of NaN(SiMe$_3$)$_2$ in THF (74.1 mL, 74.1 mmol, 1.2 eq.) was added dropwise to the phosphonate, and the color changed from colorless to pale yellow.

After stirring 30 min at −78° C., a solution of Boc-L-isoleucinal (13.6 g, 63.1 mmol; prepared as described earlier: Saari et al., 1990, Synthesis, page 453) in THF (50 mL) was added dropwise. The reaction mixture was stirred at −78° C. for 30 min, then allowed to warm up to 0° C. over a 2 hour period. The solution was evaporated to dryness and the resulting colorless oil was dissolved in Et$_2$O (250 mL). The ether solution was washed with sat. aq. NH$_4$Cl (50 mL), sat. aq. NaCl (25 mL), dried (MgSO$_4$) and evaporated to a residue. The residue was purified by flash chromatography (5% EtOAc in hexane) to provide 8.7 g (48%) of the desired product as a colorless oil.

$R_f$=0.63 (30% EtOAc in hexane).

The alkene from above (8.7 g, 30.27 mmol) was dissolved in CH$_2$Cl$_2$ (50 mL) and treated with trifluoroacetic acid (20 mL). After 20 min stirring at 22° C., the reaction appeared complete (TLC). The reaction mixture was neutralized with excess sat. aq. NaHCO$_3$, washed with sat. aq. NaCl (20 mL), dried (MgSO$_4$) and evaporated to dryness. The resulting colorless oil was dissolved in Et$_2$O (100 mL) and extracted with 1N HCl (3×50 mL). The aqueous layer was neutralized with 1N NaOH and extracted with Et$_2$O (3×50 mL). The organic layer was dried (MgSO$_4$) and concentrated in vacuo to provide 2.8 g (50%) of trans 1-phenyl-3-(S)-amino-4-(S)-methylhexa-1-ene as a colorless oil that solidified on standing.

$R_f$=0.04 (30% EtOAc in hexane).

EXAMPLE 96

L-Isoleucine, N-[1-(2-(4-tert-Butylcyclohexyl)-2-Oxoethyl)-L-Prolyl] Benzylamide Using the procedure described in Example 5, treatment of L-proline-L-isoleucine benzylamide (200 mg, 0.63 mmol) with 4-(t-butyl)cyclohexyl α-chloromethyl ketone (164 mg, 0.76 mmol, 1.2 eq; prepared from 4-tert-butylcyclohexanecarboxylic acid by the method described in example 1), provided 160 mg of L-isoleucine, N-[1-(2-(4-tert-butylcyclohexyl)-2-oxoethyl)-L-prolyl] benzylamide as a white foam.

$R_f$=0.45 (50% EtOAc in CH$_2$Cl$_2$).

LSIMS=498 (mass calculated for C$_{30}$H$_{47}$N$_3$O$_3$=497.73).

EXAMPLE 97

L-Isoleucine, N-[1-(2-Bicyclo[2.2.1]hept-2-yl)-2-Oxoethyl)-L-Prolyl] Benzylamide Using the procedure described in Example 5, treatment of L-proline-L-isoleucine benzylamide (100 mg, 0.32 mmol) with 2-norbornyl α-chloromethyl ketone (82 mg, 0.48 mmol, 1.5 eq; prepared from 2-norbornanecarboxylic acid by the method described in Example 1) provided 69 mg of L-isoleucine, N-[1-(2-bicyclo[2.2.1]hept-2-yl)-2-oxoethyl)-L-prolyl] benzylamide.

$R_f$=0.28 (70% EtOAc in hexane).

LSIMS=454 (mass calculated for C$_{27}$H$_{39}$N$_3$O$_3$=453.63).

EXAMPLE 98

L-Isoleucine, N-[1-(2-(3,4,5-Trimethoxyphenyl)-2-Oxoethyl)-L-Prolyl] Benzylamide Using the procedure described in Example 5, treatment of L-proline-L-isoleucine benzylamide (100 mg, 0.32 mmol) with 3,4,5-trimethoxyphenyl α-chloromethyl ketone (116 mg, 0.47 mmol, 1.5 eq; prepared from 3,4,5-trimethoxybenzoic acid by the method described in example 1) provided 190 mg of L-isoleucine, N-[1-(2-(3,4,5-trimethoxyphenyl)-2-oxoethyl)-L-prolyl] benzylamide.

$R_f$=0.33 (50% EtOAc in CH$_2$Cl$_2$).

EXAMPLE 99

L-Isoleucine, N-[1-(2-(Chroman-2-yl)-2-Oxoethyl)-L-Prolyl] Benzylamide Hydrochloride Salt Using the procedure described in Example 5, treatment of L-proline-L-isoleucine benzylamide (200 mg, 0.63 mmol)

with benzopyranyl α-chloromethyl ketone (266 mg, 1.26 mmol, 2 eq; prepared from 3,4-dihydro-2H-1-benzopyran-2-carboxylic acid by the method described in Example 1) provided the amine which was treated with HCl in ether to provide 200 mg of the hydrochloride salt of L-isoleucine, N-[1-(2-(chroman-2-yl)-2-oxoethyl)-L-prolyl] benzylamide as a solid as a mixture of diastereomers.

$R_f$=0.38 (for free base: 80% EtOAc in hexane).

LSIMS [M-HCl]=491 (mass calculated for $C_{29}H_{37}N_3O_4$+ HCl=528.09).

EXAMPLE 100

L-Isoleucine, N-[1-(2-(Benzofuran-2-yl)-2-Oxoethyl)-L-Prolyl] Benzylamide Hydrochloride Salt Using the procedure described in Example 5, treatment of L-proline-L-isoleucine benzylamide (200 mg, 0.63 mmol) with benzofuranyl α-chloromethyl ketone (246 mg, 1.26 mmol, 2 eq; prepared from 2-benzofurancarboxylic acid by the method described in example 1) provided the amine which was treated with HCl in ether to provide 200 mg of the hydrochloride salt of L-isoleucine, N-[1-(2-(benzofuran-2-yl)-2-oxoethyl)-L-prolyl] benzylamide as a solid.

$R_f$=0.13 (for free base: 50% EtOAc in hexane).

LSIMS [M-HCl]=476 (mass calculated for $C_{28}H_{33}N_3O_4$+ HCl=512.05).

EXAMPLE 101

L-Isoleucine, N-[1-(2-(3-Benzoyloxyphenyl)-2-Oxoethyl)-L-Prolyl] Benzylamide

Using the procedure described in Example 5, treatment of L-proline-L-isoleucine benzylamide (200 mg, 0.63 mmol) with 3,-benzoyloxy-2-bromoacetophenone (302 mg, 0.95 mmol, 1.5 eq) provided 57 mg of L-isoleucine, N-[1-(2-(3-benzoyloxyphenyl)-2-oxoethyl)-L-Prolyl] benzylamide as a solid.

LSIMS=556 (mass calculated for $C_{33}H_{37}N_3O_5$=555.68).

EXAMPLE 102

L-Isoleucine, N-[1-(2-(4-Benzoyloxyphenyl)-2-Oxoethyl)-L-Prolyl] Benzylamide

Using the procedure described in Example 5, treatment of L-proline-L-isoleucine benzylamide (200 mg, 0.63 mmol) with 4'-benzoyloxy-2-bromoacetophenone (302 mg, 0.95 mmol, 1.5 eq) provided 171 mg of L-isoleucine, N-[1-(2-(4-benzoyloxyphenyl)-2-oxoethyl)-L-prolyl] benzylamide as a foam.

LSIMS=556 (mass calculated for $C_{33}H_{37}N_3O_5$=555.68).

EXAMPLE 103

L-Isoleucine, N-[1-(2-(2-Benzoyloxyphenyl)-2-Oxoethyl)-L-Prolyl] Benzylamide

Using the procedure described in Example 5, treatment of L-proline-L-isoleucine benzylamide (200 mg, 0.63 mmol) with 2'-benzoyloxy-2-bromoacetophenone (302 mg, 0.95 mmol, 1.5 eq) provided 120 mg of L-isoleucine, N-[1-(2-(2-benzoyloxyphenyl)-2-oxoethyl)-L-prolyl] benzylamide as a foam.

LSIMS=556 (mass calculated for $C_{33}H_{37}N_3O_5$=555.68).

EXAMPLE 104

L-Isoleucine, N-[1-(2-(3-Phenoxyphenyl)-2-Oxoethyl)-L-Prolyl] Benzylamide

Using the procedure described in Example 5, treatment of L-proline-L-isoleucine benzylamide (200 mg, 0.63 mmol) with 3'-phenoxy-2-chloroacetophenone (233 mg, 0.95 mmol, 1.5 eq; prepared from 3-phenoxybenzoic acid by the method described in Example 1) provided 80 mg of L-isoleucine, N-[1-(2-(3-phenoxyphenyl)-2-oxoethyl)-L-prolyl] benzylamide as a foam.

$R_f$=0.26 (70% EtOAc in hexane).

LSIMS=528 (mass calculated for $C_{32}H_{37}N_3O_4$=527.67).

EXAMPLE 105

L-Isoleucine, N-[1-(2-(2-Phenoxyphenyl)-2-Oxoethyl)-L-Prolyl] Benzylamide

Using the procedure described in Example 5, treatment of L-proline-L-isoleucine benzylamide (200 mg, 0.63 mmol) with 2'-phenoxy-2-chloroacetophenone (233 mg, 0.95 mmol, 1.5 eq; prepared from 2-phenoxybenzoic acid by the method described in Example 1) provided 40 mg of L-isoleucine, N-[1-(2-(2-phenoxyphenyl)-2-oxoethyl)-L-prolyl] benzylamide as a foam.

$R_f$=0.31 (70% EtOAc in hexane).

LSIMS=528 (mass calculated for $C_{32}H_{37}N_3O_4$=527.67).

EXAMPLE 106

L-Isoleucine, N-[1-(2-(3,4,5-Triethoxyphenyl)-2-Oxoethyl)-L-Prolyl] Benzylamide

Using the procedure described in Example 5, treatment of L-proline-L-isoleucine benzylamide (200 mg, 0.63 mmol) with 3,4,5-triethoxyphenyl α-chloromethyl ketone (271 mg, 0.95 mmol, 1.5 eq; prepared from 3,4,5-triethoxybenzoic acid by the method described in Example 1), provided 45 mg of L-isoleucine, N-[1-(2-(3,4,5-triethoxyphenyl)-2-oxoethyl)-L-prolyl] benzylamide as a foam.

$R_f$=0.19 (70% EtOAc in hexane).

LSIMS=568 (mass calculated for $C_{32}H_{45}N_3O_6$=567.73).

EXAMPLE 107

L-Isoleucine, N-[1-(2-(Benzo[1,3]dioxol-5-yl)-2-Oxoethyl)-L-Prolyl] Benzylamide

Using the procedure described in Example 5, treatment of L-proline-L-isoleucine benzylamide (200 mg, 0.63 mmol) with piperonyl α-chloromethyl ketone (188 mg, 0.95 mmol, 1.5 eq; prepared from piperonylic acid by the method described in Example 1), provided 84 mg of L-isoleucine, N-[1-(2-(benzo[1,3]dioxol-5-yl)-2-oxoethyl)-L-prolyl] benzylamide as a foam.

$R_f$=0.24 (70% EtOAc in hexane).

LSIMS=480 (mass calculated for $C_{27}H_{33}N_3O_5$=479.58).

EXAMPLE 108

L-Isoleucine, N-[1-{2-Oxo-2-[4-(2-Phenoxyethoxy)-Phenyl]-Ethyl}-L-Prolyl] Benzylamide Using the procedure described in Example 5, treatment of L-proline-L-isoleucine benzylamide (200 mg, 0.63 mmol) with 4'-phenoxyethoxy-2-chloroacetophenone, (275 mg, 0.95 mmol, 1.5 eq; prepared from 4-(2-phenoxyethoxy) benzoic acid by the method described in example 1), provided 80 mg of L-isoleucine, N-[1-{2-oxo-2-[4-(2-phenoxyethoxy)-phenyl]-ethyl}-L-prolyl] benzylamide as a crystalline solid.

LSIMS=572 (mass calculated for $C_{34}H_{41}N_3O_5$=571.72).

EXAMPLE 109

L-Isoleucine, N-[1-(2-(4-Phenoxyphenyl)-2-Oxoethyl)-L-Prolyl] Benzylamide

Using the procedure described in Example 5, treatment of L-proline-L-isoleucine benzylamide (200 mg, 0.63 mmol) with 4'-phenoxy-2-bromoacetophenone (275 mg, 0.95 mmol, 1.5 eq) provided 142 mg of L-isoleucine, N-[1-(2-(4-phenoxyphenyl)-2-oxoethyl)-L-prolyl] benzylamide as a foam.

LSIMS=528 (mass calculated for $C_{32}H_{37}N_3O_4$=527.67).

EXAMPLE 110

L-Isoleucine, N-[1-(2-(2,4,6-Trimethoxyphenyl)-2-Oxoethyl)-L-Prolyl] Benzylamide Using the procedure described in Example 5, treatment of L-proline-L-isoleucine benzylamide (200 mg, 0.63 mmol) with 2',4',6'-trimethoxyphenyl α-bromomethyl ketone (273 mg, 0.95 mmol, 1.5 eq) provided 88 mg of L-isoleucine, N-[1-(2-(2,4,6-trimethoxyphenyl)-2-oxoethyl)-L-prolyl] benzylamide.

LSIMS=526 (mass calculated for $C_{29}H_{39}N_3O_6$=525.65).

EXAMPLE 111

L-Isoleucine, N-[1-(2-(2,3-Dimethoxyphenyl)-2-Oxoethyl)-L-Prolyl] Benzylamide

Using the procedure described in Example 5, treatment of L-proline-L-isoleucine benzylamide (200 mg, 0.63 mmol) with 2',3'-dimethoxyphenyl α-chloromethyl ketone (190 mg, 0.88 mmol, 1.4 eq; prepared from 2,3-dimethoxybenzoic acid by the method described in Example 1) provided 34 mg of L-isoleucine, N-[1-(2-(2,3-dimethoxyphenyl)-2-oxoethyl)-L-prolyl] benzylamide.

LSIMS=496 (mass calculated for $C_{28}H_{37}N_3O_5$=495.62).

EXAMPLE 112

L-Isoleucine, N-[1-(2-(2,6-Dimethoxyphenyl)-2-Oxoethyl)-L-Prolyl] Benzylamide

Using the procedure described in Example 5, treatment of L-proline-L-isoleucine benzylamide (200 mg, 0.63 mmol) with 2',6'-dimethoxyphenyl α-bromomethyl ketone (326 mg, 1.26 mmol, 2.0 eq) provided 80 mg of L-isoleucine, N-[1-(2-(2,6-dimethoxyphenyl)-2-oxoethyl)-L-prolyl] benzylamide.

LSIMS=496 (mass calculated for $C_{28}H_{37}N_3O_5$=495.62).

EXAMPLE 113

L-Isoleucine, N-[1-(2-(1-(4-Methylphenyl)cyclohexyl)-2-Oxoethyl)-L-Prolyl] Benzylamide Using the procedure described in Example 5, treatment of L-proline-L-isoleucine benzylamide (200 mg, 0.63 mmol) with 1-(4-methylphenyl)cyclohexyl α-chloromethyl ketone (237 mg, 1.26 mmol, 2.0 eq; prepared from 1-(4-methylphenyl)-1-cyclohexanecarboxylic acid by the method described in example 1) provided 30 mg of L-isoleucine, N-[1-(2-(1-(4-methylphenyl) cyclohexyl)-2-oxoethyl)-L-prolyl] benzylamide.

LSIMS=532 (mass calculated for $C_{33}H_{45}N_3O_3$=531.74).

EXAMPLE 114

L-Isoleucine, N-[1-(2-(1-(4-Chlorophenyl)cyclohexyl)-2-Oxoethyl)-L-Prolyl] Benzylamide Using the procedure described in Example 5, treatment of L-proline-L-isoleucine benzylamide (200 mg, 0.63 mmol) with 1-(4-chlorophenyl)cyclohexyl α-chloromethyl ketone (342 mg, 1.26 mmol, 2.0 eq; prepared from 1-(4-chlorophenyl)-1-cyclohexanecarboxylic acid by the method described in Example 1) provided 30 mg of L-isoleucine, N-[1-(2-(1-(4-chlorophenyl) cyclohexyl)-2-oxoethyl)-L-prolyl] benzylamide.

LSIMS=552 (mass calculated for $C_{32}H_{42}ClN_3O_3$=552.16).

EXAMPLE 115

L-Isoleucine, N-[1-(2-(2,3,4-Trimethoxyphenyl)-2-Oxoethyl)-L-Prolyl] Benzylamide Using the procedure described in Example 5, treatment of L-proline-L-isoleucine benzylamide (200 mg, 0.63 mmol) with 2,3,4-trimethoxyphenyl α-bromomethyl ketone (273 mg, 0.95 mmol, 1.5 eq) provided 100 mg of L-isoleucine, N-[1-(2-(2,3,4-trimethoxyphenyl)-2-oxoethyl}-L-prolyl] benzylamide.

LSIMS=526 (mass calculated for $C_{29}H_{39}N_3O_6$=525.65).

EXAMPLE 116

L-Isoleucine, N-[1-(2-(1-Phenylcyclohexyl)-2-Oxoethyl)-L-Prolyl] Benzylamide

Using the procedure described in Example 5, treatment of L-proline-L-isoleucine benzylamide (200 mg, 0.63 mmol) with 1-phenylcyclohexyl α-chloromethyl ketone (224 mg, 0.95 mmol, 1.5 eq; prepared from 1-phenyl-1-cyclohexanecarboxylic acid by the method described in example 1) provided 40 mg of L-isoleucine, N-[1-(2-(1-phenylcyclohexyl)-2-oxoethyl)-L-prolyl] benzylamide.

LSIMS=518 (mass calculated for $C_{32}H_{43}N_3O_3$=517.72).

EXAMPLE 117

L-Isoleucine, N-[1-(2-(2,4,5-Trimethoxyphenyl)-2-Oxoethyl)-L-Prolyl] Benzylamide Using the procedure described in Example 5, treatment of L-proline-L-isoleucine benzylamide (200 mg, 0.63 mmol) with 2',4',5'-trimethoxyphenyl α-bromomethyl ketone (274 mg, 0.95 mmol, 1.5 eq) provided 40 mg of L-isoleucine, N-[1-(2-(2,4,5-trimethoxyphenyl)-2-oxoethyl)-L-prolyl] benzylamide.

LSIMS=526 (mass calculated for $C_{29}H_{39}N_3O_6$=525.65).

EXAMPLE 118

1-[2-(3,4,5-Trimethoxyphenyl)-2-Oxoethyl] L-Proline Hydrochloride

Using the procedure described in Example 47, treatment of L-proline benzyl ester hydrochloride (1.00 g, 4.14 mmol) and 3,4,5-trimethoxyphenyl α-bromomethyl ketone (2.4 g, 8.27 mmol) provided the amine (Rf=0.37: 50% EtOAc in hexane).

The amine intermediate was treated with HCl in ether and dried in vacuo to provided 1.58 g of the benzyl ester hydrochloride as a solid. This solid (1.53 g), was dissolved in ethanol (100 mL) and treated with 10% palladium on carbon (150 mg). The flask was purged with argon, purged with hydrogen and left to stir under hydrogen atmosphere (1 atm) until the reaction appeared complete by TLC. The catalyst was removed by filtration through Celite and solvent removed in vacuo to provide 1.15 g of the hydrochloride salt of 1-[2-(3,4,5-trimethoxyphenyl)-2-oxoethyl] L-proline as a solid.

EXAMPLE 119

1-[2-(3,4,5-Trimethoxyphenyl)-2-Oxoethyl] L-Homoproline Hydrochloride

Using the procedure described in Example 118, L-homoproline benzyl ester tosylate salt (5.0 g, 12.77 mmol) and 3,4,5-trimethoxyphenyl α-bromomethyl ketone (7.4 g, 25.6 mmol) provided 5.4 g of the corresponding benzyl ester hydrochloride. The ester was reductively cleaved using the procedure described in Example 118 to provide 4.46 g of the hydrochloride salt of 1-[2-(3,4,5-trimethoxyphenyl)-2-oxoethyl] L-homoproline as a solid.

EXAMPLE 120

Procedure for BOP Coupling

L-Proline, 1-[2-(3,4,5-Trimethoxyphenyl)-2-Oxoethyl] Benzylamide Hydrochloride

To an oven-dried round bottomed flask was added N-[2-(3,4,5-trimethoxyphenyl)-2-oxoethyl]-L-proline hydrochloride, (300 mg, 0.83 mmol, 1.0 eq), benzotriazol-1-yloxy-tris(dimethylamino)phosphonium hexafluorophosphate (369 mg, 0.83 mmol, 1.0 eq.) and anhydrous tetrahydrofuran (10 mL). The slurry was cooled to 0° C. and treated with triethylamine (3.0 eq). After stirring 10 minutes at 0° C., benzylamine (0.27 mL, 2.5 mmol, 3.0 eq) was added and the reaction mixture was allowed to warm to 22° C. over a one hour period. The solvent was removed in vacuo and the resulting residue was taken up in EtOAc (100 mL). The organic layer was washed with 5% citric acid (100 mL), sat. $NaHCO_3$(100 mL), sat. aq. NaCl (100 mL), dried ($MgSO_4$) and concentrated in vacuo. The residue was purified by flash chromatography and treated with HCl in ether to provide 128 mg of the hydrochloride salt of L-proline, 1-[2-(3,4,5-trimethoxyphenyl)-2-oxoethyl] benzylamide as a powder.

LSIMS [M-HCl]=413 (mass calculated for $C_{23}H_{28}N_2O_5$+HCl=448.93).

EXAMPLE 121

L-Proline, 1-[2-(3,4,5-Trimethoxyphenyl)-2-Oxoethyl] 2-Phenethylamide Hydrochloride Following the procedure described in Example 120, the coupling of N-[2-(3,4,5-trimethoxyphenyl)-2-oxoethyl]-L-proline hydrochloride (300 mg, 0.83 mmol) and phenethylamine (0.31 mL, 2.5 mmol) provided, after treatment with HCl in $Et_2O$, 199 mg of the hydrochloride salt of L-proline, 1-[2-(3,4,5-trimethoxyphenyl)-2-oxoethyl] 2-phenethylamide as a powder.

LSIMS [M-HCl]=427 (mass calculated for $C_{24}H_{30}N_2O_5$+HCl=462.98).

EXAMPLE 122

L-Proline, 1-[2-(3,4,5-Trimethoxyphenyl)-2-Oxoethyl] 3-Phenylpropylamide Hydrochloride Following the procedure described in Example 120, the coupling of N-[2-(3,4,5-trimethoxyphenyl)-2-oxoethyl]-L-proline hydrochloride (300 mg, 0.83 mmol) and 3-phenylpropylamine (0.36 mL, 2.5 mmol) provided, after treatment with HCl in $Et_2O$, 120 mg of the hydrochloride salt of L-proline, 1-[2-(3,4,5-trimethoxyphenyl)-2-oxoethyl] 3-phenylpropylamide as a powder.

LSIMS [M-HCl]=441 (mass calculated for $C_{25}H_{32}N_2O_5$+HCl=477.00).

EXAMPLE 123

L-Proline, 1-[2-(3,4,5-Trimethoxyphenyl)-2-Oxoethyl] 4-Phenylbutylamide Hydrochloride Following the procedure described in Example 120, the coupling of N-[2-(3,4,5-trimethoxyphenyl)-2-oxoethyl]-L-proline hydrochloride (300 mg, 0.83 mmol) and 4-phenylbutylamine (0.39 mL, 2.5 mmol) provided, after treatment with HCl in $Et_2O$, 170 mg of the hydrochloride salt of L-proline, 1-[2-(3,4,5-trimethoxyphenyl)-2-oxoethyl] 4-phenylbutylamide as a powder.

LSIMS [M-HCl]=455 (mass calculated for $C_{26}H_{34}N_2O_5$+HCl=491.03).

EXAMPLE 124

L-Proline, 1-[2-(3,4,5-Trimethoxyphenyl)-2-Oxoethyl] 2-(Pyrid-2-yl)ethylamide Dihydrochloride Following the procedure described in Example 120, the coupling of N-[2-(3,4,5-trimethoxyphenyl)-2-oxoethyl]-L-proline hydrochloride (300 mg, 0.83 mmol) and 2(2-aminoethyl)pyridine (0.4 mL, 2.5 mmol ) provided, after treatment with HCl in $Et_2O$, 193 mg of the dihydrochloride salt of L-proline, 1-[2-(3,4,5-trimethoxyphenyl)-2-oxoethyl] 2-(pyrid-2-yl)ethylamide as a powder.

LSIMS [M-2HCl]=429 (mass calculated for $C_{23}H_{29}N_3O_5 \times 2HCl$=500.43).

EXAMPLE 125

L-Proline, 1-[2-(3,4,5-Trimethoxyphenyl)-2-Oxoethyl] 2-(4-aminophenyl)ethylamide Dihydrochloride Following the procedure described in Example 120, the coupling of N-[2-(3,4,5-trimethoxyphenyl)-2-oxoethyl]-L-proline hydrochloride (300 mg, 0.83 mmol) and (4-aminophenyl)ethylamine (0.4 mL, 2.5 mmol) provided, after treatment with HCl in $Et_2O$, 102 mg of the dihydrochloride salt of L-proline, 1-[2-(3,4,5-trimethoxyphenyl)-2-oxoethyl] 2-(4-aminophenyl)ethylamide as a powder.

$R_f$=0.27 (for free base: EtOAc)

LSIMS [M-2HCl]=442 (mass calculated for $C_{24}H_{31}N_3O_5 \times 2HCl$=514.45).

EXAMPLE 126

L-Proline, 1-[2-(3,4,5-Trimethoxyphenyl)-2-Oxoethyl] 3-(4-[N-Carboallyloxy] aminophenyl)propyl Ester Hydrochloride Following the procedure described in Example 120, the coupling of N-[2-(3,4,5-trimethoxyphenyl)-2-oxoethyl]-L-proline hydrochloride (300 mg, 0.83 mmol) and 3-(4-(N-carboallyloxy)aminophenyl)propanol (218 mg, 0.83 mmol) provided, after treatment with HCl in $Et_2O$, 65 mg of the hydrochloride salt of L-proline, 1-[2-(3,4,5-trimethoxyphenyl)-2-oxoethyl] 3-(4-[N-carboallyloxy] aminophenyl)propyl ester as a foam.

LSIMS [M-HCl]=542 (mass calculated for $C_{29}H_{36}N_2O_8$+HCl=577.08).

EXAMPLE 127

L-Proline, 1-[2-(3,4,5-Trimethoxyphenyl)-2-Oxoethyl] 2-Phenyl-2-oxoethylamide

Following the procedure described in Example 120, the coupling of N-[2-(3,4,5-trimethoxyphenyl)-2-oxoethyl]-L-proline hydrochloride (200 mg, 0.56 mmol) and 2-aminoacetophenone hydrochloride (286 mg, 1.67 mmol) provided 54 mg of L-proline, 1-[2-(3,4,5-trimethoxyphenyl)-2-oxoethyl] 2-phenyl-2-oxoethylamide as a powder.

Rf=0.46 (EtOAc)

LSIMS=442 (mass calculated for $C_{24}H_{28}N_2O_6$=440.50).

EXAMPLE 128

L-Proline, 1-[2-(3,4,5-Trimethoxyphenyl)-2-Oxoethyl] Tetrahydrofurfurylamide

Following the procedure described in Example 120, the coupling of N-[2-(3,4,5-trimethoxyphenyl)-2-oxoethyl]-L-proline hydrochloride (200 mg, 0.56 mmol) and tetrahydrofurfurylamine (0.17 mL, 1.67 mmol) provided 104 mg of L-proline, 1-[2-(3,4,5-trimethoxyphenyl)-2-oxoethyl] tetrahydrofurfurylamide as a powder.

Rf=0.20 (EtOAc)

LSIMS=407 (mass calculated for $C_{21}H_{30}N_2O_6$=406.48).

EXAMPLE 129

L-Proline, 1-[2-(3,4,5-Trimethoxyphenyl)-2-Oxoethyl] Naphthalen-1-ylmethylamide

Following the procedure described in Example 120, the coupling of N-[2-(3,4,5-trimethoxyphenyl)-2-oxoethyl]-L-proline hydrochloride (300 mg, 0.83 mmol) and 1-naphthyl methylamine (0.37 mL, 2.5 mmol) provided 150 mg of L-proline, 1-[2-(3,4,5-trimethoxyphenyl)-2-oxoethyl] naphthalen-1-ylmethylamide as a powder.

LSIMS=463 (mass calculated for $C_{27}H_{30}N_2O_5$=462.55).

EXAMPLE 130

L-Proline, 1-[2-(3,4,5-Trimethoxyphenyl)-2-Oxoethyl] 2-(4-Sulfamoylphenyl)ethylamide Following the procedure described in Example 120, the coupling of N-[2-(3,4,5-trimethoxyphenyl)-2-oxoethyl]-L-proline hydrochloride (300 mg, 0.83 mmol) and 4-(2-aminoethyl)benzene sulfonamide (334 mg, 1.67 mmol) provided 300 mg of L-proline, 1-[2-(3,4,5-trimethoxyphenyl)-2-oxoethyl] 2-(4-sulfamoylphenyl)ethylamide as a powder.

LSIMS=506 (mass calculated for $C_{24}H_{31}N_3SO_7$=505.60).

EXAMPLE 131

L-Proline, 1-[2-(3,4,5-Trimethoxyphenyl)-2-Oxoethyl] 4-Phenylpiperldenylamide

Following the procedure described in Example 120, the coupling of N-[2-(3,4,5-trimethoxyphenyl)-2-oxoethyl]-L-proline hydrochloride (250 mg, 0.69 mmol) and 4-phenylpiperidine (336 mg, 2.1 mmol) provided 67 mg of L-proline, 1-[2-(3,4,5-trimethoxyphenyl)-2-oxoethyl] 4-phenylpiperidenyl amide as a foam.

Rf=0.22 (EtOAc)

LSIMS=467 (mass calculated for $C27H_{34}N_2O_5$=466.58).

EXAMPLE 132

L-Proline, 1-[2-(3,4,5-Trimethoxyphenyl)-2-Oxoethyl] 4-Methoxybenzamide Hydrochloride Following the procedure described in Example 120, the coupling of N-[2-(3,4,5-trimethoxyphenyl)-2-oxoethyl]-L-proline hydrochloride (250 mg, 0.69 mmol) and 4-methoxybenzylamine (0.27 mL, 2.1 mmol) provided, after treatment with HCl in $Et_2O$, 90 mg of the hydrochloride salt of L-proline, 1-[2-(3,4,5-trimethoxyphenyl)-2-oxoethyl] 4-methoxybenzamide as a powder.

Rf=0.38 (free base in EtOAc)

LSIMS [M-HCl]=443 (mass calculated for $C_{24}H_{30}N_2O_6$+HCl=478.98).

EXAMPLE 133

L-Proline, 1-[2-(3,4,5-Trimethoxyphenyl)-2-Oxoethyl] 3-Methoxybenzamide Hydrochloride Following the procedure described in Example 120, the coupling of N-[2-(3,4,5-trimethoxyphenyl)-2 -oxoethyl]-L-proline hydrochloride ( 250 mg, 0.69 mmol) and 3-methoxybenzylamine (0.27 mL, 2.1 mmol) provided, after treatment with HCl in $Et_2O$, 90 mg of the hydrochloride salt of L-proline, 1-[2-(3,4,5-trimethoxyphenyl)-2-oxoethyl] 3-methoxybenzamide as a powder.

Rf=0.38 (free base in EtOAc)

LSIMS [M-HCl]=443 (mass calculated for $C_{24}H_{30}N_2O_6$+HCl=478.98).

EXAMPLE 134

L-Proline, 1-[2-(3,4,5-Trimethoxyphenyl)-2-Oxoethyl] 2-Methoxybenzamide Hydrochloride Following the procedure described in Example 120, the coupling of N-[2-(3,4,5-trimethoxyphenyl)-2-oxoethyl]-L-proline hydrochloride (250 mg, 0.69 mmol) and 2-methoxybenzylamine (0.27 mL, 2.1 mmol) provided, after treatment with HCl in $Et_2O$, 120 mg of the hydrochloride salt of L-Proline, 1-[2-(3,4,5-Trimethoxyphenyl)-2-Oxoethyl] 2-Methoxybenzamide as a powder.

Rf=0.38 (free base in EtOAc)

LSIMS [M-HCl]=443 (mass calculated for $C_{24}H_{30}N_2O_6$+HCl=478.98).

EXAMPLE 135

L-Proline, 1-[2-(3,4,5-Trimethoxyphenyl)-2-Oxoethyl] N-Methylphenethylamide Hydrochloride Following the procedure described in Example 120, the coupling of N-[2-(3,4,5-trimethoxyphenyl)-2-oxoethyl]-L-proline hydrochloride (250 mg, 0.69 mmol) and N-methyl phenethylamine (0.30 mL, 2.1 mmol) provided, after treatment with HCl in $Et_2O$, 20 mg of the hydrochloride salt of L-proline, 1-[2-(3,4,5-trimethoxyphenyl)-2-oxoethyl] N-methyl phenethylamide as a powder LSIMS [M-HCl]=441 (mass calculated for $C_{25}H_{32}N_2O_5$+HCl=477.00).

EXAMPLE 136

L-Proline, 1-[2-(3,4,5-Trimethoxyphenyl)-2-Oxoethyl] (S)-α-methylbenzylamide Hydrochloride Following the procedure described in Example 120, the coupling of N-[2-(3,4,5-trimethoxyphenyl)-2-oxoethyl]-L-proline hydrochloride (250 mg, 0.69 mmol) and (S)-(−)-α-methylbenzylamine (0.27 mL, 2.1 mmol) provided, after treatment with HCl in $Et_2O$, 160 mg of the hydrochloride salt of L-proline, 1-[2-(3,4,5-trimethoxyphenyl)-2-oxoethyl] (S)-α-methylbenzylamide as a powder.

LSIMS [M-HCl]=427 (mass calculated for $C_{24}H_{30}N_2O_5$+HCl=462.98).

EXAMPLE 137

L-Proline, 1-[2-(3,4,5-Trimethoxyphenyl)-2-Oxoethyl] (R)-α-methylbenzylamide Hydrochloride Following the procedure described in Example 120, the coupling of N-[2-(3,4,5-trimethoxyphenyl)-2-oxoethyl]-L-proline hydrochloride (250 mg, 0.69 mmol) and (R)-(+)-α-methylbenzylamine (0.27 mL, 2.1 mmol) provided, after treatment with HCl in $Et_2O$, 190 mg of the hydrochloride salt of L-proline, 1-[2-(3,4,5-trimethoxyphenyl)-2-oxoethyl] (R)-α-methylbenzylamide as a powder.

LSIMS [M-HCl]=427 (mass calculated for $C_{24}H_{30}N_2O_5$+HCl=462.98).

EXAMPLE 138

L-Proline, 1-[2-(3,4,5-Trimethoxyphenyl)-2-Oxoethyl] 1-methyl-3-phenylpropylamide Hydrochloride Following the procedure described in Example 120, the coupling of N-[2-(3,4,5-trimethoxyphenyl)-2-oxoethyl]-L-proline hydrochloride (250 mg, 0.69 mmol) and 1-methyl-3-phenylpropylamine (0.34 mL, 2.1 mmol) provided, after treatment with HCl in Et$_2$O, 40 mg of the hydrochloride salt of L-proline, 1-[2-(3,4,5-trimethoxyphenyl)-2-oxoethyl] 1-methyl-3-phenylpropylamide as a foam.

LSIMS [M-HCl]=455 (mass calculated for C$_{26}$H$_{34}$N$_2$O$_5$+ HCl=491.03).

EXAMPLE 139

L-Proline, 1-[2-(3,4,5-Trimethoxyphenyl)-2-Oxoethyl] Adamant-1-ylmethylamide Hydrochloride Following the procedure described in Example 120, the coupling of N-[2-(3,4,5-trimethoxyphenyl)-2-oxoethyl]-L-proline hydrochloride (250 mg, 0.69 mmol) and 1-adamantylmethylamine (0.37 mL, 2.1 mmol) provided, after treatment with HCl in Et$_2$O, 100 mg of the hydrochloride salt of L-proline, 1-[2-(3,4,5-trimethoxyphenyl)-2-oxoethyl] adamant-1-ylmethylamide as a powder.

LSIMS [M-HCl]=471 (mass calculated for C$_{27}$H$_{38}$N$_2$O$_5$+ HCl=507.07).

EXAMPLE 140

L-Proline, 1-[2-(3,4,5-Trimethoxyphenyl)-2-Oxoethyl] 1-(R)-(1-naphthyl)ethylamide Hydrochloride Following the procedure described in Example 120, the coupling of N-[2-(3,4,5-trimethoxyphenyl)-2-oxoethyl]-L-proline hydrochloride (250 mg, 0.69 mmol) and (R)-1-(1-naphthyl)ethylamine (0.34 mL, 2.1 mmol) provided, after treatment with HCl in Et$_2$O, 137 mg of the hydrochloride salt of L-proline, 1-[2-(3,4,5-trimethoxyphenyl)-2-oxoethyl] (R)-1-(1-naphthyl)ethylamide as a powder.

LSIMS [M-HCl]=477 (mass calculated for C$_{28}$H$_{32}$N$_2$O$_5$+ HCl=513.04).

EXAMPLE 141

L-Proline, 1-[2-(3,4,5-Trimethoxylphenyl)-2-Oxoethyl] Cyclohexylmethylamide

Following the procedure described in Example 120, the coupling of N-[2-(3,4,5-trimethoxyphenyl) -2-oxoethyl]-L-proline hydrochloride (250 mg, 0.69 mmol) and cyclohexylmethylamine (0.27 mL, 2.1 mmol), provided 138 mg of L-proline, 1-[2-(3,4,5-trimethoxyphenyl)-2-oxoethyl] cyclohexyl methylamide as a powder.

LSIMS=419 (mass calculated for C$_{24}$H$_{34}$N$_2$O$_5$=418.54).

EXAMPLE 142

L-Proline, 1-[2-(3,4,5-Trimethoxyphenyl)-2-Oxoethyl] Diphenylmethylamide Hydrochloride Following the procedure described in Example 120, the coupling of N-[2-(3,4,5-trimethoxyphenyl)-2 -oxoethyl]-L-proline hydrochloride (250 mg, 0.69 mmol) and aminodiphenylmethane (0.12 mL, 0.69 mmol) provided, after treatment with HCl in Et$_2$O, 132 mg of the hydrochloride salt of L-proline, 1-[2-(3,4,5-trimethoxyphenyl)-2-oxoethyl] diphenylmethylamide as a powder.

LSIMS [M-HCl]=489 (mass calculated for C$_{29}$H$_{32}$N$_2$O$_5$+ HCl=525.05).

EXAMPLE 143

L-Proline, 1-[2-(3,4,5-Trimethoxyphenyl)-2-Oxoethyl] tert-Butylamide Hydrochloride Following the procedure described in Example 120, the coupling of N-[2-(3,4,5-trimethoxyphenyl)-2-oxoethyl] -L-proline hydrochloride (250 mg, 0.69 mmol) and t-butylamine (0.22 mL, 2.1 mmol) provided, after treatment with HCl in Et$_2$O, 146 mg of the hydrochloride salt of L-proline, 1-[2-(3,4,5-trimethoxyphenyl)-2-oxoethyl] tert-butylamide as a powder.

Rf=0.42 (for free base: EtOAc)

LSIMS [M-HCl]=379 (mass calculated for C$_{20}$H$_{30}$N$_2$O$_5$+ HCl=414.93).

EXAMPLE 144

L-Proline, 1-[2-(3,4,5-Trimethoxyphenyl)-2-Oxoethyl] 1,2-Diphenylethylamide Hydrochloride Following the procedure described in Example 120, the coupling of N-[2-(3,4,5-trimethoxyphenyl)-2-oxoethyl]-L-proline hydrochloride (250 mg, 0.69 mmol) and 1,2-diphenylethylamine (0.40 mL, 2.1 mmol) provided, after treatment with HCl in Et$_2$O, 95 mg of the hydrochloride salt of L-proline, 1-[2-(3,4,5-trimethoxyphenyl)-2-oxoethyl] 1,2-diphenylethylamide as a powder.

Rf=0.56 (free base in EtOAc)

LSIMS [M-HCl]=503 (mass calculated for C$_{30}$H$_{34}$N$_2$O$_5$+ HCl=539.07).

EXAMPLE 145

L-Proline, 1-[2-(3,4,5-Trimethoxyphenyl)-2-Oxoethyl] Cyclohexyl amide Hydrochloride Following the procedure described in Example 120, the coupling of N-[2-(3,4,5-trimethoxyphenyl)-2-oxoethyl] -L-proline hydrochloride (250 mg, 0.69 mmol) and cyclohexylamine (0.24 mL, 2.1 mmol) provided, after treatment with HCl in Et$_2$O, 147 mg of the hydrochloride salt of L-proline, 1-[2-(3,4,5-trimethoxyphenyl)-2-oxoethyl] cyclohexylamide as a powder.

Rf=0.34 (free base in EtOAc)

LSIMS [M-HCl]=405 (mass calculated for C$_{22}$H$_{32}$N$_2$O$_5$+ HCl=440.97).

EXAMPLE 146

L-Homoproline, 1-[2-(3,4,5-Trimethoxyphenyl)-2-Oxoethyl] Benzylamide Hydrochloride Following the procedure described in Example 120, the coupling of N-[2-(3,4,5-trimethoxyphenyl)-2-oxoethyl] -L-homoproline hydrochloride (200 mg, 0.53 mmol) and benzylamine (0.09 mL, 0.80 mmol) provided, after treatment with HCl in Et$_2$O, 112 mg of the hydrochloride salt of L-homoproline, 1-[2-(3,4,5-trimethoxyphenyl)-2-oxoethyl] benzylamide as a powder.

LSIMS [M-HCl]=427 (mass calculated for C$_{24}$H$_{30}$N$_2$O$_5$+ HCl=462.98).

EXAMPLE 147

L-Homoproline, 1-[2-(3,4,5-Trimethoxyphenyl)-2-Oxoethyl] Adamant-1-ylmethylamide Hydrochloride Following the procedure described in Example 120, the coupling of N-[2-(3,4,5-trimethoxyphenyl)-2-oxoethyl] -L-homoproline hydrochloride (200 mg, 0.53 mmol) and 1-adamantylmethylamine (0.19 mL, 1.07 mmol) provided, after treatment with HCl in Et$_2$O, 59 mg of the hydrochloride salt of L-homoproline, 1-[2-(3,4,5-trimethoxyphenyl)-2-oxoethyl] adamant-1-ylmethylamide as a powder.

LSIMS [M-HCl]=485 (mass calculated for C$_{28}$H$_{40}$N$_2$O$_5$+ HCl=521.10).

EXAMPLE 148

L-Homoproline, 1-[2-(3,4,5-Trimethoxyphenyl)-2-Oxoethyl] tetrahydrofurfurylamide Following the procedure described in Example 120, the coupling of N-[2-(3,4,5-trimethoxylphenyl)-2-oxoethyl]-L-homoproline hydrochloride (200 mg, 0.53 mmol) and tetrahydrofurfurylamine (0.17 mL, 1.6 mmol), provided 100 mg of L-homoproline, 1-[2-(3,4,5-trimethoxyphenyl)-2-oxoethyl] tetrahydrofurfurylamide as a sticky solid.
LSIMS=421 (mass calculated for $C_{22}H_{32}N_2O_6$=420.51).

EXAMPLE 149

L-Homoproline, 1-[2-(3,4,5-Trimethoxyphenyl)-2-Oxoethyl] 2-(4-Sulfamoylphenyl)ethylamide Following the procedure described in Example 120, the coupling of N-[2-(3,4,5-trimethoxyphenyl)-2-oxoethyl]-L-homoproline hydrochloride (200 mg, 0.53 mmol) and 4-(2-aminoethyl)benzenesulfonamide (214 mg, 1.06 mmol) provided 25 mg of L-homoproline, 1-[2-(3,4,5-trimethoxyphenyl)-2-oxoethyl] 2-(4-sulfamoylphenyl)ethylamide as a solid.
LSIMS=520 (mass calculated for $C_{25}H_{33}N_3O_7S$=519.62).

EXAMPLE 150

L-Homoproline, 1-[2-(3,4,5-Trimethoxyphenyl)-2-Oxoethyl] (S)-α-methylbenzylamide Hydrochloride Following the procedure described in Example 120, the coupling of N-[2-(3,4,5-trimethoxyphenyl)-2-oxoethyl]-L-homoproline hydrochloride (200 mg, 0.53 mmol) and (S)-(−)-α-methylbenzylamine (0.21 mL, 1.6 mmol) provided, after treatment with HCl in $Et_2O$, 107 mg of the hydrochloride salt of L-homoproline, 1-[2-(3,4,5-trimethoxyphenyl)-2-oxoethyl] (S)-α-methylbenzylamide as a powder.

LSIMS [M-HCl]=441 (mass calculated for $C_{25}H_{32}N_2O_5$+HCl=477.00).

EXAMPLE 151

L-Homoproline, 1-[2-(3,4,5-Trimethoxyphenyl)-2-Oxoethyl] (1-(S)-[2'-(S)-methylpropyl]-3-phenylprop-2-E-enyl)-amide Following the procedure described in Example 120, the coupling of N-[2-(3,4,5-trimethoxyphenyl)-2-oxoethyl]-L-homoproline hydrochloride (300 mg, 0.80 mmol) and trans 1-phenyl-3-(S)-amino-4-(S)-methylhexa-1-ene (228 mg, 1.2 mmol) provided 280 mg of L-homoproline, 1-[2-(3,4,5-trimethoxyphenyl)-2-oxoethyl] (1-(S)-[2'-(S)-methylpropyl]-3-phenylprop-2-E-enyl)-amide as a solid.
LSIMS=509 (mass calculated for $C_{30}H_{40}N_2O_5$=508.66).

EXAMPLE 152

L-Homoproline, 1-[2-(3,4,5-Trimethoxyphenyl)-2-Oxoethyl] (1-(S)-[2'-(S)-methylpropyl]-3-phenylpropyl)-amide In a round bottomed flask equipped with a magnetic stirrer was added L-homoproline, 1-[2-(3,4,5-trimethoxyphenyl)-2-oxoethyl] (1-(S)-[2'-(S)-methylpropyl]-3-phenylprop-2-enyl)-amide (220 mg, 0.43 mmol), 10% palladium on carbon (22 mg), and methanol (50 mL) The flask was purged with hydrogen and the slurry stirred under an atmosphere of $H_2$ for 2 hours. The catalyst was removed by filtration through celite and the solvent removed in vacuo to provide 220 mg of L-homoproline, 1-[2-(3,4,5-trimethoxyphenyl)-2-oxoethyl] (1-(S)-[2'-(S)-methylpropyl]-3-phenylpropyl)-amide.
LSIMS=511 (mass calculated for $C_{30}H_{42}N_2O_5$=510.68).

EXAMPLE 153

L-Isoleucine, N-[1-(2-(3,4,5-Trimethoxyphenyl)-2-Oxoethyl)-L-Homoprolyl] Benzylamide Following the procedure described in Example 120, the coupling of N-[2-(3,4,5-trimethoxyphenyl)-2-oxoethyl]-L-homoproline hydrochloride (200 mg, 0.53 mmol) and L-isoleucine benzylamide (118 mg, 0.53 mmol) provided 190 mg of L-isoleucine, N-[1-(2-(3,4,5-trimethoxyphenyl)-2-oxoethyl)-L-homoprolyl] benzylamide as a solid.
LSIMS=540 (mass calculated for $C_{30}H_{41}N_3O_6$=539.68).

EXAMPLE 154

L-Proline, 1-[2-(3,4,5-Trimethoxyphenyl)-2-Oxoethyl] 2-(4-(N-Acetyl)aminophenyl)ethylamide In an oven-dried round bottomed flask was added L-proline, 1-[2-(3,4,5-trimethoxyphenyl)-2-oxoethyl] 2-(4-aminophenyl)ethylamide (100 mg, 0.23 mmol), and tetrahydrofuran (5 mL). The solution was stirred at 22° C., and treated with pyridine (0.037 mL, 0.45 mmol, 2.0 eq) followed by acetyl chloride (0.024 mL, 0.34 mmol, 1.5 eq). The reaction mixture was allowed to stir for one hour. The solvent was removed in vacuo and the residue partitioned between EtOAc (50 mL) and sat. $NaHCO_3$ (50 mL). The organic layer was washed with sat. aq. NaCl, dried ($MgSO_4$) and concentrated to an oil. The oil was purified by flash chromatography to provide 70 mg of L-proline, 1-[2-(3,4,5-trimethoxyphenyl)-2-oxoethyl] 2-(4-(N-acetyl)aminophenyl)ethylamide as a foam.
LSIMS=484 (mass calculated for $C_{26}H_{33}N_3O_6$=483.57).

EXAMPLE 155

L-Proline, 1-[2-(3,4,5-Trimethoxyphenyl)-2-Oxoethyl] 2-(4-(N-Benzoyl)aminophenyl)ethylamide Following the procedure described in Example 154, treatment of L-proline, 1-[2-(3,4,5-trimethoxyphenyl)-2-oxoethyl] 2-(4-aminophenyl)ethylamide (100 mg, 0.23 mmol) with benzoyl chloride (0.039 mL, 0.34 mmol) provided 67 mg of L-proline, 1-[2-(3,4,5-trimethoxyphenyl)-2-oxoethyl] 2-(4-(N-benzoyl)aminophenyl)ethylamide as a foam.

$R_f$=0.35 (EtOAc)

LSIMS=546 (mass calculated for $C_{31}H_{35}N_3O_6$=545.64).

EXAMPLE 156

L-Proline, 1-[2-(3,4,5-Trimethoxyphenyl)-2-Oxoethyl] 2-(4-(N-carboalloxy)aminophenyl)ethylamide Following the procedure described in Example 154, treatment of L-proline, 1-[2-(3,4,5-trimethoxyphenyl)-2-oxoethyl] 2-(4-aminophenyl)ethylamide (100 mg, 0.23 mmol) with allyl chloroformate (0.036 mL, 0.34 mmol) provided 90 mg of L-proline, 1-[2-(3,4,5-trimethoxyphenyl)-2-oxoethyl] 2-(4-(N-carboalloxy)aminophenyl)ethylamide as a foam.

$R_f$=0.42 (EtOAc)

LSIMS=526 (mass calculated for $C_{28}H_{35}N_3O_7$=525.61).

EXAMPLE 157

L-Proline, 1-[2-(3,4,5-Trimethoxyphenyl)-2-Oxoethyl] 2-(4-(N-Carbobenzyloxy)aminophenyl)ethylamide Following the procedure described in Example 154, treatment of L-proline, 1-[2-(3,4,5-trimethoxyphenyl)-2- oxoethyl] 2-(4-aminophenyl)ethylamide (80 mg, 0.18 mmol) with benzyl chloroformate (0.039 mL, 0.27 mmol) provided 72 mg of L-proline, 1-[2-(3,4,5-trimethoxyphenyl)-2-oxoethyl] 2-(4-(N-carbobenzyloxy)aminophenyl)ethylamide as a foam.

Rf=0.42 (EtOAc)

LSIMS=577 (mass calculated for $C_{32}H_{37}N_3O_7$=575.67).

EXAMPLE 158

L-Homoproline 3-(4-(N-Carboallyloxy)aminophenyl) propyl Ester Trifluoroacetate Salt To an oven-dried round bottomed flask was added N-Boc-L-pipecolinc acid (500 mg, 2.2 mmol), 1.0 eq benzotriazol-1-yloxy-tris(dimethylamino)phosphonium hexafluorophosphate (966 mg, 2.2 mmol), 3-(4-(N-carboallyloxy) aminophenyl)propanol (514 mg, 2.2 mmol) and anhydrous dichloromethane (20 mL). The solution was cooled to 0° C. and treated with triethylamine (0.92 mL, 6.6 mmol, 3.0 eq). After stirring for 3 hours at 0° C., the reaction mixture was diluted with dichloromethane (100 mL), washed with 5% citric acid (100 mL), sat. NaHCO₃ (100 mL), sat. aq. NaCl (100 mL), and dried (MgSO₄). The solution was concentrated in vacuo, and purified by flash chromatography to provide 740 mg of the Boc-protected intermediate. This material was dissolved in ether (20 mL) and treated with trifluoroacetic acid (2 mL) and allowed to stir at 22° C. for 17 hours. The solvent was removed in vacuo and the residue triturated three times with ether and dried to provide 220 mg of L-homoproline 3-(4-(N-carboallyloxy)aminophenyl) propyl ester as the trifluoroacetic acid salt.

EXAMPLE 159

L-Homoproline, 1-[2-(3,4,5-Trimethoxyphenyl)-2-Oxoethyl] 3-(4-(N-Carboallyloxy)aminophenyl)propyl Ester Hydrochloride In an oven-dried flask, was added L-homoproline 3-(4-(N-carboallyloxy)aminophenyl)propyl ester as the trifluoroacetic acid salt (200 mg), 3,4,5-trimethoxyphenyl-2-bromoacetophenone, and THF (20 mL). The slurry was treated with triethylamine (0.3 mL, 2.2 mmol, 5 eq) and heated to reflux for 4 hours. The solvent was removed in vacuo and the residue was taken up in EtOAc (100 mL) and washed with sat. NaHCO₃ (100 mL), sat. aq. NaCl (100 mL), dried (MgSO₄) and concentrated in vacuo. The residue was purified by flash chromatography to provide the free amine (Rf=0.44: 30% EtOAc in hexane) which was treated with HCl in ether and dried in vacuo to provide 60 mg of the hydrochloride salt of L-homoproline, 1-[2-(3,4,5-trimethoxyphenyl)-2-oxoethyl] 3-(4-(N-carboallyloxy) aminophenyl)propyl ester as a solid.

LSIMS [M-HCl]=555 (mass calculated for $C_{30}H_{38}N_2O_8$+HCl=591.10).

EXAMPLE 160

L-Proline, 1-[2-Adamantan-1-yl-2-Oxoethyl] 3-(4-(N-Carboallyloxy) aminophenyl)propyl Ester Hydrochloride Following the procedure described in Example 159, the coupling of N-Boc-L-proline (457 mg, 2.1 mmol ) and 3-(4-(N-carboallyloxy)aminophenyl)propanol (500 mg, 2.1 mmol) provided 580 mg of the Boc-protected intermediate. This intermediate was deprotected with 1N HCl in ether (20 mL) and the mixture was allowed to stir for 17 hours at 22° C. The solution was concentrated in vacuo to provide 490 mg of the corresponding hydrochloride salt.

A portion of the hydrochloride salt (195 mg, 0.53 mmol) was treated with 1-adamantyl α-bromomethyl ketone (272 mg, 1.06 mmol), using the procedure described in example 159. This provided the free amine which was treated with HCl in ether and dried in vacuo to provide 90 mg of the hydrochloride salt of L-proline, 1-[2-adamantan-1-yl-2-oxoethyl] 3-(4-(N-carboallyloxy)aminophenyl)propyl ester as a solid.

Rf=0.38 (for free base: 50% EtOAc in hexane).

LSIMS [M-HCl]=509 (mass calculated for $C_{30}H_{40}N_2O_5$+HCl=545.12).

EXAMPLE 161

L-Homoproline, 1-[2-Adamant-1-yl-2-Oxoethyl] 3-(4-(N-Carboallyloxy)aminophenyl)propyl Ester Hydrochloride Following the procedure described in Example 159, 3-(4-(N-carboallyloxy) aminophenyl)propyl pipecolinate, trifluoroacetic acid salt (220 mg, 0.48 mmol) and 1-adamantyl α-bromomethyl ketone (250 mg, 0.97 mmol) provided the amine which was treated with HCl in ether to provide 40 mg of of the hydrochloride salt of L-homoproline, 1-[2-adamantan-1-yl-2-oxoethyl] 3-(4-(N-carboallyloxy) aminophenyl) propyl ester as a powder.

LSIMS [M-Cl]=523 (mass calculated for $C_{31}H_{42}N_2O_5$+HCl=559.15).

The immunosuppressive properties of the present compounds were evaluated in the following assays:

1) Inhibition of PPIase Activity

This assay follows in principle the procedure described in Kofron et al., 1991, Biochemistry 30:6127.

The three main reagents used are PPIase, a substrate for PPIase, and a selected inhibitor compound of the present invention. The basic principle behind this assay is the conversion of the cis isomer of the substrate to the trans form, which conversion is catalyzed by PPIase. Essentially, inhibition of this PPIase activity is measured for the selected compounds. A peptide chymotrypsin substrate containing a proline in the P2 position is only cleaved by chymotrypsin when the Phe-Pro bond is in the trans isomeric configuration. In the presence of excess chymotrypsin, all of the trans peptide isomers are cleaved within approximately five seconds, leaving only cis forms.

The cis peptide will spontaneously convert to the trans isomer at a slow rate. The cis to trans conversion is catalyzed by isomerases at a much faster rate than this spontaneous conversion. Proteins with PPIase activity are examples of such isomerases. After isomerization, the peptide is cleaved by chymotrypsin releasing p-nitroaniline which can be monitored at 390 nm. The rate of release is then calculated using a first order rate plus offset equation utilizing the ENZFITTER program (Leatherbarrow, BIOSOFT, Cambridge, United Kingdom).

EXAMPLE 162

PPIase Inhibition Assay

In a plastic cuvette are added 950 ul of ice cold assay buffer (25 mM HEPES, pH 7.8, 100 mM NaCl), 10 uL of FKBP (2.5 uM in 10 mM Tris-Cl pH 7.5, 100 mM NaCl, 1 mM dithiothreitol), 25 ul of chymotrypsin (50 mg/ml in 1 mM HCl) and 10 ul of the test compound at various concentrations in dimethyl sulphoxide. The reaction is initiated by addition of 5 ul of substrate (Succinyl-Ala-Phe-Pro-Phe-para-nitroanilide, 5 mg/ml in 235 mM LiCl in trifluoroethanol).

The absorbance at 390 nm versus time is monitored for 90 sec using a Beckman DU70 spectrophotometer. The absorbance versus time data files are transferred to an IBM XT computer and the rate constants determined using the commercial enzfitter program. For each set of data, the uncatalyzed rate of conversion is measured and the uninhibited enzymatic rate determined. The data are expressed as % Activity remaining and are calculated as follows:

$$\% \text{ Activity Remaining} = (k_{obs} - k_{uncat})/(k_{uninh} - k_{uncat}) \times 100$$

where $k_{obs}$ is the rate in the presence of a selected test compound, $k_{uncat}$ is the rate in the absence of enzyme, and $k_{uninh}$ is the rate in the presence of enzyme Compounds were inhibitor.

Compounds were assayed at 5 to 50 uM final concentrations, depending on relative potencies of the compounds. The values of the concentration of inhibitor required for 50% inhibition of enzyme activity ($IC_{50}$) were determined by assay of the enzyme in the presence of varied concentrations of the inhibitor. Data was plotted as the velocity in the absence of the inhibitor (V−) divided by the velocity in the presence of inhibitor (V+) versus the inhibitor concentration. The $IC_{50}$ can be determined following linear regression as the inhibitor concentration where $$V-/V+=2.$$

TABLE I

| Compound of Example No: | $IC_{50}$ (uM) |
| --- | --- |
| Example 5 | 2.2 |
| Example 6 | <50 |
| Example 7 | 2.7 |
| Example 8 | 3.4 |
| Example 9 | <50 |
| Example 10 | <50 |
| Example 11 | 50 |
| Example 12 | 5.8 |
| Example 13 | <50 |
| Example 14 | <50 |
| Example 15 | <50 |
| Example 16 | >50 |
| Example 17 | <50 |
| Example 18 | <50 |
| Example 19 | <50 |
| Example 20 | <50 |
| Example 21 | <50 |
| Example 22 | >50 |
| Example 23 | <50 |
| Example 24 | 0.06 |
| Example 25 | 0.99 |
| Example 26 | <50 |
| Example 27 | 12 |
| Example 28 | <50 |
| Example 29 | <50 |
| Example 30 | <50 |
| Example 31 | <5 |
| Example 32 | <5 |
| Example 33 | 5 |
| Example 34 | <5 |
| Example 35 | >5 |
| Example 36 | 2.2 |
| Example 37 | >50 |
| Example 38 | n.d. |
| Example 39 | 15 |
| Example 40 | <5 |
| Example 41 | <5 |
| Example 42 | >5 |
| Example 43 | <5 |
| Example 44 | <5 |
| Example 45 | <5 |
| Example 46 | <5 |
| Example 50 | 50 |
| Example 51 | >50 |
| Example 52 | <50 |

TABLE I-continued

| Compound of Example No: | $IC_{50}$ (uM) |
| --- | --- |
| Example 53 | >50 |
| Example 54 | >50 |
| Example 55 | 5.1 |
| Example 56 | 1.2 |
| Example 57 | 0.22 |
| Example 58 | 2.3 |
| Example 59 | 0.71 |
| Example 60 | 0.4 |
| Example 61 | <5 |
| Example 62 | 1.3 |
| Example 63 | 0.3 |
| Example 64 | <5 |
| Example 65 | 0.1 |
| Example 66 | 0.1 |
| Example 67 | 0.71 |
| Example 68 | 0.4 |
| Example 69 | 0.2 |
| Example 70 | 0.64 |
| Example 71 | >5 |
| Example 72 | <5 |
| Example 73 | <5 |
| Example 74 | <5 |
| Example 75 | <5 |
| Example 76 | >5 |
| Example 77 | <5 |
| Example 78 | >5 |
| Example 79 | >5 |
| Example 80 | >5 |
| Example 81 | >5 |
| Example 82 | <5 |
| Example 83 | >5 |
| Example 84 | 3.2 |
| Example 85 | <5 |
| Example 86 | 0.88 |
| Example 87 | >5 |
| Example 88 | <5 |
| Example 89 | 0.12 |
| Example 90 | <5 |
| Example 91 | <5 |
| Example 92 | 0.6 |
| Example 93 | 1.2 |
| Example 96 | <5 |
| Example 97 | <5 |
| Example 98 | <5 |
| Example 99 | 5 |
| Example 100 | >5 |
| Example 101 | <5 |
| Example 102 | 5 |
| Example 103 | <5 |
| Example 104 | <5 |
| Example 105 | <5 |
| Example 106 | <5 |
| Example 107 | <5 |
| Example 108 | <5 |
| Example 109 | <5 |
| Example 110 | <5 |
| Example 111 | <5 |
| Example 112 | <5 |
| Example 113 | <5 |
| Example 114 | <5 |
| Example 115 | >5 |
| Example 116 | <5 |
| Example 117 | <5 |
| Example 120 | >5 |
| Example 121 | >5 |
| Example 122 | >5 |
| Example 123 | >5 |
| Example 124 | >5 |
| Example 125 | >5 |
| Example 126 | >5 |
| Example 127 | >5 |
| Example 128 | >5 |
| Example 129 | >5 |
| Example 130 | >5 |
| Example 131 | >5 |
| Example 132 | >5 |

TABLE I-continued

| Compound of Example No: | IC$_{50}$ (uM) |
|---|---|
| Example 133 | >5 |
| Example 134 | >5 |
| Example 135 | >5 |
| Example 136 | >5 |
| Example 137 | >5 |
| Example 138 | >5 |
| Example 139 | >5 |
| Example 140 | >5 |
| Example 141 | >5 |
| Example 142 | >5 |
| Example 143 | >5 |
| Example 144 | >5 |
| Example 145 | >5 |
| Example 146 | >5 |
| Example 147 | >5 |
| Example 148 | >5 |
| Example 149 | >5 |
| Example 150 | >5 |
| Example 151 | >5 |
| Example 152 | >5 |
| Example 153 | ND |
| Example 154 | >5 |
| Example 155 | >5 |
| Example 156 | >5 |
| Example 157 | >5 |
| Example 159 | >5 |
| Example 160 | >5 |
| Example 161 | >5 | where ND means "not determined"

Results: The results of the compound testing are presented in TABLE 1, above. As stated previously, it was not initially apparent whether or not inhibition of PPIase activity was necessary and sufficient for immunosuppression. Presently, the prevailing thought is that binding to the PPIase enzyme may be necessary but is not sufficient. Therefore, the data on PPIase inhibition may be viewed as an assay to detect whether or not a given compound is capable of interacting productively with FKBP.

2) Human T Lymphocyte Inhibition

Inhibition of mitogen-induced T-cell proliferation can be used to profile immunosuppressive activity of test compounds. In the description of the assay which follows, mitogen-induced T-cell activation was used to test the inhibitory potencies of select compounds of the present invention.

In an assay similar to that described by Bradley in Mishell et al. (Eds.), 1980, *Selected Methods in Cellular Immunology*, pp 156–161, W. H. Freeman & Co., San Fransisco, Calif., T-cells were stimulated by incubation with phytohemagglutinin (PHA) which binds to cell surface molecules, including the T-cell receptor. This stimulation results in proliferation which can be measured by incorporation of [$^3$H]-thymidine into cellular DNA.

The immunosuppressive properties of the compounds of the present invention can be determined by adding various concentrations of the compounds to these cultures and measuring the effect on T-cell proliferation.

EXAMPLE 163

Suppression of Human T-Cell Proliferation Assay

Fresh LeukoPaks were obtained from the New York Blood Center, New York, N.Y. The cells, including erythrocytes and leukocytes, were diluted with Hank's Balanced Salt Solution (HBSS) (GIBCO, Grand Island, N.Y.) and layered over Lymphoprep (Nycomed Pharma AS, Oslo, Norway) in sterile 50 ml conical centrifuge tubes. Lymphocytes were isolated at the Hank's/Nycomed interface after centrifugation at 2000×g, 4° C. for 15 min. The lymphocytes were washed with Minimal Essential Medium (GIBCO) containing 2% fetal bovine serum (FBS) (Sigma Chemical Co., St. Louis, Mo.), 1% HEPES buffer (GIBCO) and 1% Penicillin-Stretomycin solution (GIBCO).

T-cells were further purified essentially by sheep erythrocyte (SRBC) rosetting as described by Morimoto et al., 1983, J. Immunol. 130:157. The isolated lymphocytes were adjusted to 2×10$^7$ cells/ml and 5 ml aliquots of the cell suspension were incubated for 10 minutes at room temperature with 5 ml of a 5% SRBC (Cappel, Organon Technika Corp., West Chester, Pa.) suspension. The cells were gently pelleted by centrifugation at 300 rpm for 10 minutes, followed by a 1 hour incubation at room temperature to allow rosette formation. The cells were gently resuspended, layered over Lymphoprep and centrifuged for 30 minutes at 500×g. The pellet, containing rosetted T-cells and SRBC was treated with ice cold buffered ammonium chloride (GIBCO) to lyse the erythrocytes. T-cells were washed twice with HBSS.

Purified T-cells were resuspended at 2×10$^6$ cells/ml in complete culture medium composed of RPMI-1640 (Whittaker Bioproducts, Walkerville, Md.) with 10% FBS (Sigma), 2 mM L-glutamine (GIBCO), 1% Penicillin-Streptomycin (GIBCO) and 15 mM HEPES (GIBCO). In 96-well plates (Becton Dickinson, Lincoln Park, N.J.), 0.1 ml aliquots of T-cell suspension were mixed with 0.05 ml of 40 µg/ml PHA-M (Sigma). The compounds of this invention were dissolved in dimethylsulfoxide at 10 mM and various dilutions in complete medium were added in duplicate wells (0.05 ml/well). The plates were incubated at 37° C. in a humidified atmosphere of 5% carbon dioxide and 95% air for 72 hours.

Proliferation was assessed by measurement of [$^3$H]-thymidine incorporation. During the last 6 hours of incubation, the cells were pulse labelled with 1 µCi/well of [$^3$H]-thymidine (New England Nuclear, Boston, Mass.). The cells were harvested onto glass fiber paper using a plate harvester and the radioactivity incorporated into cellular DNA corresponding to individual wells was measured by standard liquid scintillation counting methods. The mean counts per minute (CPM) of replicate wells was calculated and linear regression analysis of mean CPM versus compound concentration was used to determine the concentration of compound which would inhibit [$^3$H]-thymidine incorporation of T-cells by 50% (IC$_{50}$).

The results of this assay, presented in TABLE 2, are representative of the intrinsic immunosuppresive activity of the compounds of the present invention. Thus, concentrations less than 10 µM of some of the preferred compounds suppress the T-cell proliferative response by 50%, e.g., compounds of Example Nos. 39, 41, 62, 63, 66, 90, 92 and 93.

TABLE 2

| Compound of Example No: | IC$_{50}$ (uM) |
|---|---|
| Example 5: | ND |
| Example 6 | ND |
| Example 7 | <50 |
| Example 8 | 50 |
| Example 9 | 50 |
| Example 10 | <50 |
| Example 11 | 34 |

TABLE 2-continued

| Compound of Example No: | IC$_{50}$ (uM) |
|---|---|
| Example 12 | 35 |
| Example 13 | >50 |
| Example 14 | >50 |
| Example 15 | 17 |
| Example 16 | >50 |
| Example 17 | >50 |
| Example 18 | 6 |
| Example 19 | 18 |
| Example 20 | <11 |
| Example 21 | 34 |
| Example 22 | 42 |
| Example 23 | 62 |
| Example 24 | 12 |
| Example 25 | 63 |
| Example 26 | 58 |
| Example 27 | 20 |
| Example 28 | ND |
| Example 29 | ND |
| Example 30 | ND |
| Example 31 | 32 |
| Example 32 | 41 |
| Example 33 | 42 |
| Example 34 | 40 |
| Example 35 | 43 |
| Example 36 | 20 |
| Example 37 | >100 |
| Example 38 | ND |
| Example 39 | 6 |
| Example 40 | 17 |
| Example 41 | 6 |
| Example 42 | 7 |
| Example 43 | 16 |
| Example 44 | 12 |
| Example 45 | 20 |
| Example 46 | 13 |
| Example 50 | ND |
| Example 51 | ND |
| Example 52 | >50 |
| Example 53 | 16 |
| Example 54 | ND |
| Example 55 | 13 |
| Example 56 | 8 |
| Example 57 | 8 |
| Example 58 | 7 |
| Example 59 | 10 |
| Example 60 | 16 |
| Example 61 | 17 |
| Example 62 | 4 |
| Example 63 | 6 |
| Example 64 | 7 |
| Example 65 | 8 |
| Example 66 | 3 |
| Example 67 | 19 |
| Example 68 | 16 |
| Example 69 | 8 |
| Example 70 | 7 |
| Example 71 | >50 |
| Example 72 | ND |
| Example 73 | >50 |
| Example 74 | <50 |
| Example 75 | 37 |
| Example 76 | >50 |
| Example 77 | 28 |
| Example 78 | 100 |
| Example 79 | ND |
| Example 80 | ND |
| Example 81 | ND |
| Example 82 | 20 |
| Example 83 | 7 |
| Example 84 | >100 |
| Example 85 | 22 |
| Example 86 | 22 |
| Example 87 | 8 |
| Example 88 | 16 |
| Example 89 | 8 |
| Example 90 | 6 |
| Example 91 | 4 |
| Example 92 | 6 |
| Example 93 | 6 |
| Example 96 | 8 |
| Example 97 | 12 |
| Example 98 | 7 |
| Example 99 | >15 |
| Example 100 | >15 |
| Example 101 | >15 |
| Example 102 | >15 |
| Example 103 | >15 |
| Example 104 | >15 |
| Example 105 | >15 |
| Example 106 | >15 |
| Example 107 | 1 |
| Example 108 | >15 |
| Example 109 | 5 |
| Example 110 | 6 |
| Example 111 | 7 |
| Example 112 | 7 |
| Example 113 | 8 |
| Example 114 | 7 |
| Example 115 | 7 |
| Example 116 | 6 |
| Example 117 | >15 |
| Example 120 | 7 |
| Example 121 | 7 |
| Example 122 | 8 |
| Example 123 | 10 |
| Example 124 | >15 |
| Example 125 | >15 |
| Example 126 | 10 |
| Example 127 | >15 |
| Example 128 | 4 |
| Example 129 | 10 |
| Example 130 | 4 |
| Example 131 | 22 |
| Example 132 | 24 |
| Example 133 | 22 |
| Example 134 | 19 |
| Example 135 | 14 |
| Example 136 | 7 |
| Example 137 | 16 |
| Example 138 | 18 |
| Example 139 | 4 |
| Example 140 | 10 |
| Example 141 | 7 |
| Example 142 | 12 |
| Example 143 | 3 |
| Example 144 | 19 |
| Example 145 | 4 |
| Example 146 | >15 |
| Example 147 | 8 |
| Example 148 | >15 |
| Example 149 | >15 |
| Example 150 | >15 |
| Example 151 | 4 |
| Example 152 | 8 |
| Example 153 | >15 |
| Example 154 | 13 |
| Example 155 | 9 |
| Example 156 | 6 |
| Example 157 | 5 |
| Example 159 | 10 |
| Example 160 | >15 |
| Example 161 | 9 | where ND means "not determined"

3) NF-AT Assay

Stimulation of T-cells leads to the appearance of several transcription factors, including one designated "NF-AT". These factors are involved in regulation of gene expression required for immunologic activation. Some of these transcription factors appear to have functions in a wide variety of cell types. By contrast, NF-AT is found primarily in T-cells and its role is restricted to early gene activation. In addition, NF-AT activity is inhibited by the immunosuppressant drugs, Cyclosporin A and FK506 (Schreiber et al., 1992, Immunology Today 13:136).

Inhibition of NF-AT activity is measured using FGL-5 cells. FGL-5 is a cloned line of stably transfected Jurkat T-cells that contain two construct in which three tandem copies of the NF-AT DNA binding site direct transcription of both murine CD8 and the lacZ gene, encoding β-galactosidase (Fiering et al., 1990, Genes & Development 4:1823). When these cells are stimulated with phorbol esters which activate protein kinase C and calcium ionophore to raise the intracellular calcium concentration, transcriptionally active NF-AT is produced. In T-cells, this normally leads to the expression of IL-2, T-cell growth factor. However, in FGL-5 cells NF-AT activation leads to the production of β-galactosidase which can be detected using an appropriate substrate.

FGL-5 cells were cultured with phorbol ester, calcium ionophore and the compounds of the present invention to measure inhibition of β-galactosidase activity, as shown below.

EXAMPLE 164

NF-AT Inhibition Assay Directed β-Galactosidase Expression

This assay was performed essentially as described (Bierer et al., 1990, Proc. Natl. Acad. Sci. 87:9231). FGL-5 cells were maintained in medium consisting of RPMI-1640 with 10% FBS, 2 mM L-glutamine, 1% Penicillin-Streptomycin and 15 mM HEPES buffer. The assays were done with exponentially growing cells whose density was not greater than 0.5 million cells/ml. The cells were resuspended to 3 million cells/ml in medium and 0.1 ml was added to wells of a 96-well plate.

The compounds of the present invention were dissolved in either ethanol or dimethylsulfoxide at 10 mM and 0.5 ml/well of various dilutions in medium were added to cells in duplicate wells. Treatment controls consisted of duplicate wells containing 0.5 ml/well of either medium, ethanol or dimethylsulfoxide. The ethanol and dimethyl sulfoxide were at the same concentration as was used for the compounds. Cells were incubated with compounds at room temperature for 10–15 minutes. Phorbol dibutyrate (Sigma) and Ionomycin (Calbiochem) were dissolved at 50 μg/ml and 2 mM, respectively and stored at −70° C.

FGL-5 cells were stimulated by diluting these reagents with medium to 200 ng/ml and 8 μM, respectively and adding of 0.5 ml/well. For unstimulated cell controls, 0.5 ml/well of medium was added to duplicate wells. The plates were incubated overnight (16–18 hours) at 37° C. in a humidified atmosphere of 5% CO2 and air.

β-galactosidase activity was measured as the fluorescence generated by the cleavage of 4-methyl umbelliferyl-β-D-galactoside (Sigma) at the β-galactoside bond. After overnight incubation, the cells were centrifuged at 500×g for 3 minutes in the 96-well plates and washed 3 times with PBS. The cells were then resuspended in 0.18 ml/well of reaction medium containing 100 mM sodium phosphate buffer, pH 7.0, 10 mM potassium chloride, 1 mM magnesium sulfate, 0.1% Triton X-100 (Pierce, Rockford, Ill.), and 0.5 mM 4-methylumbelliferyl-β-D-galactoside.

The fluorescence at 460 nm using 355 nm excitation was measured at intervals over 1–2 hours (during which fluorescence increased linearly with time) with a LS50 Luminescence Spectrometer (Perkin Elmer).

The percent inhibition by each concentration of the compounds was calculated as:

% Inhibition=1-(fluorescence with compound-unstimulated control/fluorescence with solvent alone-unstimulated control)

The values of the concentration of compounds required for 50% inhibition ($IC_{50}$) were determined by linear regression analysis of the percent inhibition at various compound concentrations.

The results of this assay presented in TABLE 3 are representative of the intrinsic immunosuppresive activity of the compounds of the present invention. Those compounds that inhibited NF-AT directed β-galactosidase expression by stimulated FGL-5 cells with $IC_{50}$ <10 μM also inhibited mitogen induced T cell proliferation, e.g., compounds of Example Nos. 87, 89, 107, 114 and 159.

TABLE 3

| Compound of Example No: | $IC_{50}$ (uM) |
| --- | --- |
| Example 5 | n.d. |
| Example 6 | n.d. |
| Example 7 | n.d. |
| Example 8 | n.d. |
| Example 9 | n.d. |
| Example 10 | n.d. |
| Example 11 | n.d. |
| Example 12 | n.d. |
| Example 13 | n.d. |
| Example 14 | n.d. |
| Example 15 | n.d. |
| Example 16 | n.d. |
| Example 17 | n.d. |
| Example 18 | n.d. |
| Example 19 | n.d. |
| Example 20 | n.d. |
| Example 21 | n.d. |
| Example 22 | n.d. |
| Example 23 | n.d. |
| Example 24 | n.d. |
| Example 25 | n.d. |
| Example 26 | n.d. |
| Example 27 | n.d. |
| Example 28 | n.d. |
| Example 29 | n.d. |
| Example 30 | n.d. |
| Example 31 | n.d. |
| Example 32 | n.d. |
| Example 33 | n.d. |
| Example 34 | n.d. |
| Example 35 | n.d. |
| Example 36 | 13 |
| Example 37 | >100 |
| Example 38 | n.d. |
| Example 39 | 41 |
| Example 40 | 19 |
| Example 41 | 13 |
| Example 42 | 22 |
| Example 43 | 14 |
| Example 44 | 24 |
| Example 45 | >33 |
| Example 46 | 15 |
| Example 50 | n.d. |
| Example 51 | n.d. |
| Example 52 | n.d. |
| Example 53 | n.d. |
| Example 54 | n.d. |
| Example 55 | 44 |
| Example 56 | 73 |
| Example 57 | >100 |
| Example 58 | 20 |
| Example 59 | >100 |
| Example 60 | 18 |
| Example 61 | >100 |
| Example 62 | 13 |

TABLE 3-continued

| Compound of Example No: | IC$_{50}$ (uM) |
|---|---|
| Example 63 | 20 |
| Example 64 | 16 |
| Example 65 | 17 |
| Example 66 | 57 |
| Example 67 | >100 |
| Example 68 | 60 |
| Example 69 | 16 |
| Example 70 | 16 |
| Example 71 | n.d. |
| Example 72 | n.d. |
| Example 73 | n.d. |
| Example 74 | n.d. |
| Example 75 | n.d. |
| Example 76 | n.d. |
| Example 77 | n.d. |
| Example 78 | n.d. |
| Example 79 | n.d. |
| Example 80 | n.d. |
| Example 81 | n.d. |
| Example 82 | n.d. |
| Example 83 | 12 |
| Example 84 | >100 |
| Example 85 | 13 |
| Example 86 | 13 |
| Example 87 | 6 |
| Example 88 | 13 |
| Example 89 | 5 |
| Example 90 | >100 |
| Example 91 | 26 |
| Example 92 | 44 |
| Example 93 | 19 |
| Example 96 | 24 |
| Example 97 | 32 |
| Example 98 | >33 |
| Example 99 | >15 |
| Example 100 | >15 |
| Example 101 | >15 |
| Example 102 | >15 |
| Example 103 | >15 |
| Example 104 | >15 |
| Example 105 | >15 |
| Example 106 | >15 |
| Example 107 | 0.6 |
| Example 108 | >15 |
| Example 109 | >15 |
| Example 110 | >15 |
| Example 111 | >15 |
| Example 112 | >15 |
| Example 113 | >15 |
| Example 114 | 10 |
| Example 115 | >15 |
| Example 116 | 14 |
| Example 117 | >15 |
| Example 120 | >15 |
| Example 121 | >15 |
| Example 122 | >15 |
| Example 123 | >15 |
| Example 124 | >15 |
| Example 125 | >15 |
| Example 126 | >15 |
| Example 127 | >15 |
| Example 128 | >15 |
| Example 129 | >15 |
| Example 130 | >15 |
| Example 131 | >33 |
| Example 132 | >33 |
| Example 133 | >33 |
| Example 134 | >33 |
| Example 135 | >33 |
| Example 136 | >33 |
| Example 137 | >33 |
| Example 138 | >33 |
| Example 139 | >33 |
| Example 140 | >33 |
| Example 141 | >33 |
| Example 142 | >33 |
| Example 143 | >33 |
| Example 144 | >33 |
| Example 145 | >33 |
| Example 146 | >15 |
| Example 147 | >15 |
| Example 148 | >15 |
| Example 149 | >15 |
| Example 150 | >15 |
| Example 151 | >15 |
| Example 152 | >15 |
| Example 153 | >15 |
| Example 154 | >15 |
| Example 155 | >15 |
| Example 156 | >15 |
| Example 157 | >15 |
| Example 159 | 3 |
| Example 160 | >15 |
| Example 161 | >15 | where n.d. means "not determined"

4) Graft versus Host Assay

Inhibition of the graft versus host response (herinafter "GVHR") by the compounds of the present invention is another means to demonstrate their immunosuppressive activity. Transfer of parental strain T-cells (the graft) into F1 hybrid animals (the host) major different with respect to gene products of the histocompatibility complex (MHC) causes a GVHR. This reaction results from recognition of host allogeneic MHC gene products by specific clones of graft T-cells.

When given systemically in sufficient numbers, the graft T-cells cause a progressive, generally fatal, wasting syndrome. A local, nonfatal GVHR, marked by enlargement of the draining popliteal lymph nodes, ensues when graft T-cells are administered via the footpad as described by Ford et al., 1970, Transplantation 10:258. The GVHR is regarded as a correlate of allograft rejections where specific T-cells of either host or allograft origin are activated after recognition of allogeneic MHC gene products, leading to an immune inflammatory response which ultimately results in the destruction (rejection) of the allograft.

EXAMPLE 165

Mouse Lymph Node Assay for Modulation of Graft versus Host Response

Single cell suspensions in phosphate buffered saline (PBS) were prepared from the spleens of BDF1 and $C_{57}B1/6$ mice (Jackson Labs, Bar Harbor, Me.). The cells were pelleted by centifugation at 500×g for 5 minutes and the pellet resuspended in 0.9 ml distilled water to lyse erythrocytes. After 5 seconds, 0.1 ml 10× concentrated PBS was added, resulting in an isotonic solution. The cells were washed with PBS and resuspended at $2 \times 10^8$ cells/ml. $1 \times 10^7$ cells in 0.05 ml PBS were injected subcutaneously into the hind footpads (BDF1 cells in one footpad, $C_{57}B1/6$ cells in the other). The test compounds were dissolved in ethanol, mixed with olive oil (1:7, ethanol:olive oil). Some mice received intraperitoneal injections (0.2 ml/injection) of either ethanol:olive oil alone (vehicle control group) or compound at 100 mg/kg per day, beginning on the same day as the spleen cell injections.

After 7 days, the draining popliteal lymph nodes from the hind limbs were dissected out and weighed. The magnitude of the GVHR was expressed as the ratio of the mean weight of lymph nodes from the limb injected with semi-allogeneic $C_{57}B1/6$ cells divided by the mean weight of lymph nodes from the limb injected with syngeneic BDF1 cells.

The results presented in TABLE 4 show that a representative compound of this invention which is a potent inhibitor of both FKBP activity and mitogen-induced T-cell proliferation also inhibited the localized GVHR. Thus, for the untreated or vehicle control groups, the mean lymph node weights from BDF1-sensitized limbs were 2.2–3.1 times that of $C_{57}B1/6$-sensitized limbs. By contrast, in mice treated with the test compound, virtually no GVHR was detected (ratio=1.2). For comparison, in this example a group of mice was treated with 100 mg/kg/day of cyclosporin A (Sandoz Ltd., Basel, Switzerland). Cyclosporin A also inhibited the GVHR (ratio=1.6).

TABLE 4

| Treatment | Lymph Node Weight Ratio |
| --- | --- |
| None | 3.1 |
| Vehicle alone | 2.2 |
| Compound of Example 24 | 1.2 |
| Cyclosporin A | 1.6 |

What is claimed is:

1. A compound having T-lymphocyte inhibitory activity and the generalized structure

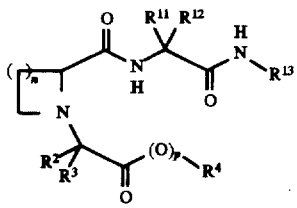

wherein n is 2 or 3;

one of $R^2$ and $R^3$ is H, and the other is H or $CH_3$;

p is 0 or 1; and when p is 0, $R^4$ is
  a) cyclohexyl optionally substituted by alkyl of 4–5 carbon atoms, or by phenyl, or by substituted phenyl wherein the substituent is halogen or methyl;
  b) bicycloheptyl optionally substituted up to three-fold by methyl;
  c) tricycloalkyl of 10 carbon atoms;
  d) 1,2,3,4-tetrahydronaphthyl; or
  e) methyl substituted by tricycloalkyl of 10 carbon atoms, which is in turn optionally substituted by methyl;

when p is 1, $R^4$ is
  f) butenyl substituted at least once by phenyl or by a diene of 11 carbon atoms;
  g) alpha-substituted benzyl wherein the alpha substituent is an alkyl group of 2–3 carbon atoms or cyclohexyl; or
  h) tricycloalkyl of 10 carbon atoms, substituted once by methyl;

one of $R^{11}$ and $R^{12}$ is H, and the other is
  i) phenyl; or
  j) alkyl of 1–4 carbon atoms, optionally substituted by phenyl, or by benzyloxy, or by cyclohexyl; and $R^{13}$ is unsubstituted benzyl, or benzyl substituted by methyl, or benzyl wherein the phenyl moiety is substituted by methoxy.

2. A compound of claim 1 wherein n is 2;

$R^2$ and $R^3$ are H;

p is 0 or 1; and when p is 0, $R^4$ is
  a) cyclohexyl optionally substituted by alkyl of 4–5 carbon atoms, or by phenyl, or by substituted phenyl wherein the substituent is halogen or methyl;
  b) bicycloheptyl optionally substituted up to three-fold by methyl; or
  c) tricycloalkyl of 10 carbon atoms; or when p is 1, $R^4$ is
  f) butenyl substituted at least once by phenyl;
  g) alpha-substituted benzyl wherein the alpha substituent is an alkyl group of 2–3 carbon atoms or cyclohexyl; or
  h) tricycloalkyl of 10 carbon atoms, substituted once by methyl;

one of $R^{11}$ and $R^{12}$ is H, and the other is
  j) alkyl of 1–4 carbon atoms, optionally substituted by phenyl, or by benzyloxy, or by cyclohexyl; and $R^{13}$ is benzyl.

3. A compound of claim 1 wherein the compound is:
  a) L-Isoleucine, N-[1-(2-Adamantan-1-yl-2-Oxoethyl)-L-Prolyl] Benzylamide;
  b) L-Isoleucine, N-[1-[2-(2,6,6-Trimethyl-Bicyclo[3.1.1] hept-3-yl)-2-Oxoethyl] -L-Prolyl] Benzylamide;
  c) L-Leucine, N-[1-(2-Adamantan-1-yl-2-Oxoethyl)-L-Prolyl] Benzylamide;
  d) L-Norvaline, N-[1-(2-Adamantan-1-yl-2-Oxoethyl)-L-Prolyl] Benzylamide;
  e) L-Norleucine, N-[1-(2-Adamantan-1-yl-2-Oxoethyl)-L-Prolyl] Benzylamide;
  f) L-β-Phenylalanine, N-[1-(2-Adamantan-1-yl-2-Oxoethyl)-L-Prolyl] Benzylamide;
  g) L-Cyclohexylalanine, N-[1-(2-Adamantan-1-yl-2-Oxoethyl)-L-Prolyl] Benzylamide;
  h) L-Isoleucine, N-[1-(2-Adamantan-1-yl-2-Oxoethyl)-L-Prolyl] alpha-(S)-methylbenzylamide;
  i) L-Isoleucine, N-[1-(2-Adamantan-1-yl-2-Oxoethyl)-L-Prolyl] alpha-(R)-methylbenzylamide;
  j) L-Isoleucine, N-[1-(2-Adamantan-1-yl-2-Oxoethyl)-L-Prolyl] 4-methoxybenzylamide;
  k) L-Isoleucine, N-[1-(2-Adamantan-1-yl-2-Oxoethyl)-L-Prolyl] 2-methoxybenzylamide;
  l) L-Isoleucine, N-[1-(2-(1-Phenylpropoxy)-2-Oxoethyl)-L-Prolyl] Benzylamide;
  m) L-Isoleucine, N-[1-(2-(2-Oxy-2-Methyladamant-2-yl) -2-Oxoethyl)-L-Prolyl] Benzylamide;
  n) L-Isoleucine, N-[1-(2-(2-Methyl-1-(S)-Phenyl-1-Propoxy)-2-Oxoethyl)-L-Prolyl] Benzylamide; or
  o) L-Isoleucine, N-[1-(2-(2-Methyl-1-(R)-Phenyl-1-Propoxy)-2-Oxoethyl)-L-Prolyl] Benzylamide.

4. A compound of claim 1 having the name L-Isoleucine, N-[1-(2-(1-(4-Chlorophenyl)cyclohexyl)-2-Oxoethyl)-L-Prolyl] Benzylamide.

5. A compound of claim 1 having the name L-Isoleucine, N-[1-(2-(1-(Phenylcyclohexyl)-2-Oxoethyl)-L-Prolyl] Benzylamide.

6. A pharmaceutical composition comprising a compound of claim 1 plus a pharmaceutically-acceptable carrier.

7. A pharmaceutical composition comprising a compound of claim 2 plus a pharmaceutically-acceptable carrier.

8. A method for treating an inflammatory process in a subject, comprising administering to said subject an effective amount of a compound of claim 1.

9. A method for inhibiting T-lymphocyte activity in a subject, comprising administering to said subject an effective amount of a compound of claim 1.

10. A therapeutic composition for suppressing the proliferation of human T-lymphocytes, comprising an effective amount of the compound according to claim 1.

* * * * *